(12) United States Patent
Kim et al.

(10) Patent No.: US 10,476,008 B2
(45) Date of Patent: Nov. 12, 2019

(54) COMPOUND FOR ORGANIC OPTOELECTRIC DEVICE AND ORGANIC OPTOELECTRIC DEVICE AND DISPLAY DEVICE

(71) Applicant: SAMSUNG SDI CO., LTD., Yongin-si, Gyeonggi-do (KR)

(72) Inventors: Byungku Kim, Suwon-si (KR); Jinhyun Lui, Suwon-si (KR); Eun Sun Yu, Suwon-si (KR); Sangshin Lee, Suwon-si (KR); Chunkeun Jang, Suwon-si (KR); Sung-Hyun Jung, Suwon-si (KR); Ho Kuk Jung, Suwon-si (KR); Sujin Han, Suwon-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 124 days.

(21) Appl. No.: 15/456,958

(22) Filed: Mar. 13, 2017

(65) Prior Publication Data

US 2017/0317293 A1   Nov. 2, 2017

(30) Foreign Application Priority Data

May 2, 2016  (KR) .................. 10-2016-0054292

(51) Int. Cl.
| | | |
|---|---|---|
| *H01L 51/54* | (2006.01) | |
| *C09K 11/06* | (2006.01) | |
| *H01L 51/00* | (2006.01) | |
| *C07D 209/86* | (2006.01) | |
| *C07D 239/26* | (2006.01) | |
| *C07D 251/24* | (2006.01) | |
| *C07D 401/14* | (2006.01) | |
| *C07D 403/14* | (2006.01) | |
| *C07D 405/14* | (2006.01) | |
| *C07D 409/14* | (2006.01) | |
| *C09K 11/02* | (2006.01) | |
| *H01L 51/50* | (2006.01) | |

(52) U.S. Cl.
CPC ........ *H01L 51/0067* (2013.01); *C07D 209/86* (2013.01); *C07D 239/26* (2013.01); *C07D 251/24* (2013.01); *C07D 401/14* (2013.01); *C07D 403/14* (2013.01); *C07D 405/14* (2013.01); *C07D 409/14* (2013.01); *C09K 11/025* (2013.01); *H01L 51/0072* (2013.01); *H01L 51/0073* (2013.01); *H01L 51/0074* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 2251/5384* (2013.01)

(58) Field of Classification Search
CPC .. C07D 209/86; C07D 239/26; C07D 251/24; C07D 401/00; C07D 401/10; C07D 401/14; C07D 403/00; C07D 403/10; C07D 403/14; C07D 405/00; C07D 405/10; C07D 405/14; C07D 409/00; C07D 409/10; C07D 409/14; C09K 11/025; C09K 11/06; C09K 2211/00; C09K 2211/10; C09K 2211/1007; C09K 2211/1018; C09K 2211/1025; C09K 2211/1029; C09K 2211/1044; C09K 2211/1059; H01L 2251/5384; H01L 51/0032; H01L 51/005; H01L 51/0067; H01L 51/0072; H01L 51/0073; H01L 51/0074; H01L 51/50; H01L 51/5012; H01L 51/5016; H01L 51/5056; H01L 51/5072; H01L 51/5088; H01L 51/5092; H01L 51/5096

USPC ....... 428/690, 691, 917, 411.4, 336; 427/58, 427/66; 313/500–512; 257/40, 88–104, 257/E51.001–E51.052; 252/301.16–301.35

See application file for complete search history.

(56) References Cited

U.S. PATENT DOCUMENTS

| | | | |
|---|---|---|---|
| 6,225,467 B1 | 5/2001 | Esteghamatian et al. | |
| 2007/0190355 A1* | 8/2007 | Ikeda .................. | C07D 239/26 428/690 |
| 2014/0367656 A1* | 12/2014 | Kim ..................... | H01L 51/006 257/40 |
| 2015/0364693 A1 | 12/2015 | Ito et al. | |
| 2015/0380662 A1 | 12/2015 | Kim et al. | |
| 2016/0020404 A1 | 1/2016 | Ito et al. | |

FOREIGN PATENT DOCUMENTS

| | | | |
|---|---|---|---|
| CN | 1934213 A | 3/2007 | |
| JP | 5206907 B2 | 6/2013 | |
| JP | 5312824 B2 | 10/2013 | |
| KR | 10-2007-0030759 | 3/2007 | |
| KR | 10-2014-0145000 | 12/2014 | |
| WO | WO-2013187896 A1 * | 12/2013 | ........... C07D 403/14 |

OTHER PUBLICATIONS

Chinese Office action dated Jul. 19, 2019.

* cited by examiner

*Primary Examiner* — Andrew K Bohaty
(74) *Attorney, Agent, or Firm* — Lee & Morse, P.C.

(57) ABSTRACT

A compound for an organic optoelectric device represented by Chemical Formula 1, a composition for an organic optoelectric device, and an organic optoelectric device and display device including the same are disclosed. Chemical Formula 1 is the same as defined in the specification.

14 Claims, 2 Drawing Sheets

[FIG. 1]
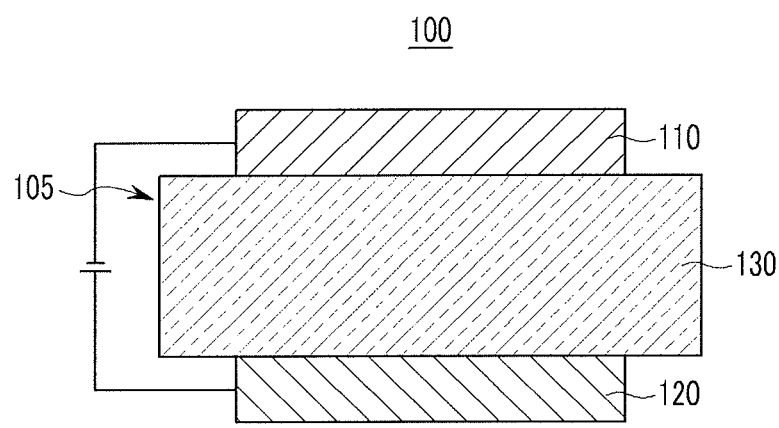
[FIG. 2]
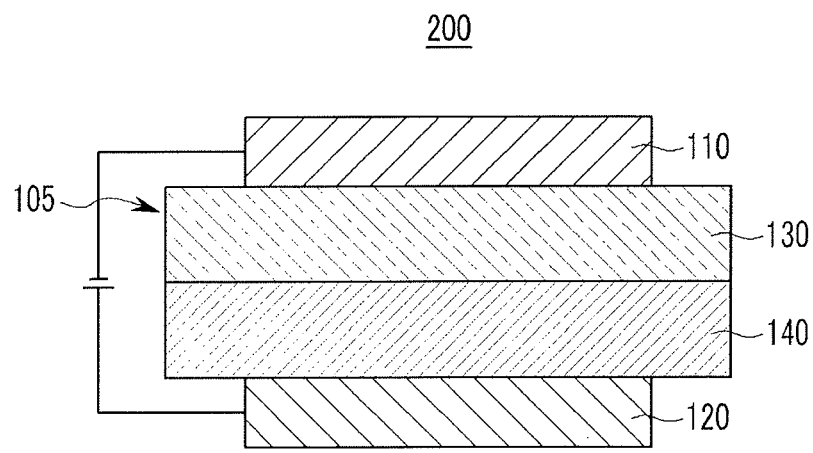

[FIG. 3]
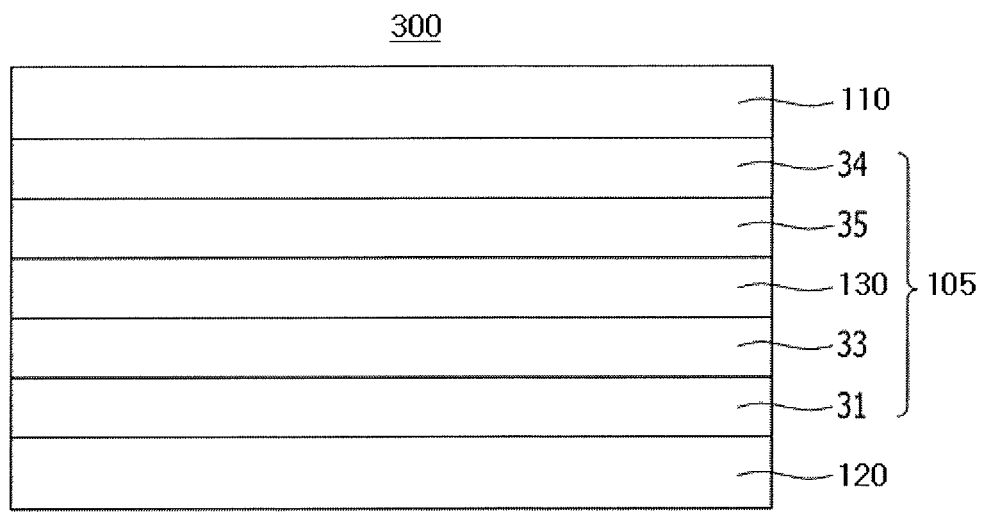
[FIG. 4]
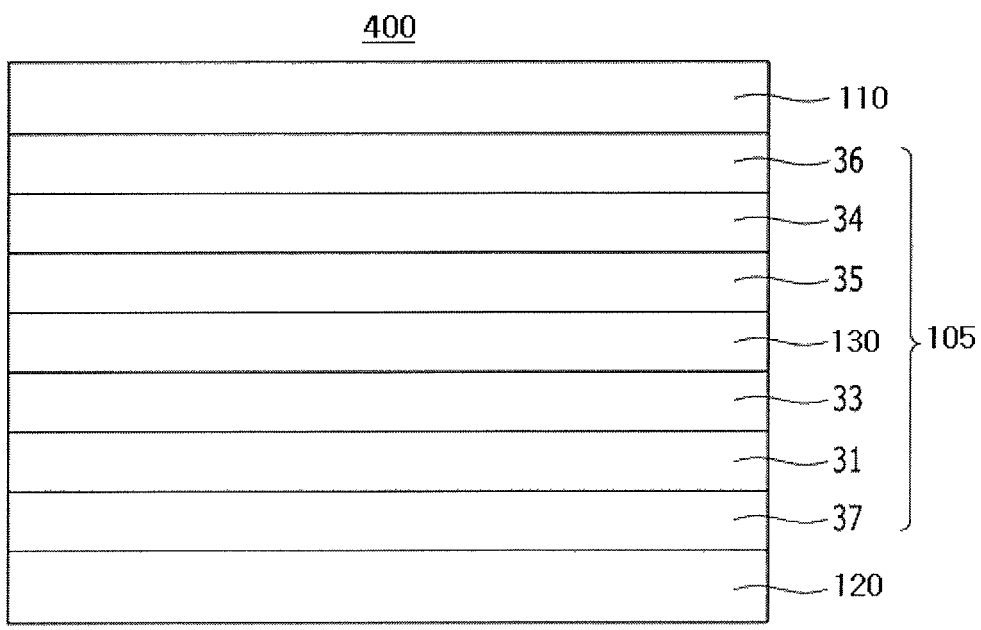

COMPOUND FOR ORGANIC OPTOELECTRIC DEVICE AND ORGANIC OPTOELECTRIC DEVICE AND DISPLAY DEVICE

CROSS-REFERENCE TO RELATED APPLICATION

This application claims priority to and the benefit of Korean Patent Application No. 10-2016-0054292 filed in the Korean Intellectual Property Office on May 2, 2016, the entire contents of which are incorporated herein by reference.

BACKGROUND OF THE INVENTION

(a) Field of the Invention

A compound for an organic optoelectric device, an organic optoelectric device, and a display device are disclosed.

(b) Description of the Related Art

An organic optoelectric device (organic optoelectric diode) is a device that converts electrical energy into photoenergy, and vice versa.

An organic optoelectric device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectric device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light by applying current to an organic light emitting material and has a structure in which an organic layer is disposed between an anode and a cathode. Herein, the organic layer may include a light-emitting layer and optionally an auxiliary layer, and the auxiliary layer may be, for example at least one selected from a hole injection layer, a hole transport layer, an electron blocking layer, an electron transport layer, an electron injection layer, and a hole blocking layer for improving efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

SUMMARY OF THE INVENTION

An embodiment provides a compound for an organic optoelectric device capable of realizing an organic optoelectric device having high efficiency and a long life-span.

Another embodiment provides a composition for an organic optoelectric device including the compound for an organic optoelectric device.

Yet another embodiment provides an organic optoelectric device including the compound.

Still another embodiment provides a display device including the organic optoelectric device.

According to an embodiment, a compound for an organic optoelectric device represented by Chemical Formula 1 is provided.

[Chemical Formula 1]

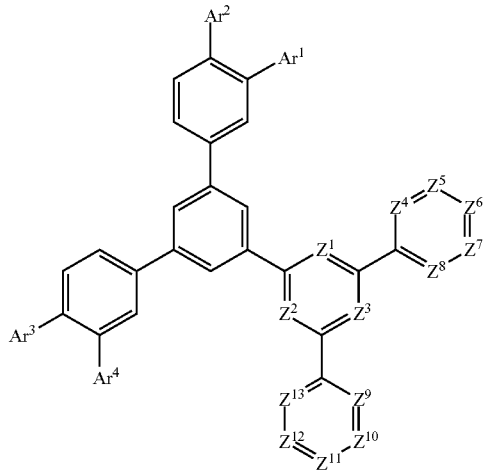

In Chemical Formula 1, $Ar^1$ to $Ar^4$ are independently hydrogen, deuterium, a substituted or unsubstituted C6 to C30 aryl group, a substituted or unsubstituted carbazolyl group, a substituted or unsubstituted dibenzofuranyl group, a substituted or unsubstituted dibenzothiophenyl group, a substituted or unsubstituted N-containing heteroaryl group, a substituted or unsubstituted arylamine group, a substituted or unsubstituted dibenzosilole group, or a combination thereof, $Z^1$ to $Z^{13}$ are independently N or $CR^a$, at least one of $Z^1$ to $Z^{13}$ is N, $R^a$ is independently hydrogen, deuterium, a substituted or unsubstituted C1 to C10 alkyl group, a C6 to C18 aryl group, or a combination thereof, and the "substituted" refers to replacement of at least one hydrogen by deuterium, a C1 to C4 alkyl group, or a C6 to C18 aryl group.

According to another embodiment, a composition for an organic optoelectric device includes the first compound for an organic optoelectric device; and at least one of a second compound for an organic optoelectric device represented by Chemical Formula 2.

[Chemical Formula 2]

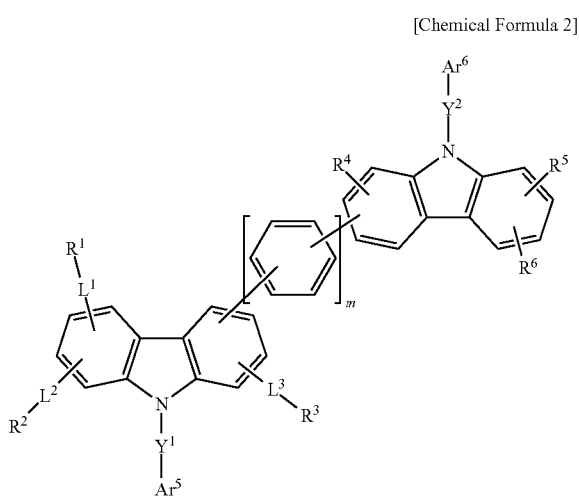

In Chemical Formula 2, $L^1$ to $L^3$, $Y^1$, and $Y^2$ are independently a single bond, a substituted or unsubstituted C6 to C30 arylene group, a substituted or unsubstituted C2 to C30 heteroarylene group, or a combination thereof, $Ar^5$ and $Ar^6$ are independently substituted or unsubstituted C6 to C30 aryl group, a substituted or unsubstituted C2 to C30 heterocyclic group, or a combination thereof, $R^1$ to $R^6$ are independently hydrogen, deuterium, a substituted or unsubstituted C1 to C20 alkyl group, a substituted or unsubstituted C6 to C30 aryl group, a substituted or unsubstituted C2 to C50 heterocyclic group, or a combination thereof, and m is an integer of 0 to 4.

According to another embodiment, an organic optoelectric device includes an anode and a cathode facing each other and at least one organic layer disposed between the anode and the cathode, wherein the organic layer includes the compound for an organic optoelectric device.

According to yet another embodiment, a display device including the organic optoelectric device is provided.

An organic optoelectric device having high efficiency and a long life-span may be realized.

BRIEF DESCRIPTION OF THE DRAWINGS

FIGS. 1 to 4 are cross-sectional views showing organic light emitting diodes according to embodiments.

DETAILED DESCRIPTION

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C6 to C30 heteroaryl group, a C1 to C20 alkoxy group, a fluoro group, a C1 to C10 trifluoroalkyl group such as a trifluoromethyl group, or a cyano group. In one example of the present invention, "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C6 to C30 heteroaryl group. In specific examples of the present invention, "substituted" refers to replacement of at least one hydrogen of a substituent or a compound by deuterium, a C1 to C30 alkyl group, a C6 to C18 aryl group, or a C6 to C20 heteroaryl group.

In the present specification, when specific definition is not otherwise provided, "hetero" refers to one including 1 to 3 heteroatoms selected from N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have 1 to 4 carbon atoms in alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one heteroatom selected from N, O, S, P, and Si instead of carbon (C) in a cyclic compound such as aryl group, a cycloalkyl group, a fused ring thereof, or a combination thereof. When the heterocyclic group is a fused ring, the entire ring or each ring of the heterocyclic group may include one or more heteroatoms.

For example, a "heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include 1 to 3 heteroatoms.

Specific examples of the heteroaryl group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

In the present specification, hole characteristics refer to an ability to donate an electron to form a hole when an electric field is applied, and that a hole formed in the anode may be easily injected into a light-emitting layer, and a hole formed in a light-emitting layer may be easily transported into an anode and transported in a light-emitting layer due to conductive characteristics according to a highest occupied molecular orbital (HOMO) level.

In addition, electron characteristics refer to an ability to accept an electron when an electric field is applied and that an electron formed in a cathode may be easily injected into a light-emitting layer, and an electron formed in a light-emitting layer may be easily transported into a cathode and transported in a light-emitting layer due to conductive characteristics according to a lowest unoccupied molecular orbital (LUMO) level.

Hereinafter, a compound for an organic optoelectric device according to an embodiment is described.

A compound for an organic optoelectric device according to one embodiment is represented by Chemical Formula 1.

[Chemical Formula 1]

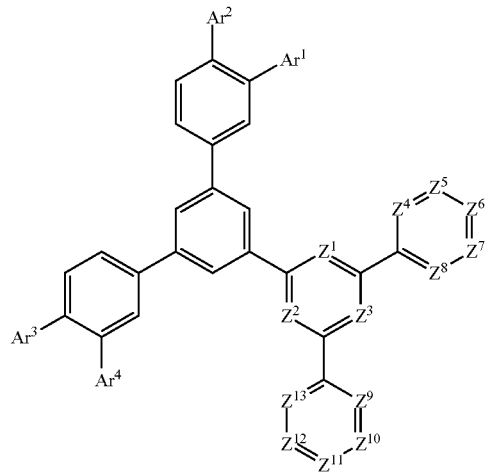

In Chemical Formula 1, $Ar^1$ to $Ar^4$ are independently hydrogen, deuterium, a substituted or unsubstituted C6 to C30 aryl group, a substituted or unsubstituted carbazolyl group, a substituted or unsubstituted dibenzofuranyl group, a substituted or unsubstituted dibenzothiophenyl group, a substituted or unsubstituted N-containing heteroaryl group, a substituted or unsubstituted arylamine group, a substituted or unsubstituted dibenzosilole group, or a combination thereof, $Z^1$ to $Z^{13}$ may each be $sp^2$ bonded and are independently N or $CR^a$, at least one of $Z^1$ to $Z^{13}$ is N, $R^a$ is independently hydrogen, deuterium, a substituted or unsubstituted C1 to C10 alkyl group, a C6 to C18 aryl group, or a combination thereof, and the "substituted" refers to replacement of at least one hydrogen by deuterium, a C1 to C4 alkyl group, or a C6 to C18 aryl group.

In an example embodiment, at least two of $Z^1$ to $Z^3$ may be N, for example all three of $Z^1$ to $Z^3$ may be N.

The compound for an organic optoelectric device according to the present invention has a structure where a combined moiety of phenyl groups is linked with a hexagonal nitrogen-containing moiety.

The combined moiety of phenyl groups has a dendrimer structure where two phenyl groups are linked with phenylene of a core in a meta position and thus structural steric hindrance is present in the molecule. Thereby, crystallization is suppressed due to a small molecular interaction, and thus a manufacturing yield of an organic optoelectric device including the compound may be improved and an organic optoelectric device having a long life-span may be obtained.

In addition, a molecular weight and solubility may be controlled due to inclusion of various substituents, and thus the compound may be applied to a deposition or solution process, and a HOMO energy level and an LUMO energy level may be easily controlled, and thus injection and transport characteristics of holes and charges may be improved and thus a driving voltage may be lowered.

An asymmetric structure of the compound lowers a deposition temperature and suppresses decomposition during deposition, and thus a life-span of an organic optoelectric device including the compound may be improved and a driving voltage may be lowered.

Chemical Formula 1 may be, for example represented by Chemical Formula 1-A, 1-B, 1-C, 1-D, 1-E, 1-F, 1-G, 1-H, 1-I, or 1-J according a structure of the hexagonal nitrogen-containing moiety.
[Chemical Formula 1-A]
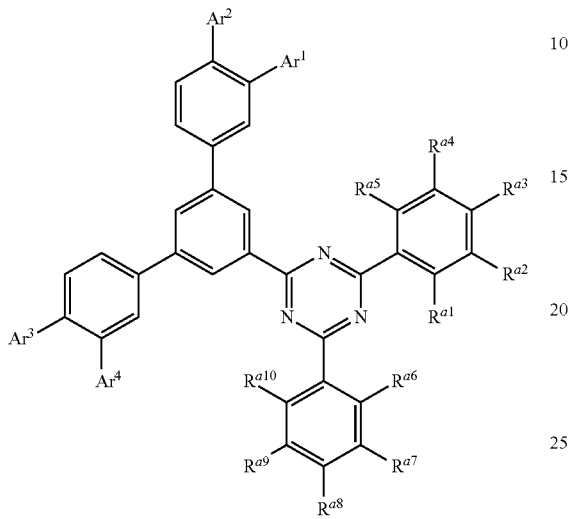
[Chemical Formula 1-B]
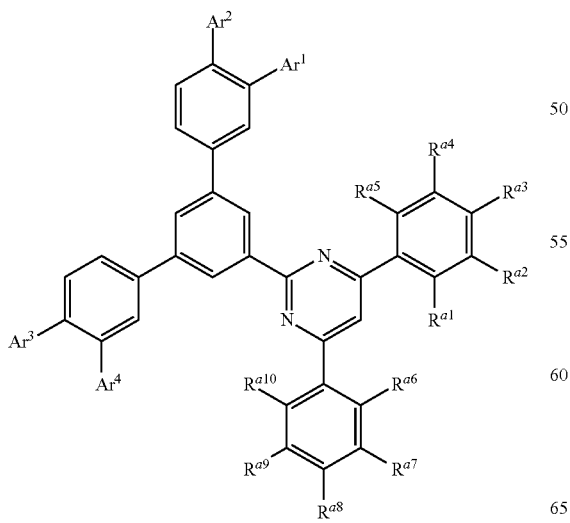
[Chemical Formula 1-C]
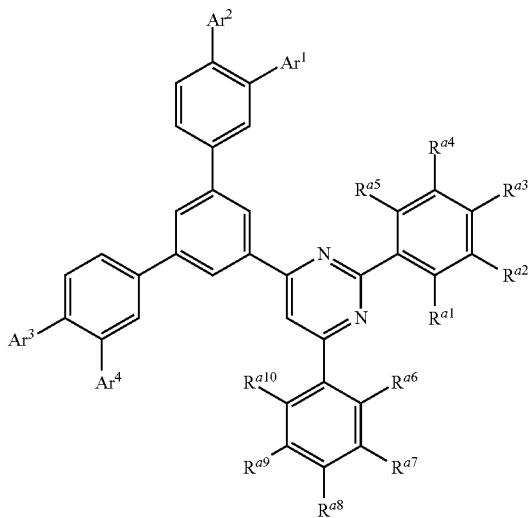
[Chemical Formula 1-D]
[Chemical Formula 1-E]
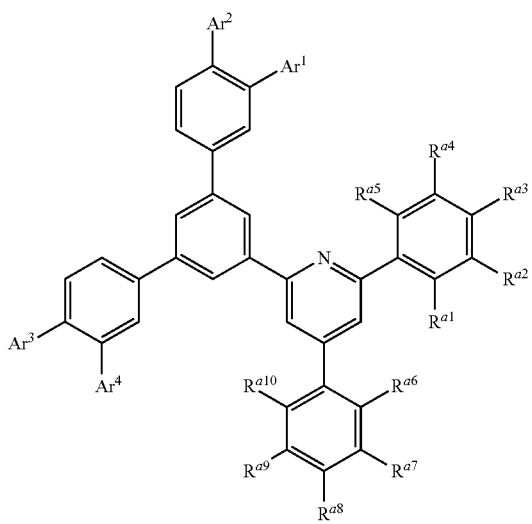

[Chemical Formula 1-F]

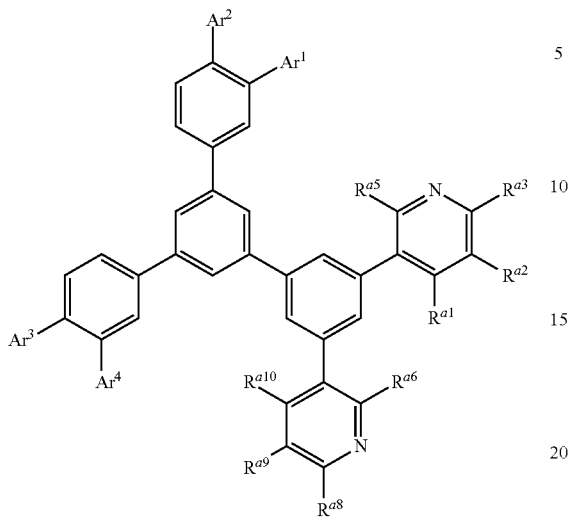

[Chemical Formula 1-G]

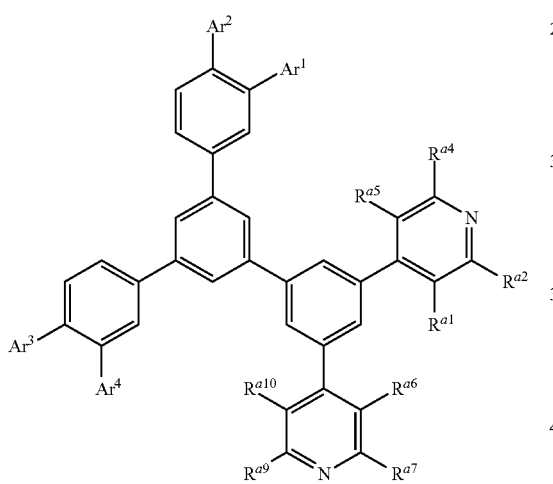

[Chemical Formula 1-H]

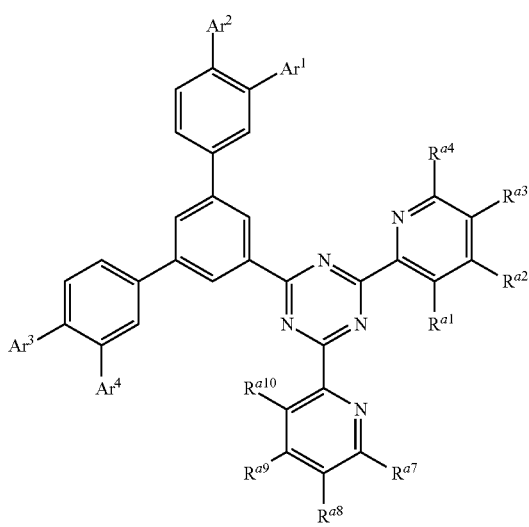

[Chemical Formula 1-I]

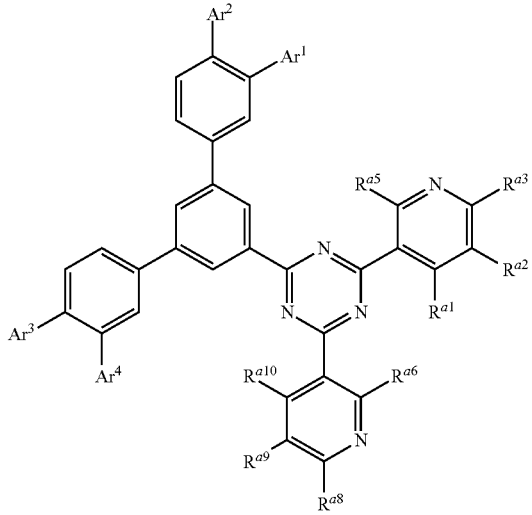

[Chemical Formula 1-J]

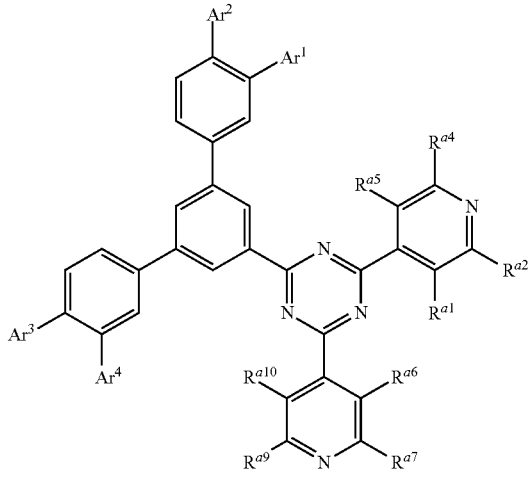

In Chemical Formulae 1-A to 1-J, $Ar^1$ to $Ar^4$ are the same as described above and $R^{a1}$ to $R^{a10}$ are the same as $R^a$.

In an example embodiment of the present invention, $R^{a1}$ to $R^{a10}$ may independently be hydrogen, deuterium, a substituted or unsubstituted C1 to C10 alkyl group, a C6 to C18 aryl group, or combination thereof, specifically hydrogen, deuterium, a substituted or unsubstituted phenyl group, a substituted or unsubstituted biphenyl group, or a substituted or unsubstituted terphenyl group, and more specifically hydrogen, or a substituted or unsubstituted phenyl group.

For example, $R^{a1}$ to $R^{a10}$ may be all hydrogen or at least one of $R^{a2}$ to $R^{a4}$ and $R^{a7}$ to $R^{a9}$ may be a phenyl group, but are not limited thereto.

In an example embodiment of the present invention, $Ar^1$ to $Ar^4$ may independently be hydrogen, deuterium, a substituted or unsubstituted C6 to C30 aryl group, a substituted or unsubstituted carbazolyl group, a substituted or unsubstituted dibenzofuranyl group, a substituted or unsubstituted dibenzothiophenyl group, a substituted or unsubstituted N-containing heteroaryl group, a substituted or unsubstituted arylamine group, a substituted or unsubstituted dibenzosilole group, or a combination thereof. Specifically, $Ar^1$ to $Ar^4$ may independently be hydrogen, deuterium, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylenyl group, a substituted or unsubstituted fluorenyl group, a substituted or unsubstituted carbazolyl group, a substituted or unsubstituted dibenzofuranyl group, a substituted or unsubstituted dibenzothiophenyl group, diphenylamine group, a substituted or unsubstituted pyridyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted quinoxalinyl group, and more specifically may be selected from hydrogen, deuterium, or substituents of Group I.

[Group I]

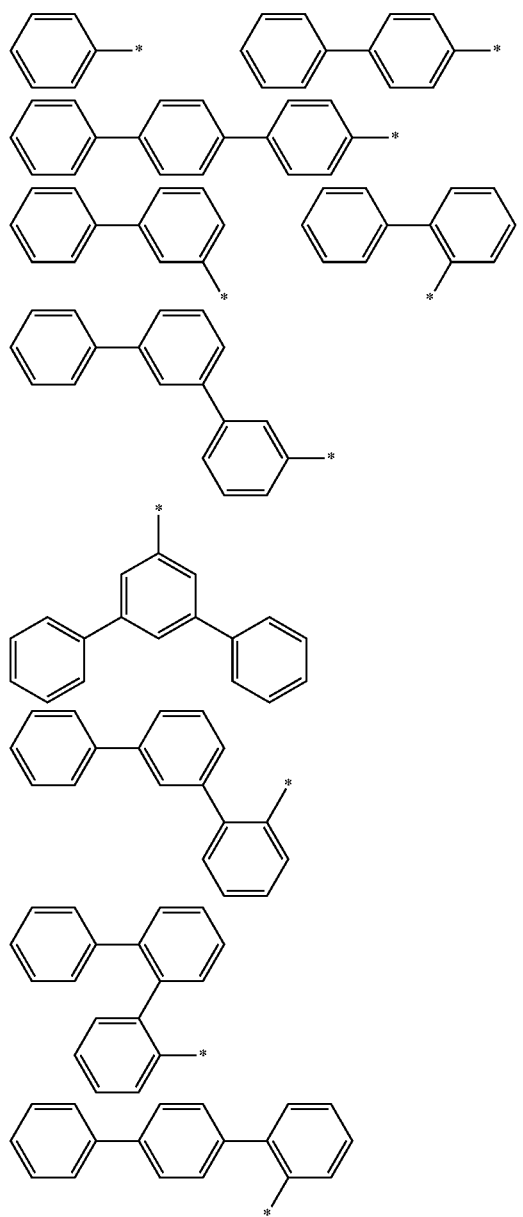
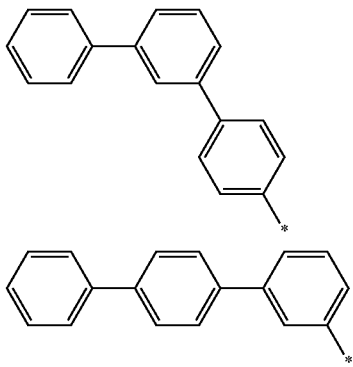
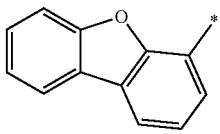
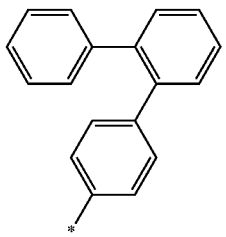
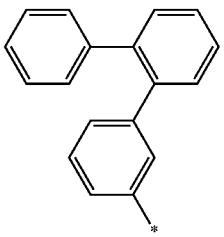
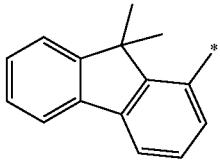
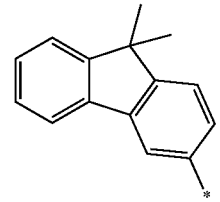
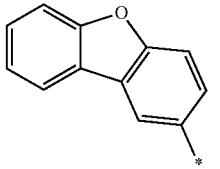
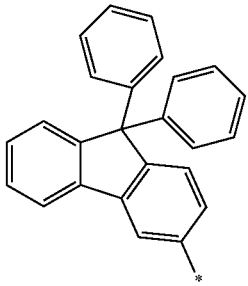
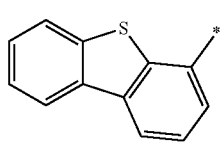
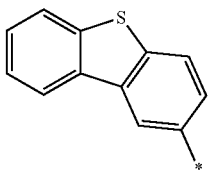
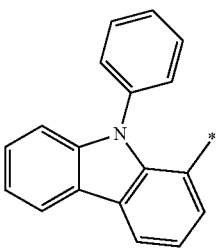

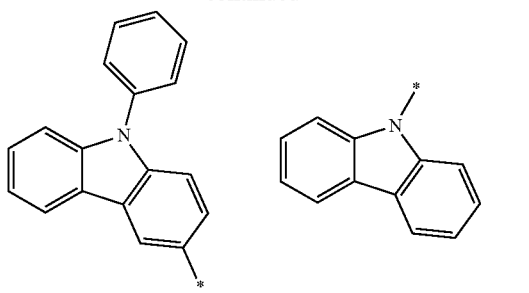
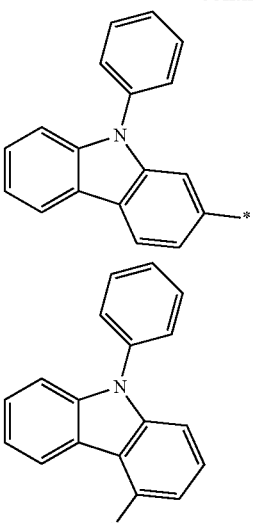
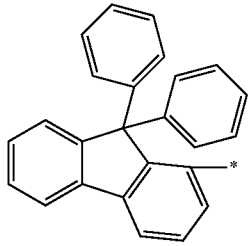
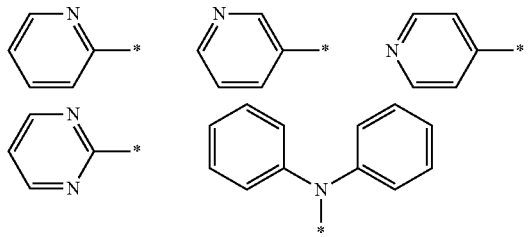
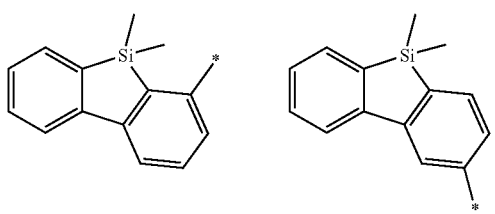
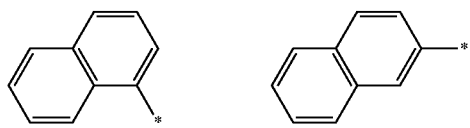
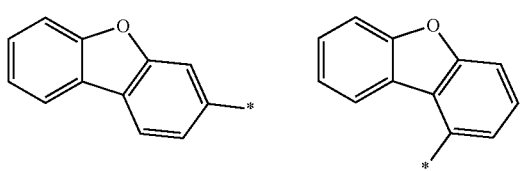
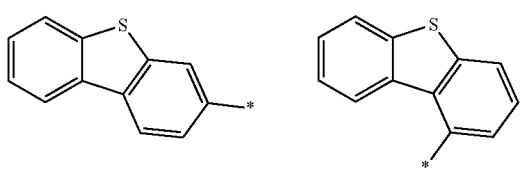

In Group I, * is a linking point.

In a specific example embodiment, $Ar^1$ to $Ar^4$ may independently be hydrogen, a phenyl group, a carbazolyl group, a dibenzofuranyl group, a dibenzothiophenyl group, or a fluorenyl group and $R^1$ to $R^4$ may independently be hydrogen or a phenyl group.

In a specific example embodiment of the present invention, Chemical Formula 1 may be represented by Chemical Formula 1-A, 1-B, or 1-C, $Ar^1$ to $Ar^4$ may independently be a phenyl group, a biphenyl group, a pyridyl group, a carbazolyl group, a dibenzofuranyl group, or a dibenzothiophenyl group, and $R^{a1}$ to $R^{a10}$ may independently be hydrogen, a phenyl group, or a biphenyl group.

The compound for an organic optoelectric device represented by Chemical Formula 1 may be, for example selected from compounds of Group 1, but is not limited thereto.

[Group 1]

1

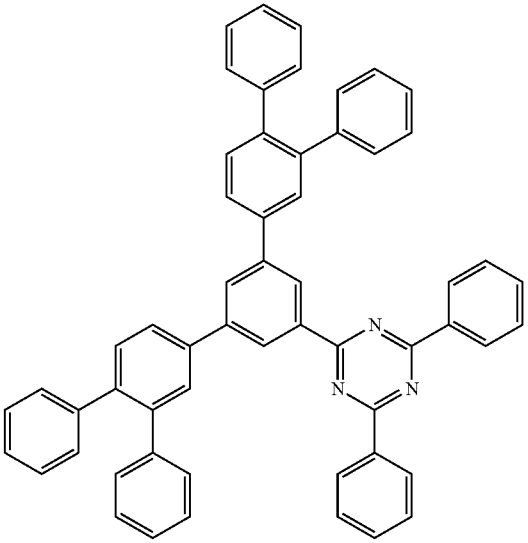

2
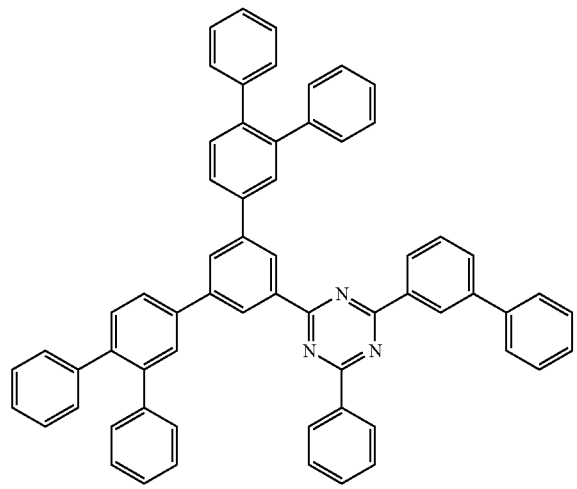
3
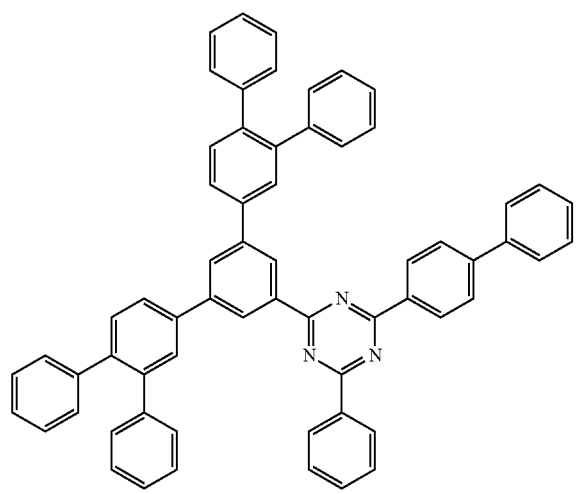
4
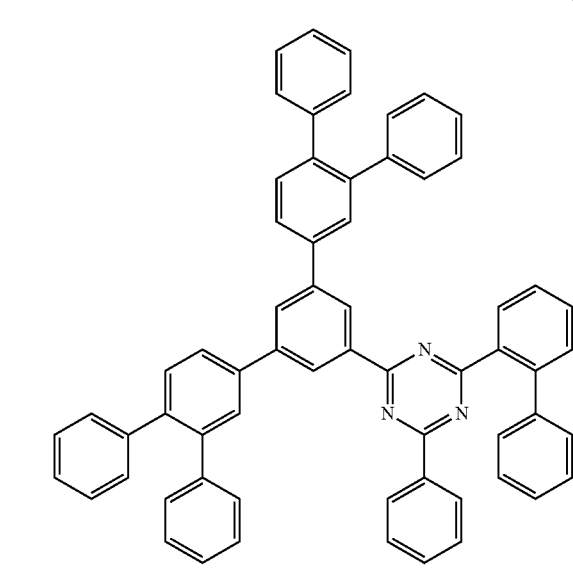
5
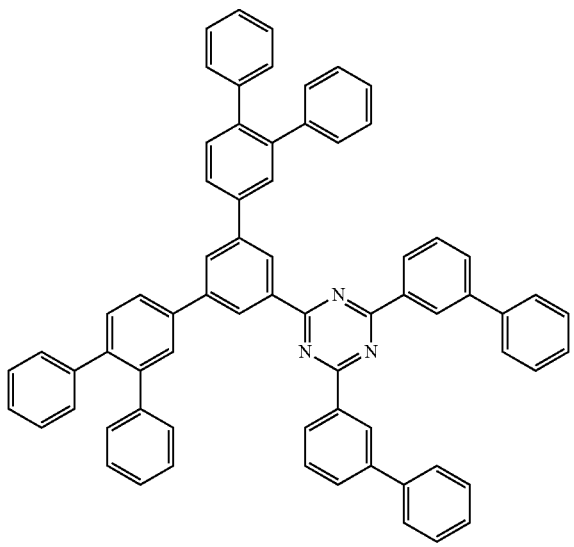
5
6
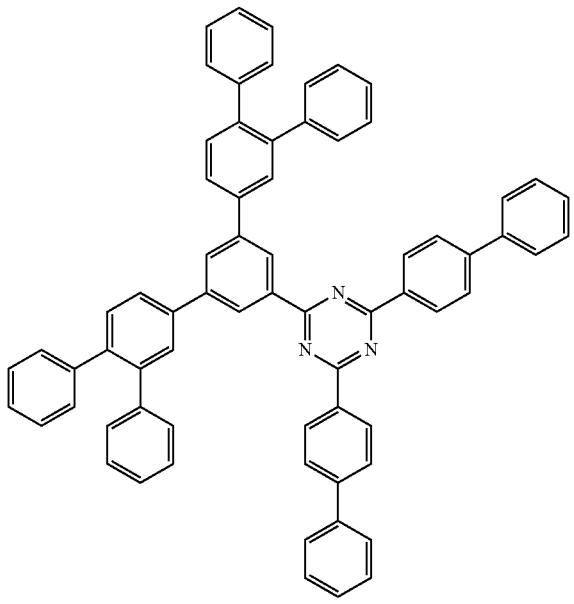

7
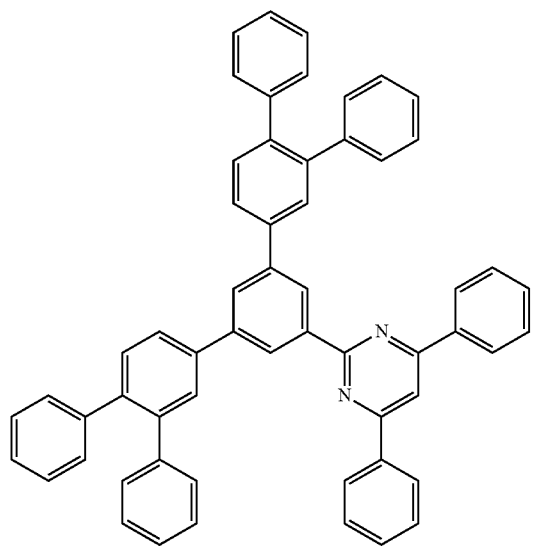
8
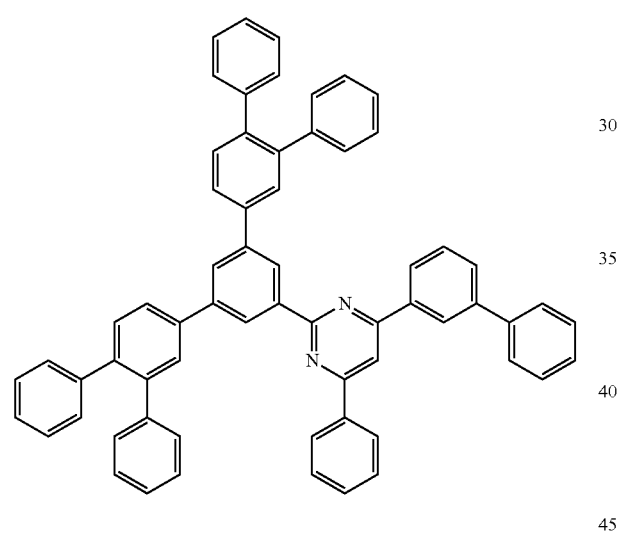
9
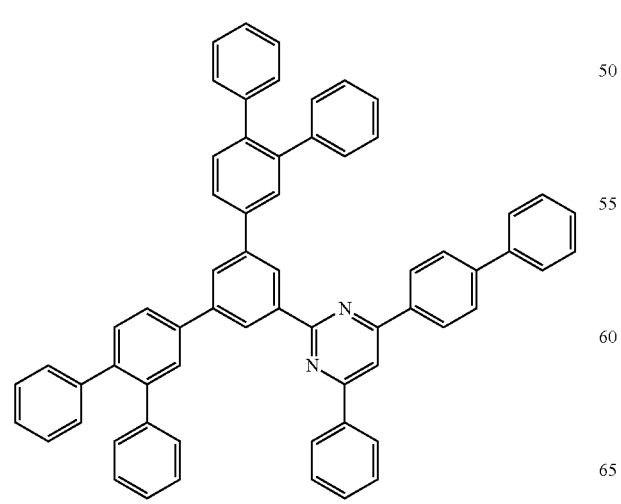
10
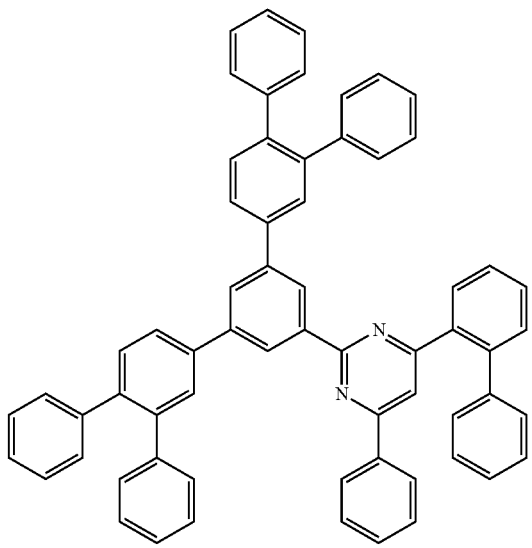
11
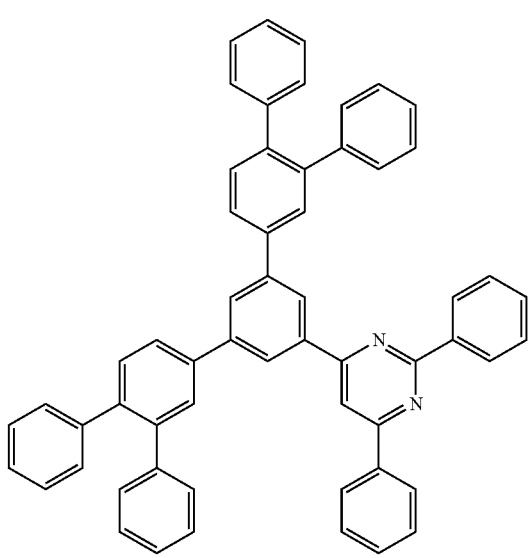
12
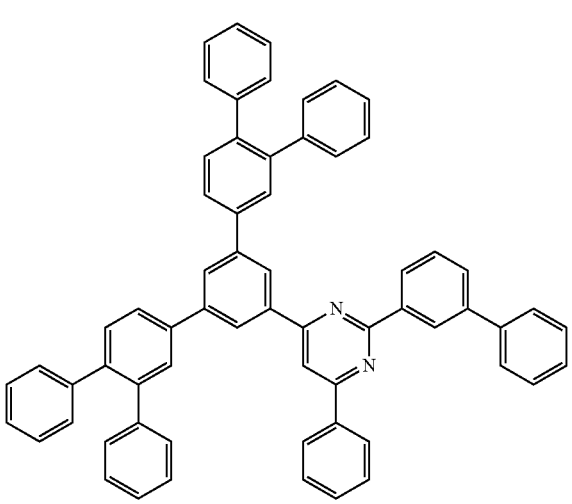

13
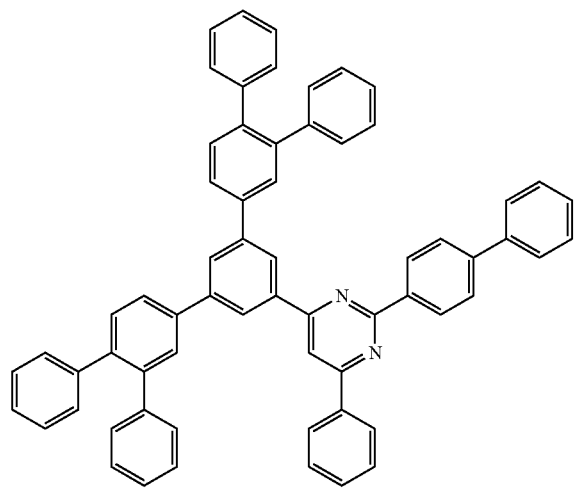
14
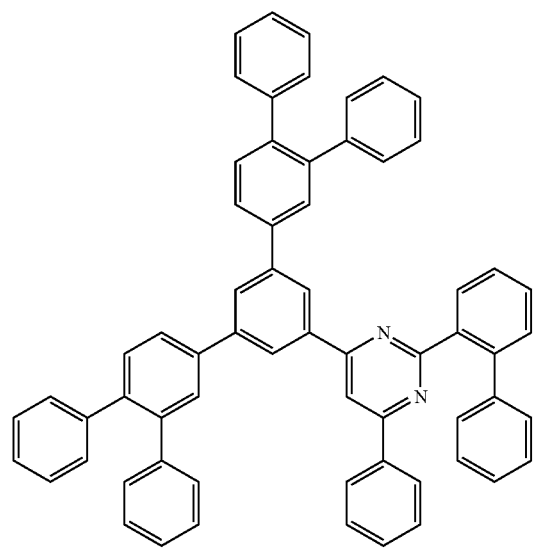
15
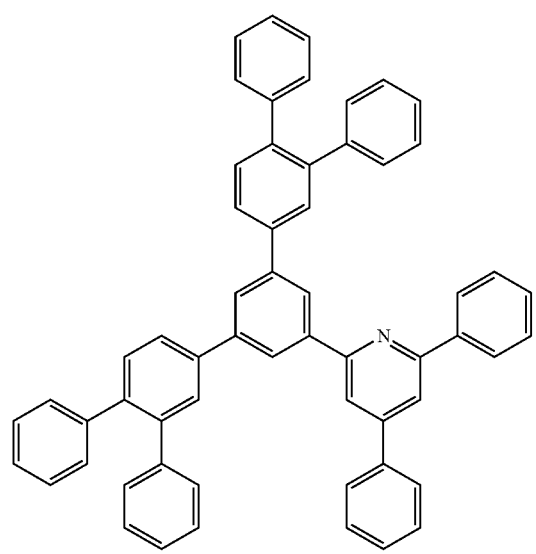
16
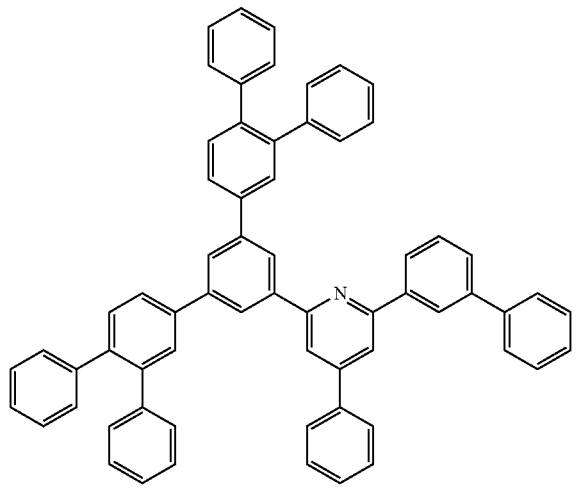
17
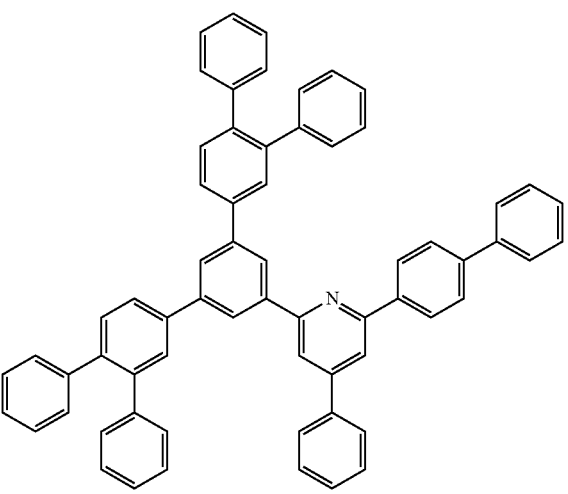
18
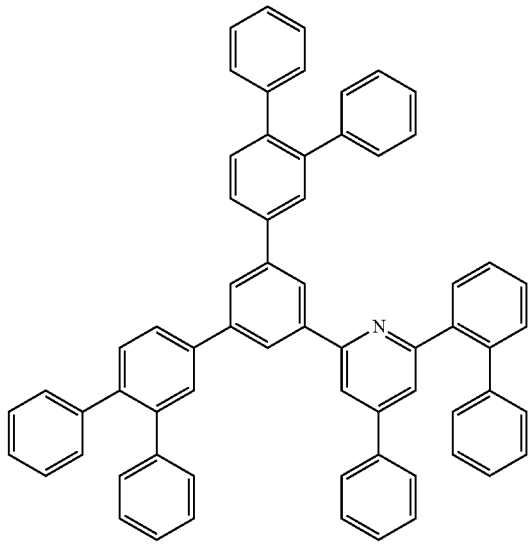

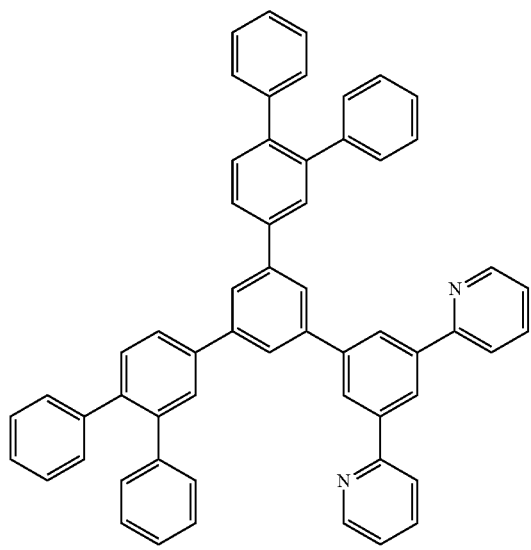
19
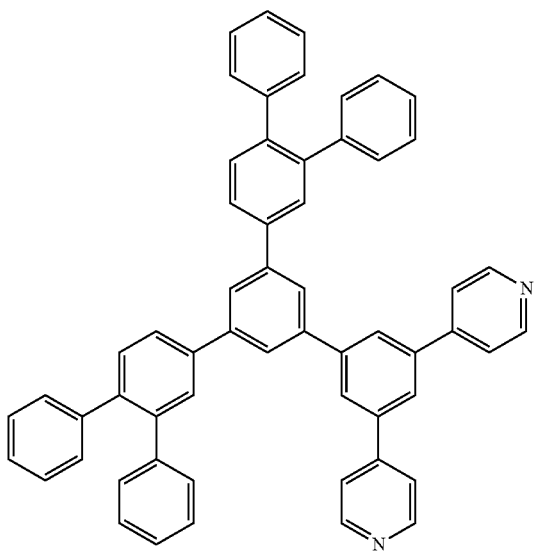
21
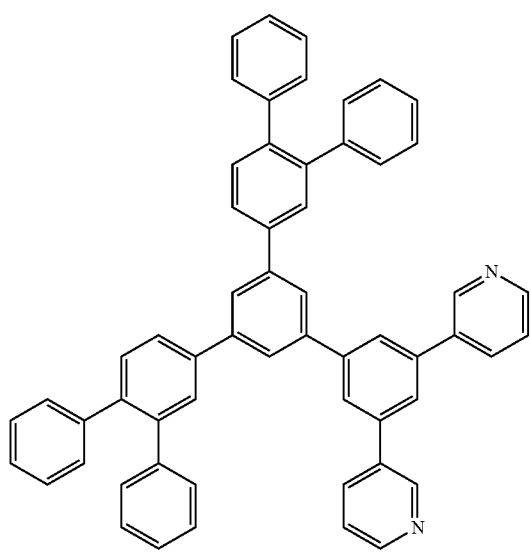
20

23
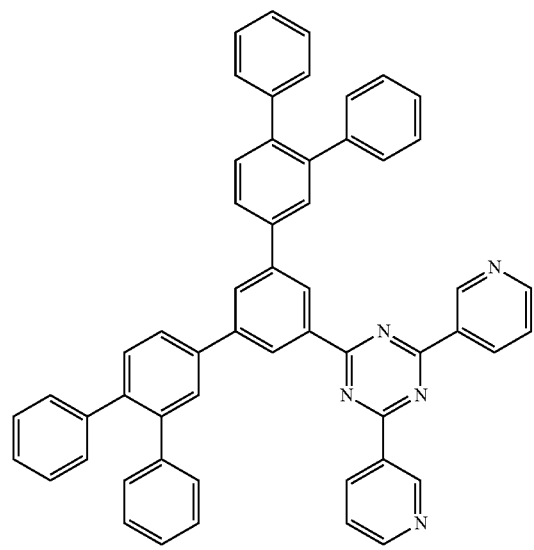
24
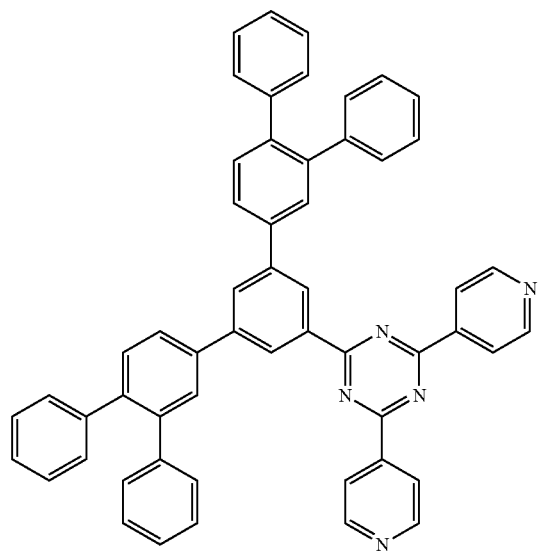
25
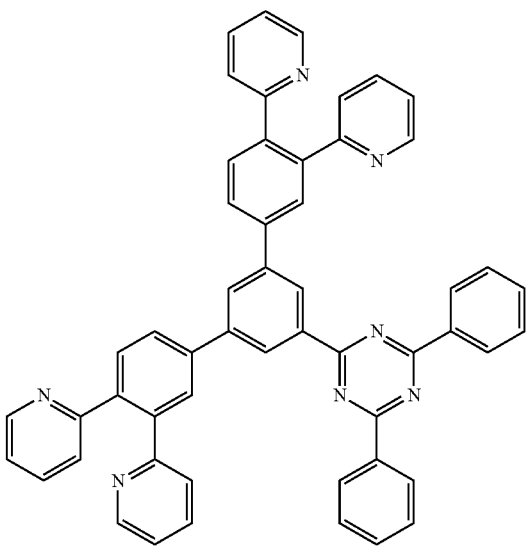
26
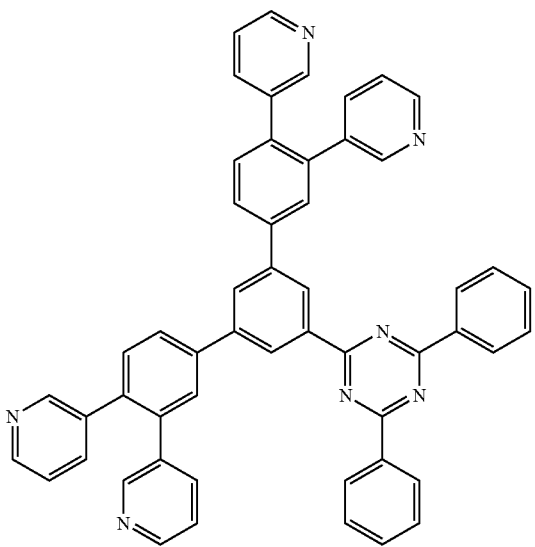

27
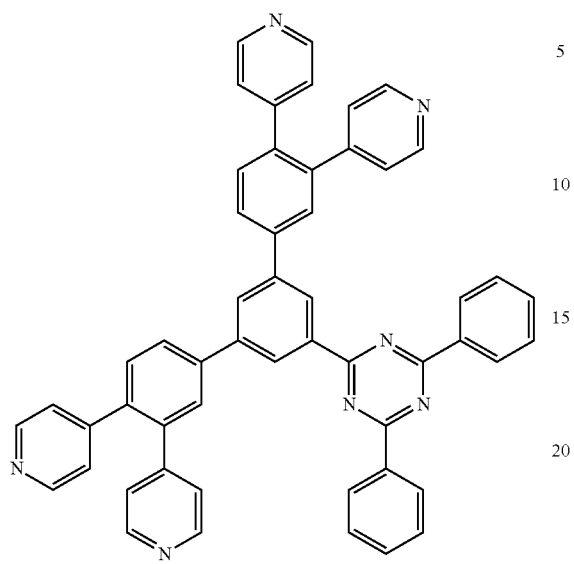
28
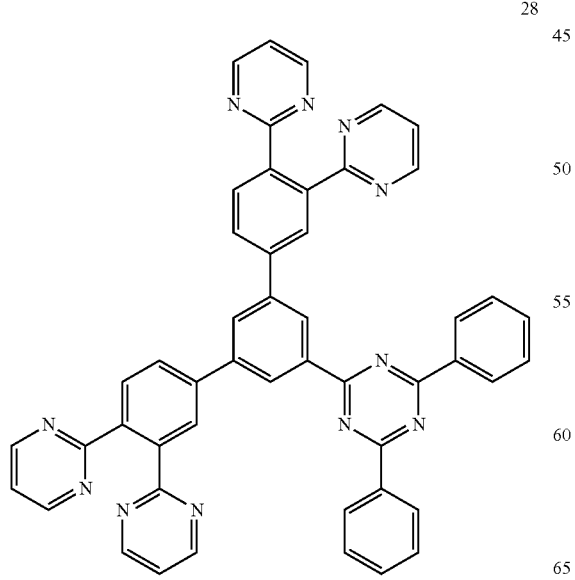
29
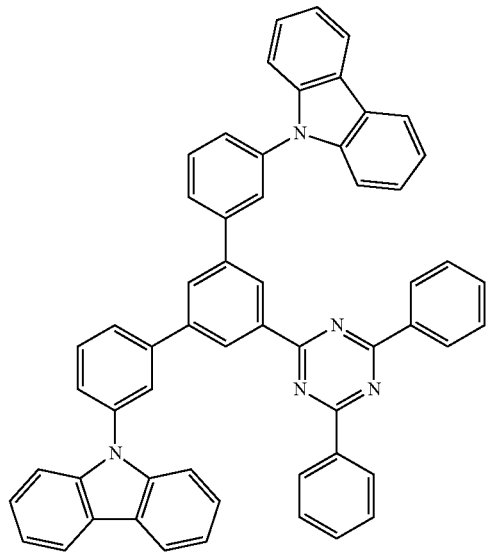
30
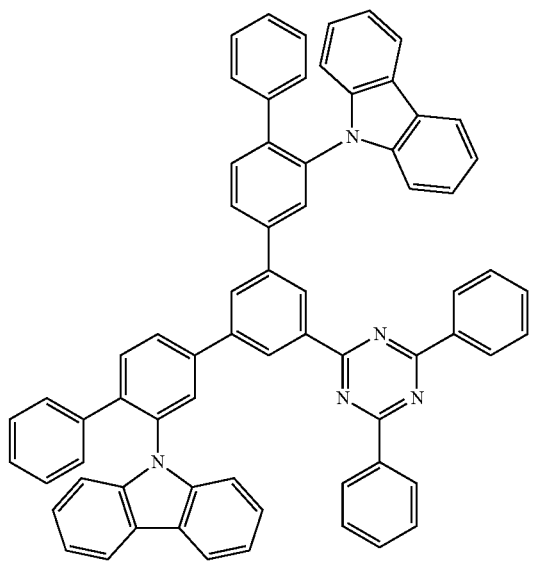

31
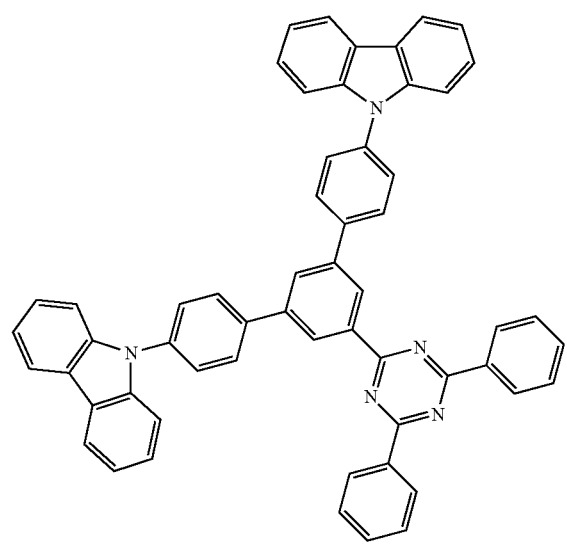
32
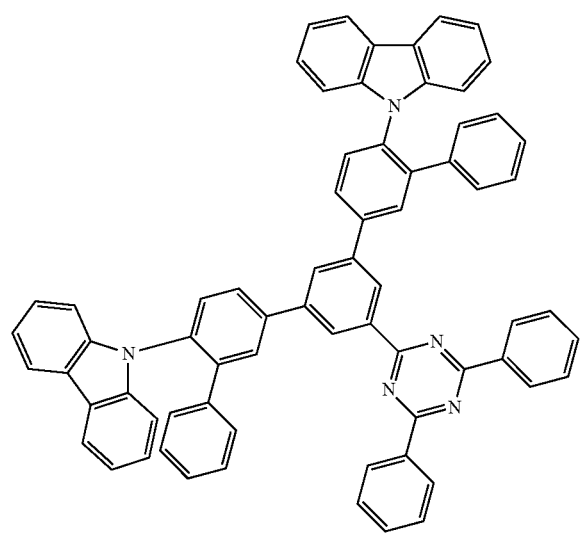
33
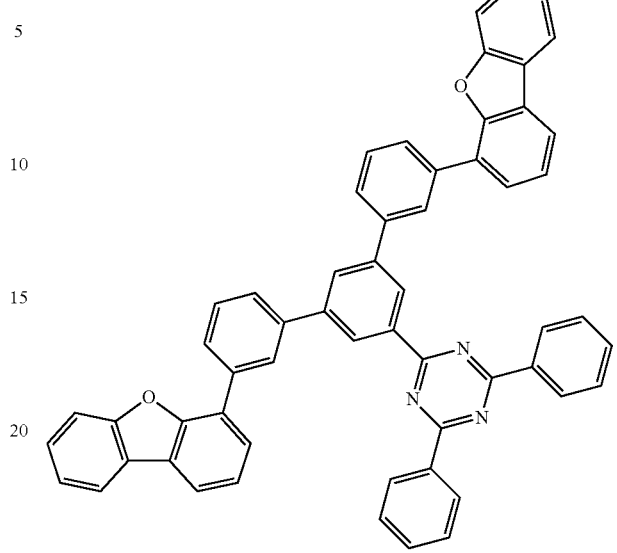
34
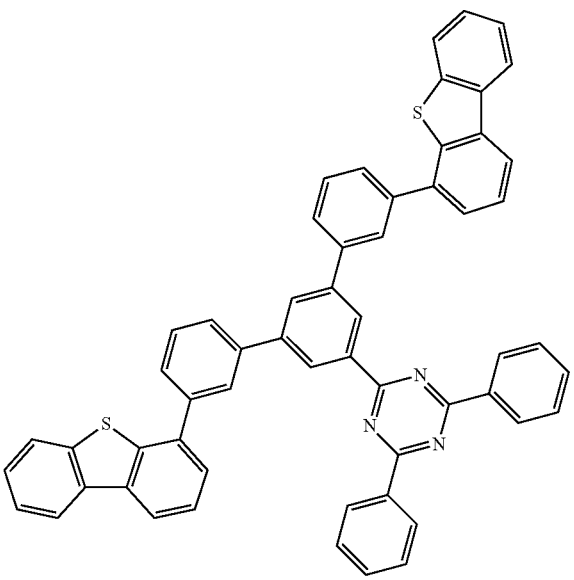

35
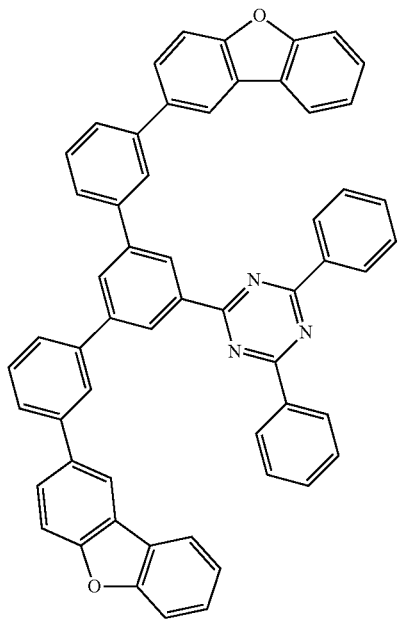
36
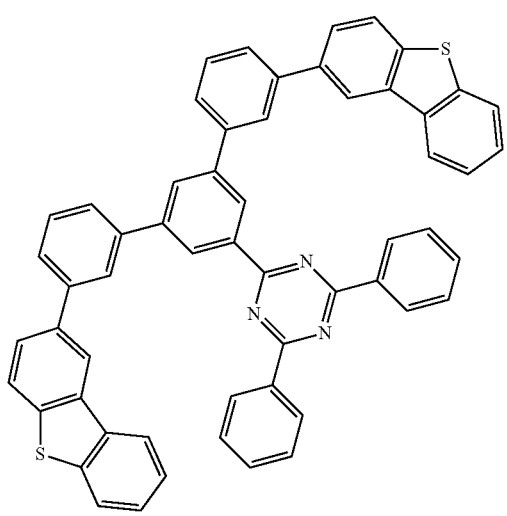
37
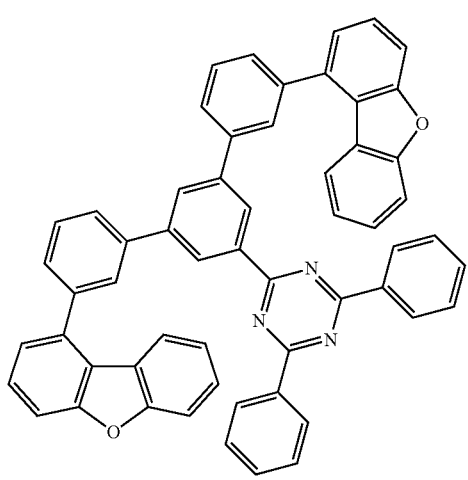
38
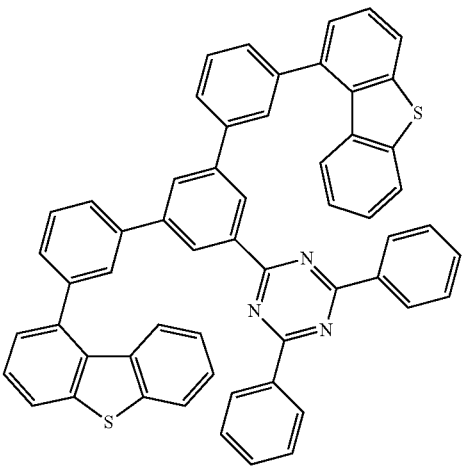
39
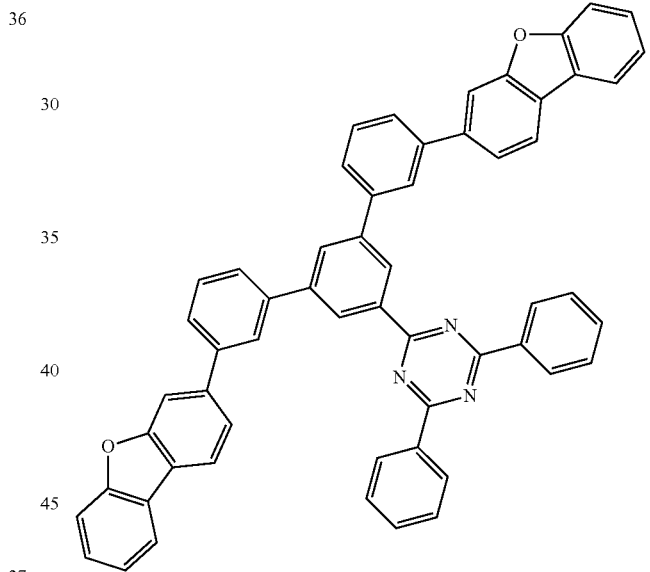
40
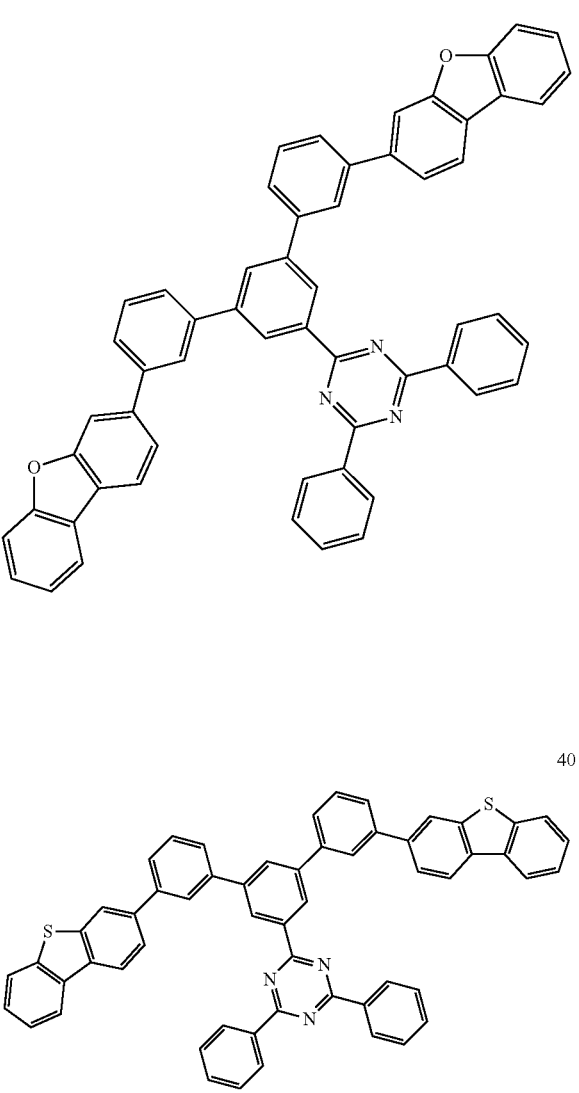

41
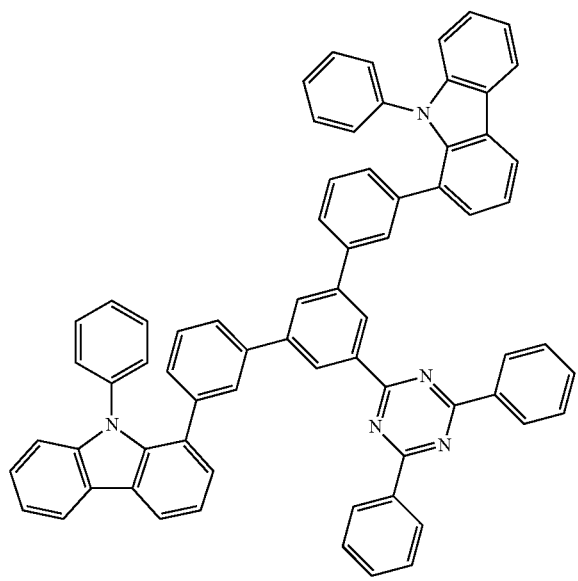
42
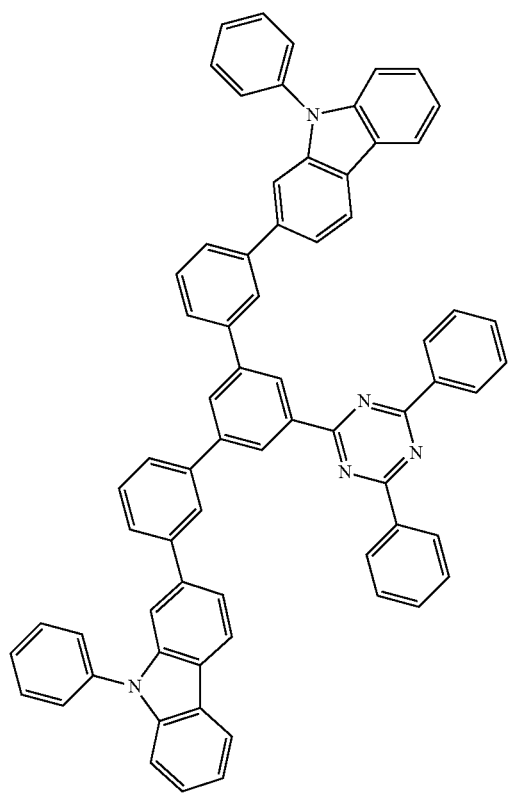
43
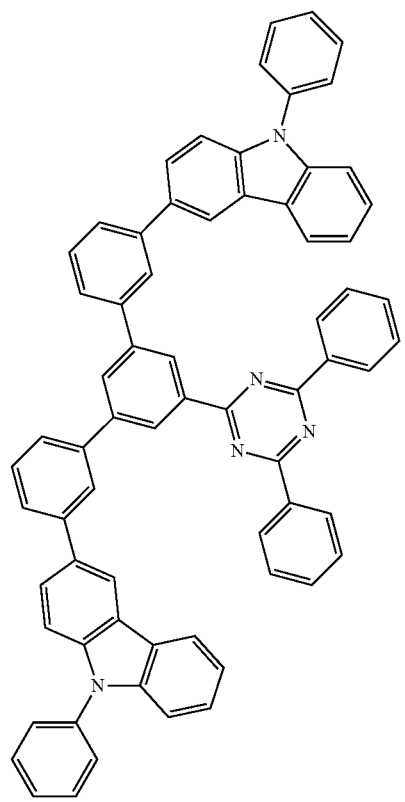
44
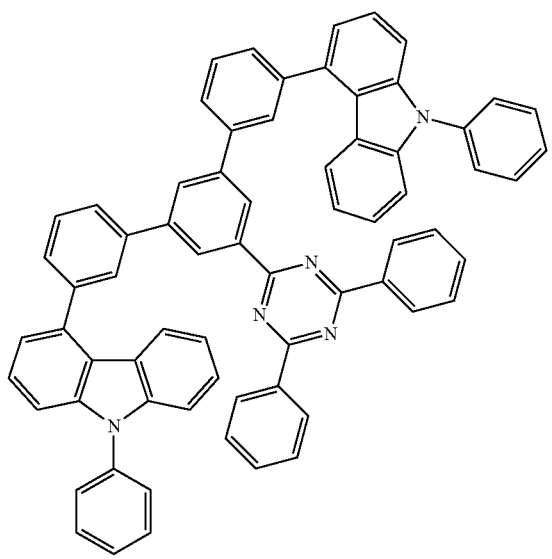

45
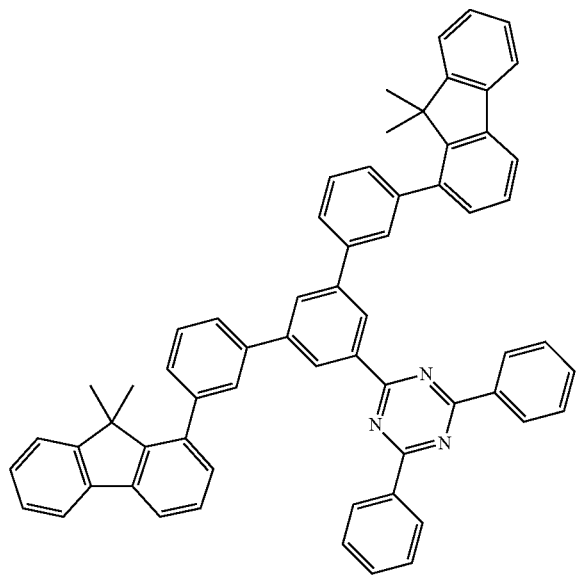
46
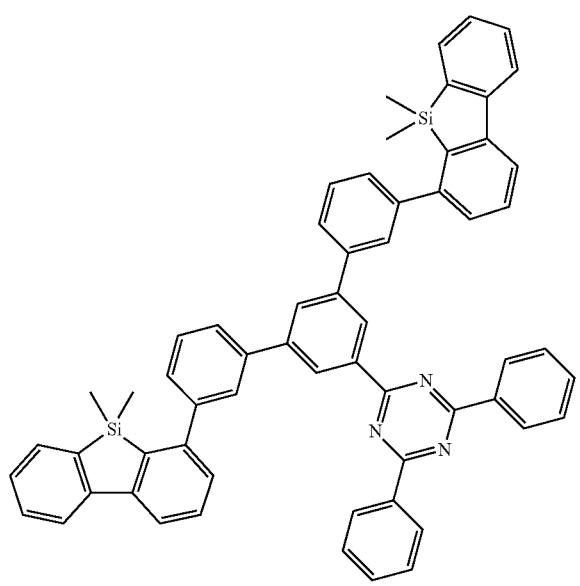
47
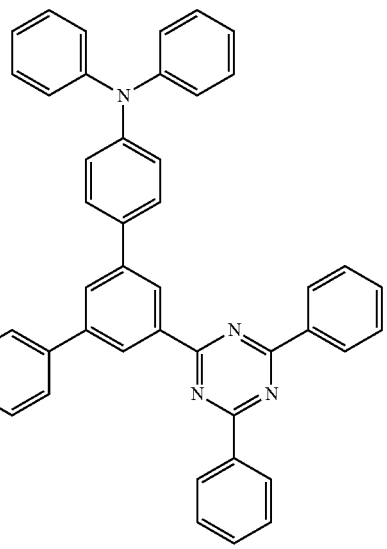
48
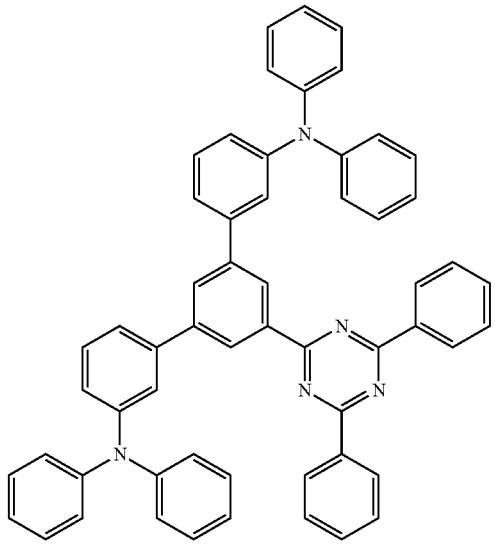
49
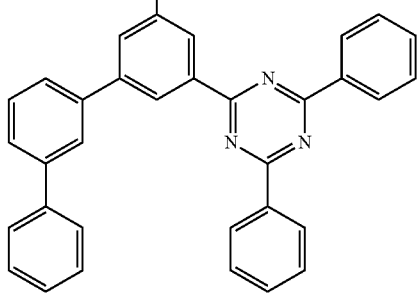

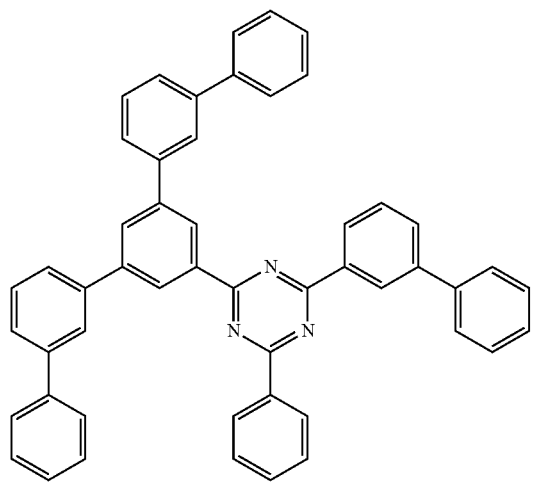
50
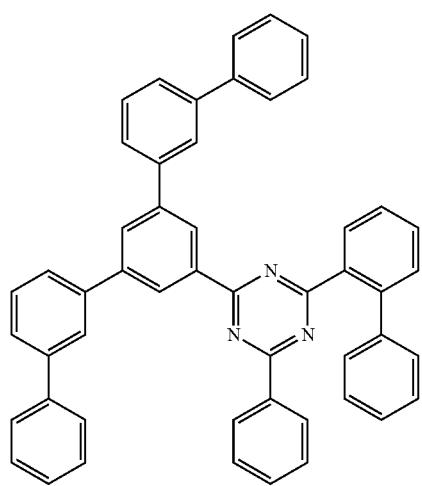
51
52
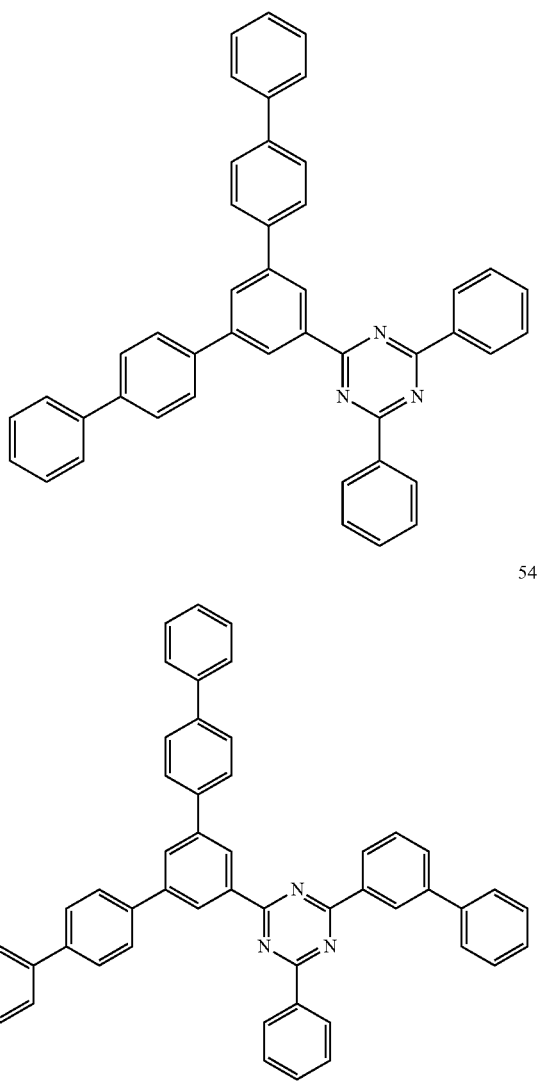
53
54
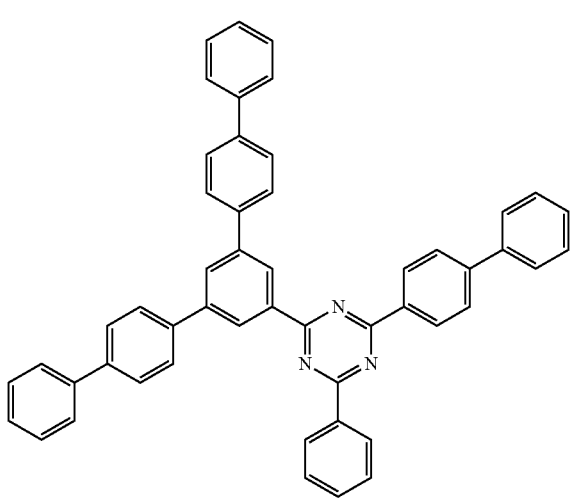
55

56
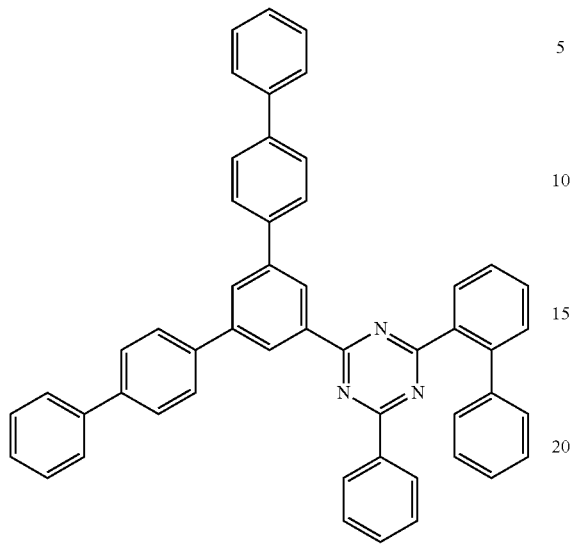
57
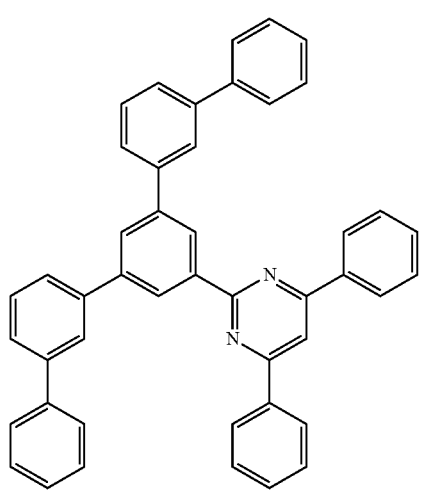
58
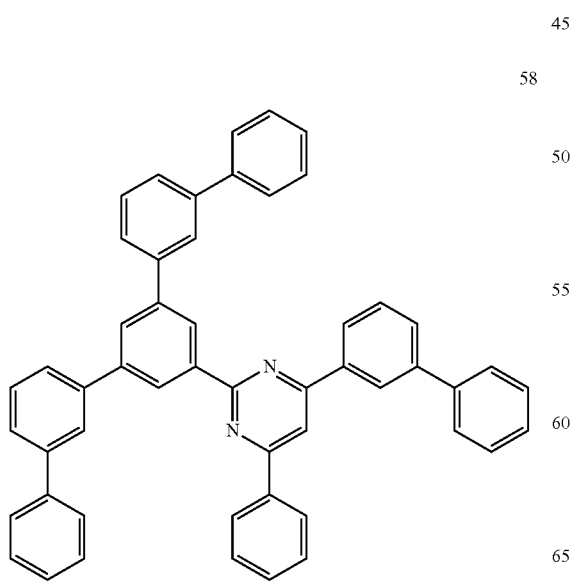
59
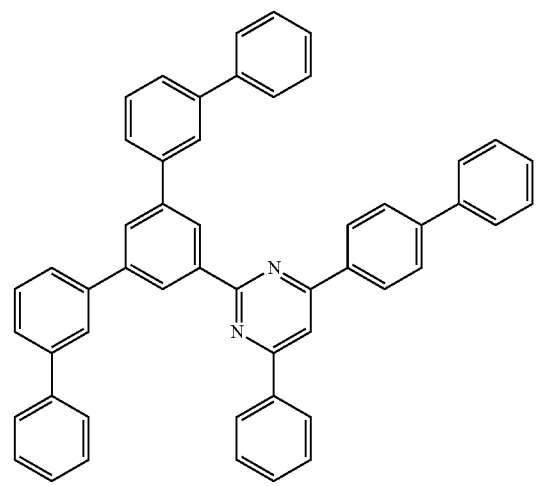
60
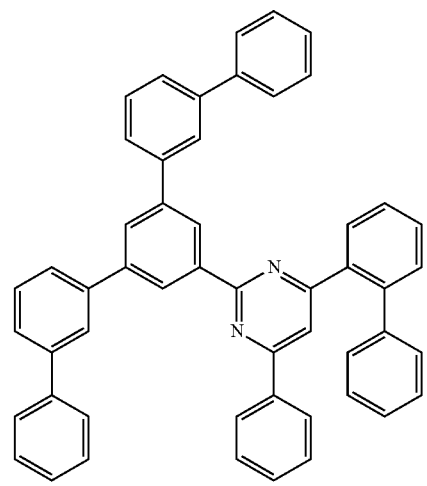
61
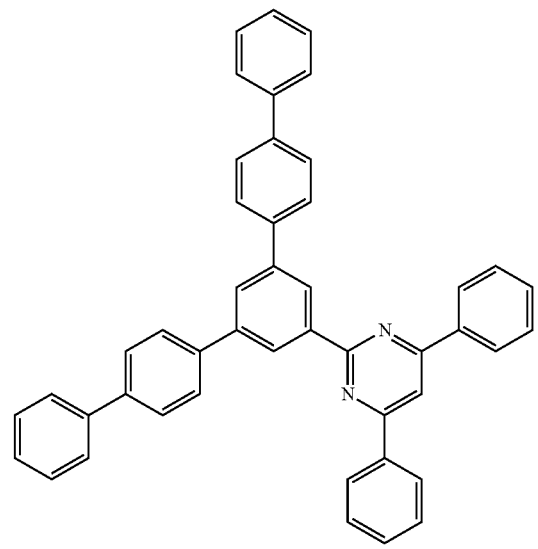

62
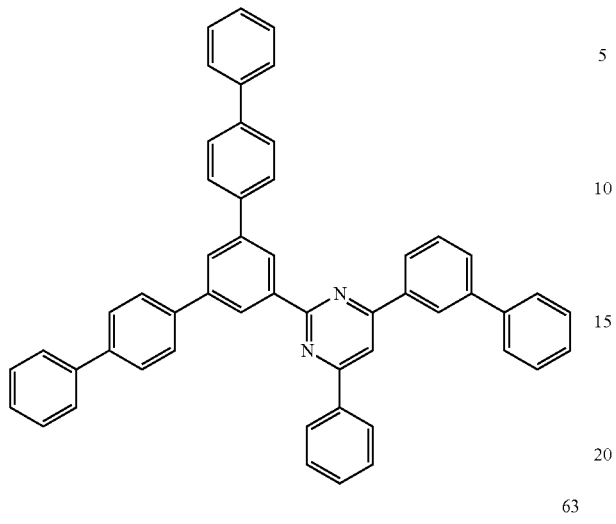
63
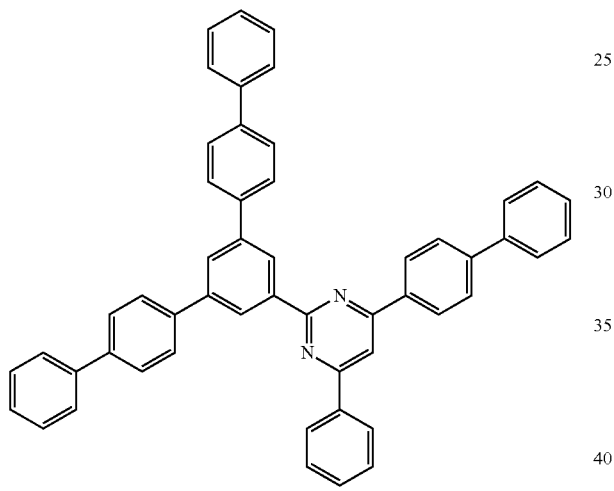
64
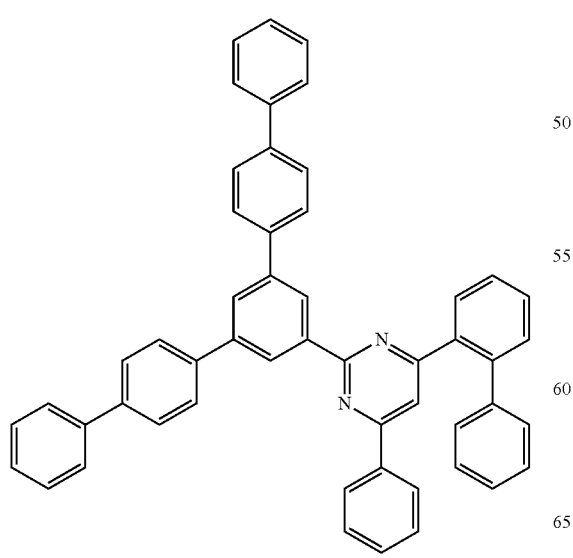
65
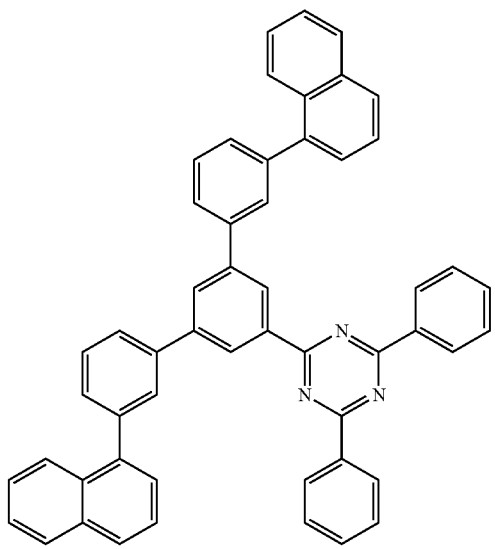
66
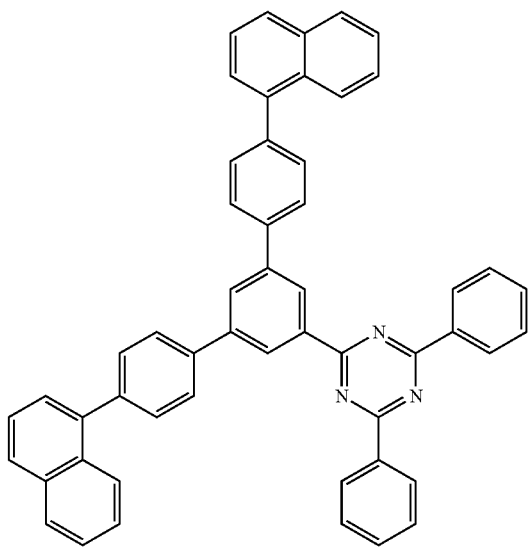

-continued

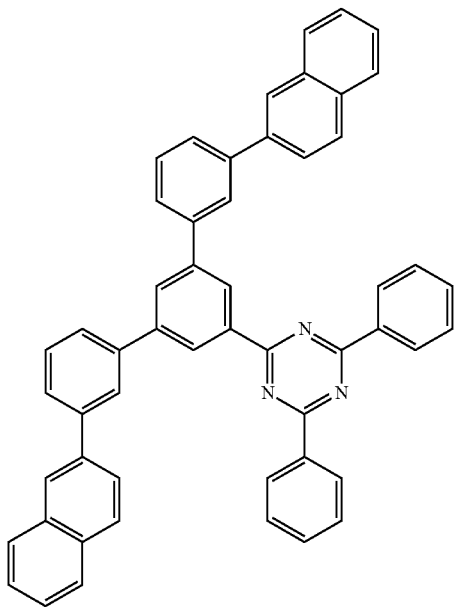
67

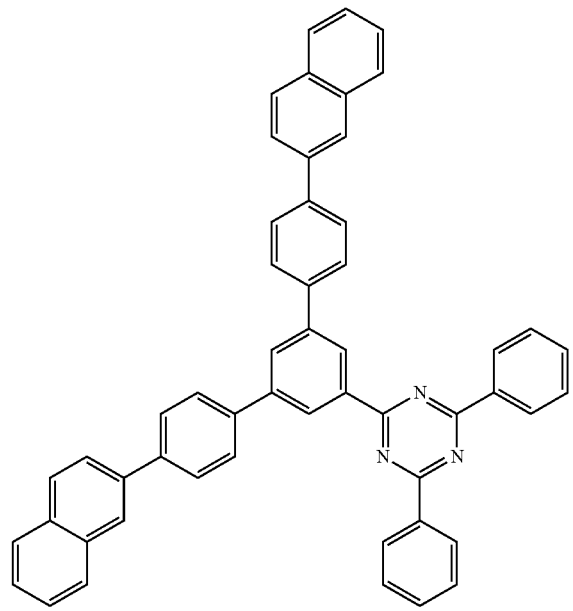
68

The first compound for an organic optoelectric device may be applied to an organic optoelectric device and may be applied to an organic optoelectric device alone or with other compound for an organic optoelectric device. When the compound for an organic optoelectric device is the other compound for an organic optoelectric device together, they may be applied in a form of a composition.

Hereinafter, one example of a composition for an organic optoelectric device including the first compound for an organic optoelectric device is described.

The composition for an organic optoelectric device according to another embodiment of the present invention includes the first compound for an organic optoelectric device; and at least one second compound for an organic optoelectric device represented by Chemical Formula 2.

[Chemical Formula 2]

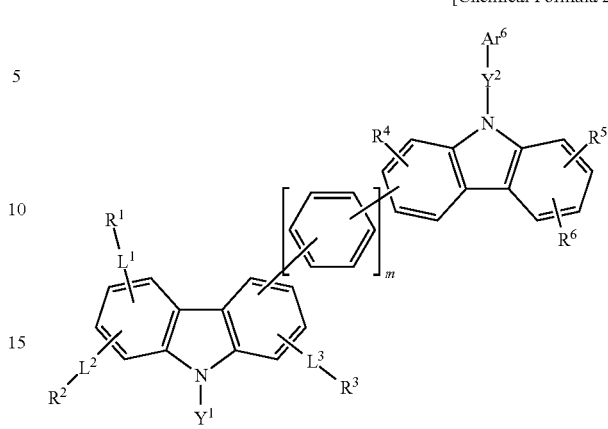

In Chemical Formula 2, $L^1$ to $L^3$, $Y^1$, and $Y^2$ are independently a single bond, a substituted or unsubstituted C6 to C30 arylene group, a substituted or unsubstituted C2 to C30 heteroarylene group, or a combination thereof, $Ar^5$ and $Ar^6$ are independently substituted or unsubstituted C6 to C30 aryl group, a substituted or unsubstituted C2 to C30 heterocyclic group, or a combination thereof, $R^1$ to $R^6$ are independently hydrogen, deuterium, a substituted or unsubstituted C1 to C20 alkyl group, a substituted or unsubstituted C6 to C30 aryl group, a substituted or unsubstituted C2 to C50 heterocyclic group, or a combination thereof, and m is an integer of 0 to 4.

$Ar^5$ and $Ar^6$ of Chemical Formula 2 may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted fluorenyl group, a substituted or unsubstituted pyridinyl group, a substituted or unsubstituted quinazolyl group, a substituted or unsubstituted isoquinazolyl group, a substituted or unsubstituted dibenzothiophenyl group, a substituted or unsubstituted dibenzofuranyl group, or a combination thereof.

In an example embodiment of the present invention, $L^1$ to $L^3$, $Y^1$, and $Y^2$ of Chemical Formula 2 may independently be a single bond, a substituted or unsubstituted C6 to C18 arylene group, a substituted or unsubstituted C2 to C20 heteroarylene group, or a combination thereof, $Ar^5$ and $Ar^6$ are independently substituted or unsubstituted C6 to C30 aryl group, a substituted or unsubstituted C2 to C30 heterocyclic group, or a combination thereof, $R^1$ to $R^6$ are independently hydrogen, deuterium, a substituted or unsubstituted C1 to C20 alkyl group, a substituted or unsubstituted C6 to C30 aryl group, a substituted or unsubstituted C2 to C50 heterocyclic group, or a combination thereof, and m is an integer of 0 to 2.

In an example embodiment of the present invention, m may be 0 or 1.

In an example embodiment of the present invention, $L^1$ to $L^3$, $Y^1$ and $Y^2$ may independently be a single bond or a substituted or unsubstituted C6 to C18 arylene group.

In a specific example embodiment, Chemical Formula 2 may be one of structures of Group II and *—$Y^1$—$Ar^5$ and *—$Y^2$—$Ar^6$ may be one of substituents of Group III.

[Group II]
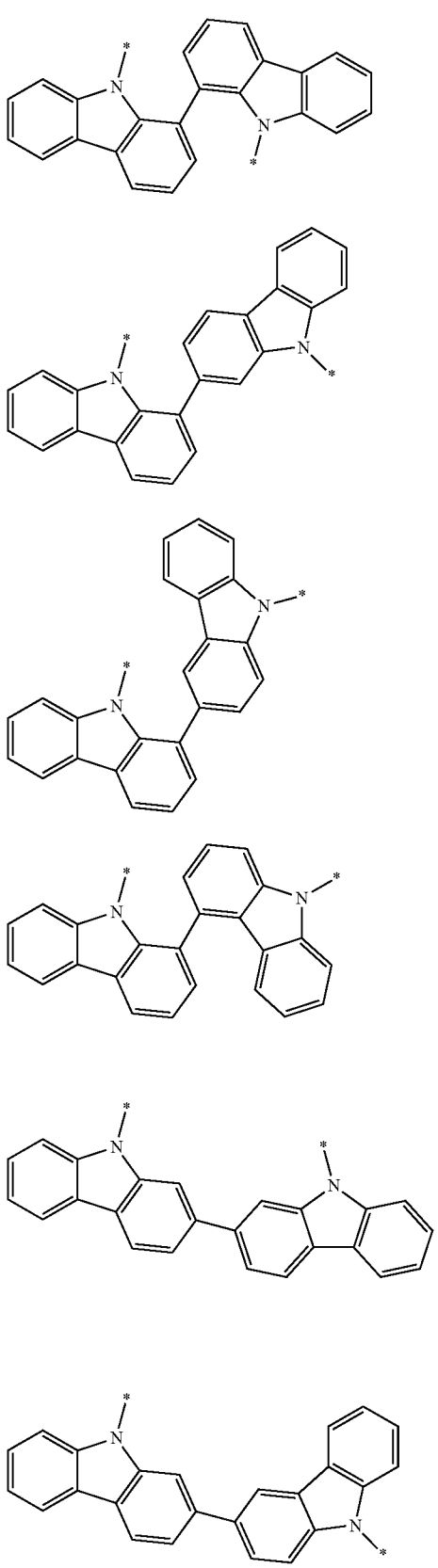
C-1
C-2
C-3
C-4
C-5
C-6
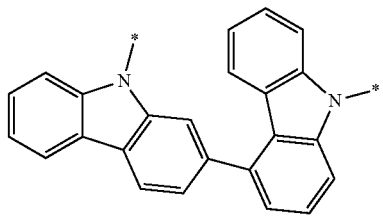
C-7
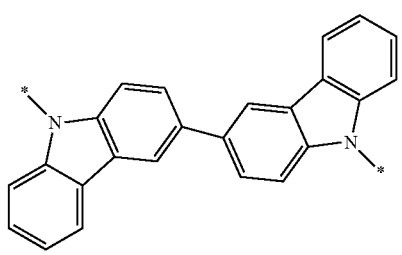
C-8
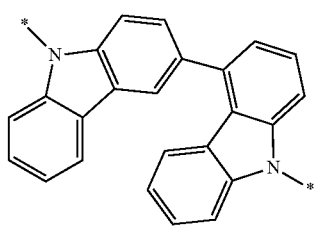
C-9
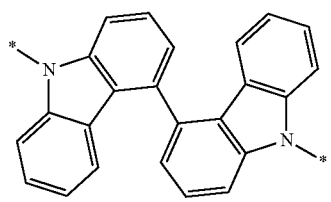
C-10
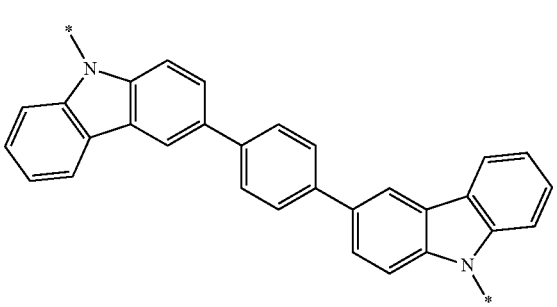
c-11
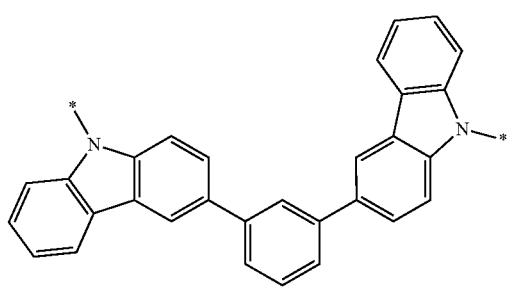
c-12 c-13
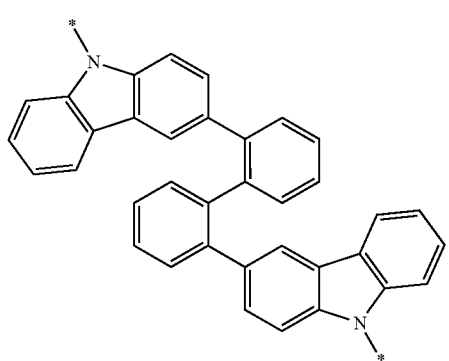
c-14
c-15
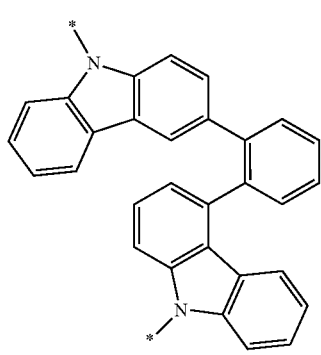
[Group III]
B-1
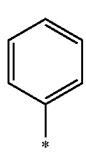
B-2
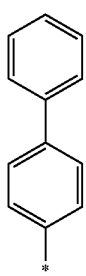
B-3
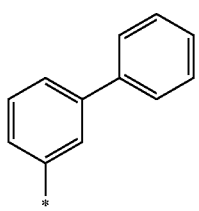
B-4
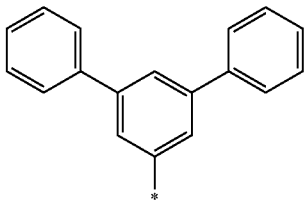
B-5
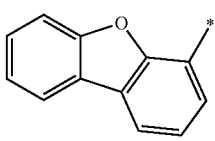
B-6
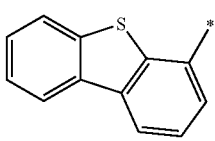
B-7
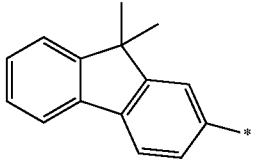
B-8
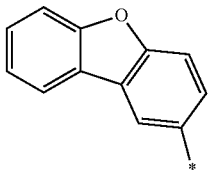
B-9
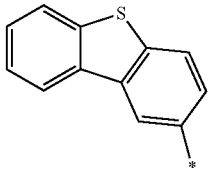
B-10
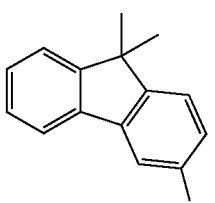

-continued
B-11
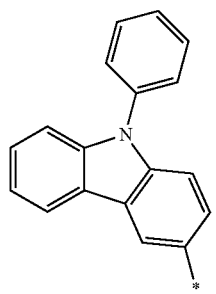
B-12
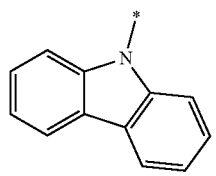
B-13
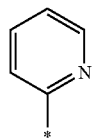
B-14
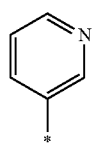
B-15
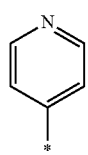
B-16
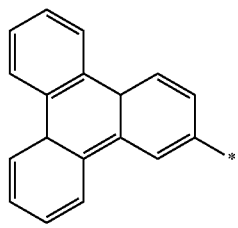
B-17
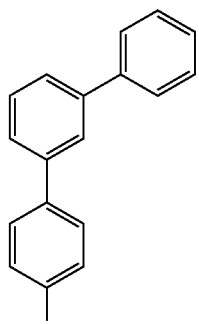
B-18
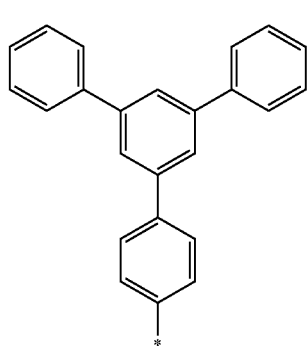
In Group II and Group III, * is a linking point.
The second compound for an organic optoelectric device represented by Chemical Formula 2 may be, for example compounds of Group 2, but is not limited thereto.
[Group 2]
[B-1]
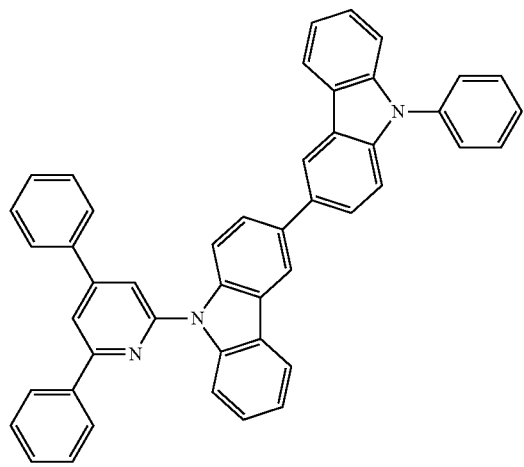
[B-2]
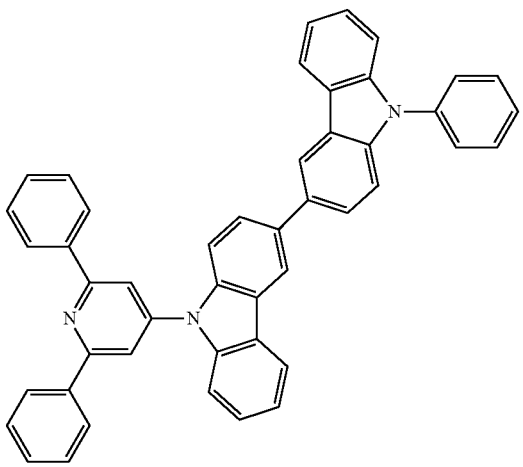

-continued
[B-3]
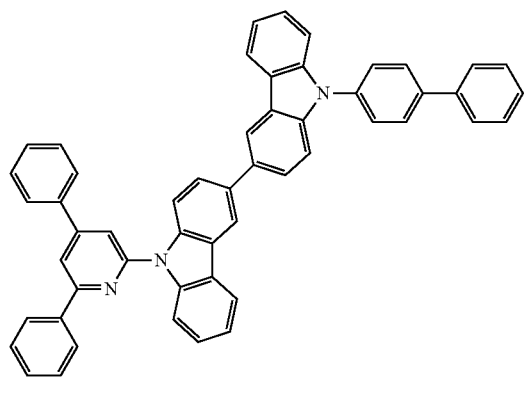
[B-4]
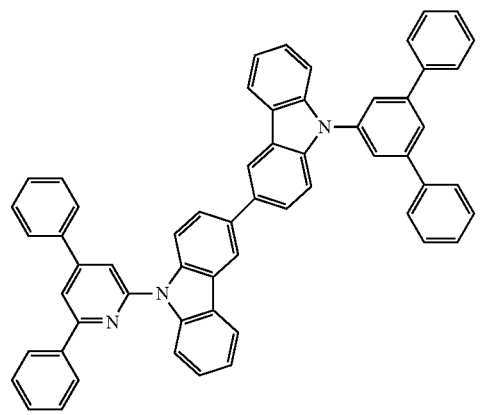
[B-5]
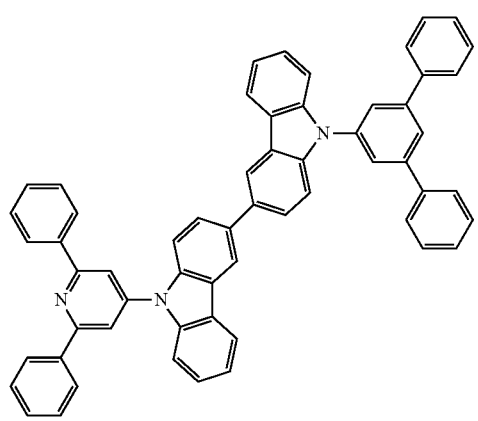
[B-6]
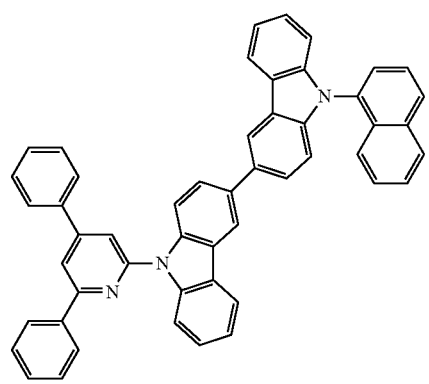
[B-7]
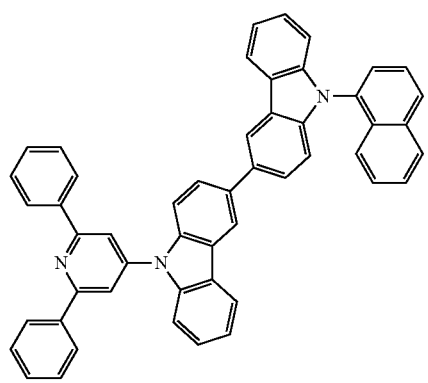
[B-8]
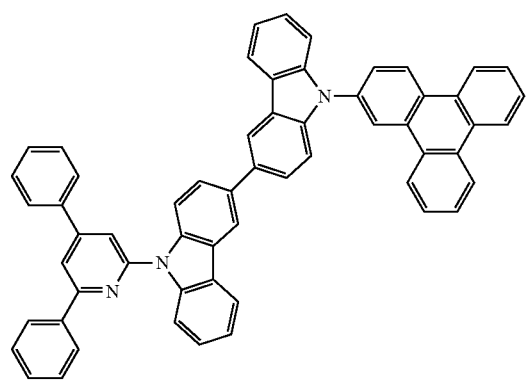

[B-9]
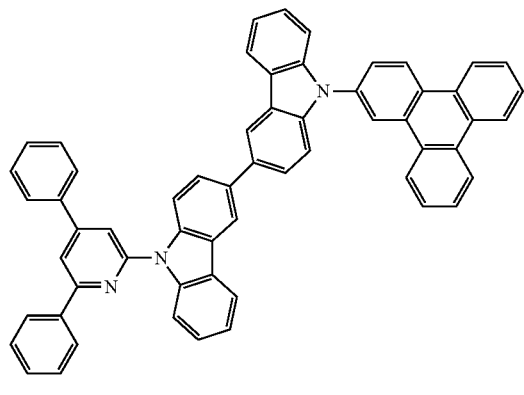
[B-10]
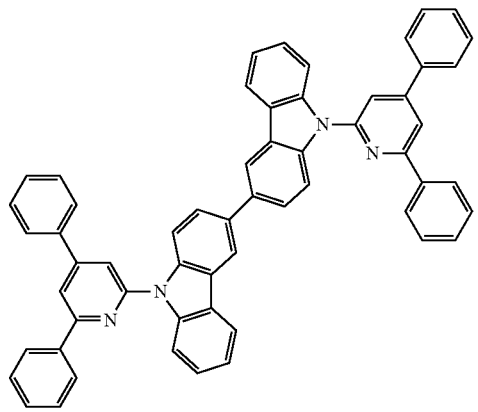
[B-11]
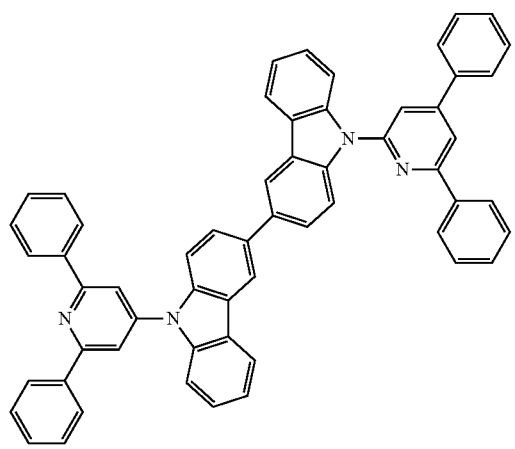
[B-12]
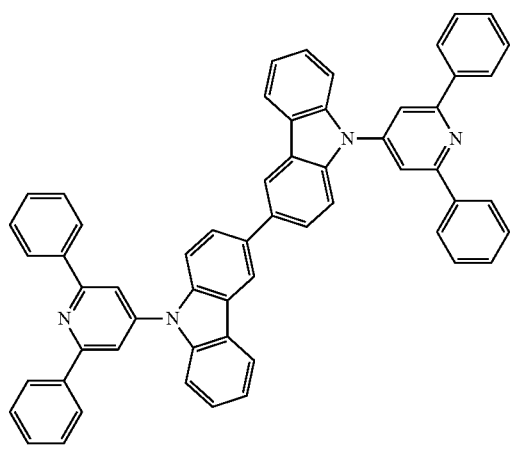
[B-13]
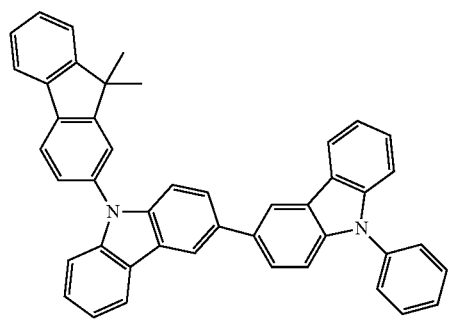
[B-14]
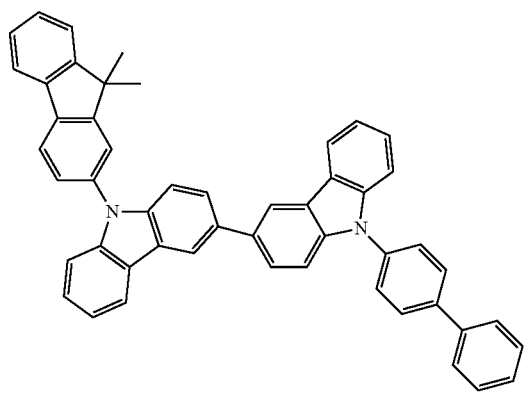

[B-15]
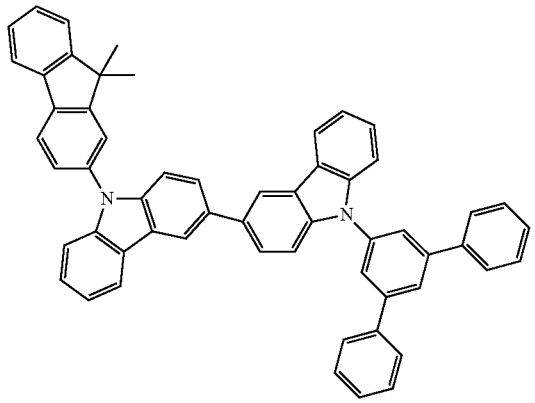
[B-16]
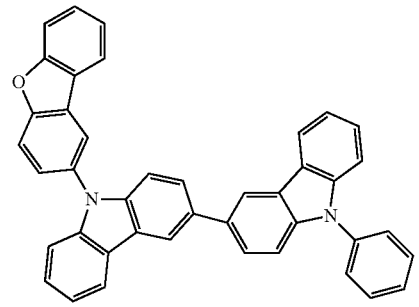
[B-17]
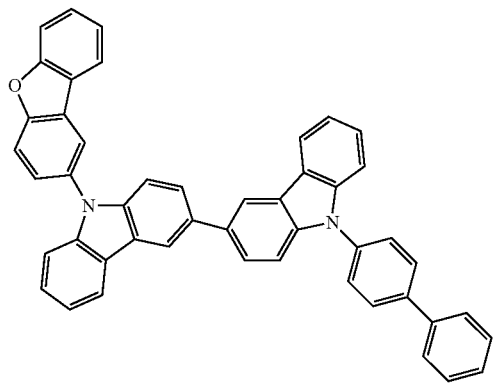
[B-18]
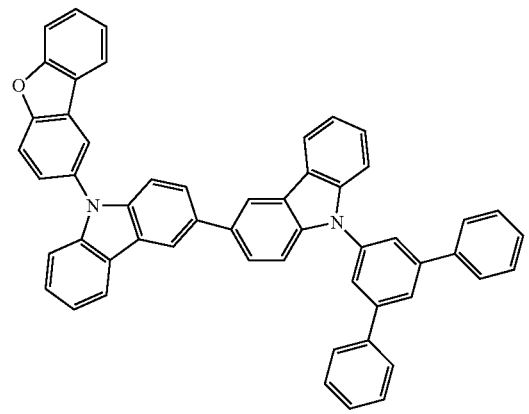
[B-19]
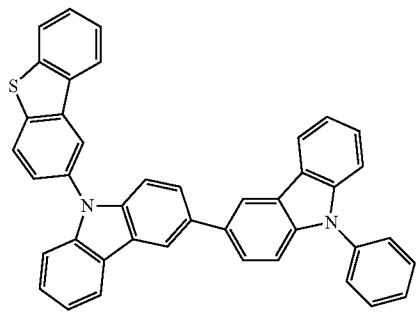
[B-20]
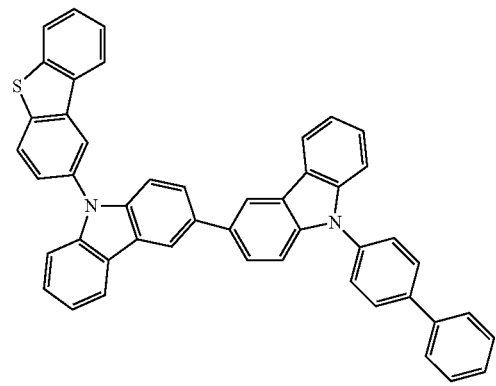

-continued
[B-21]
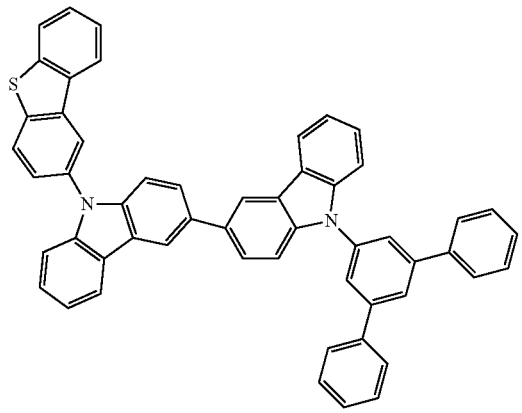
[B-22]
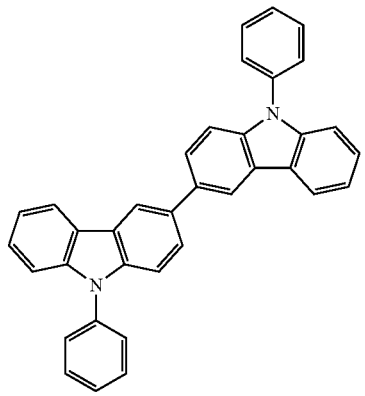
[B-23]
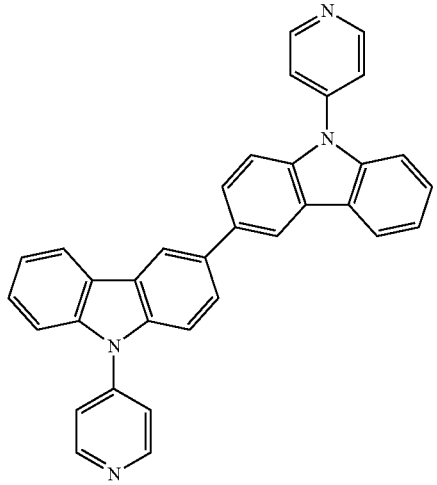
[B-24]
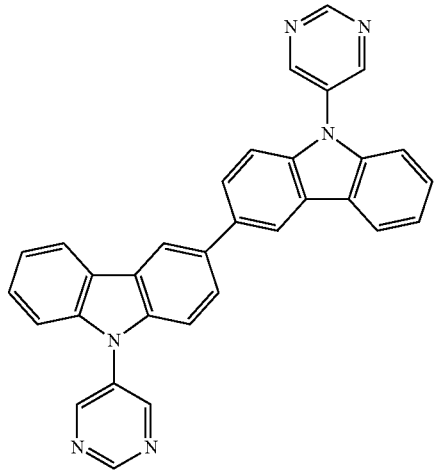
[B-25]
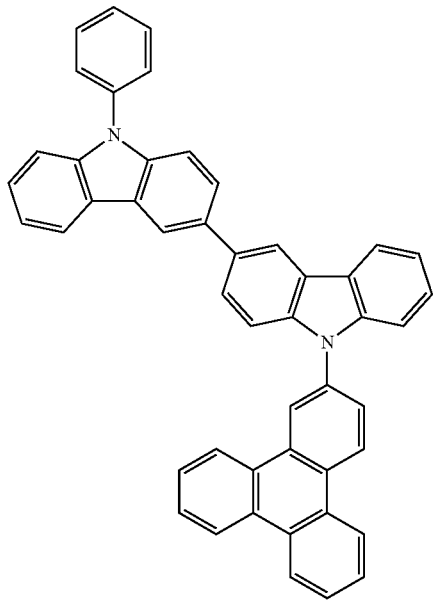
[B-26]
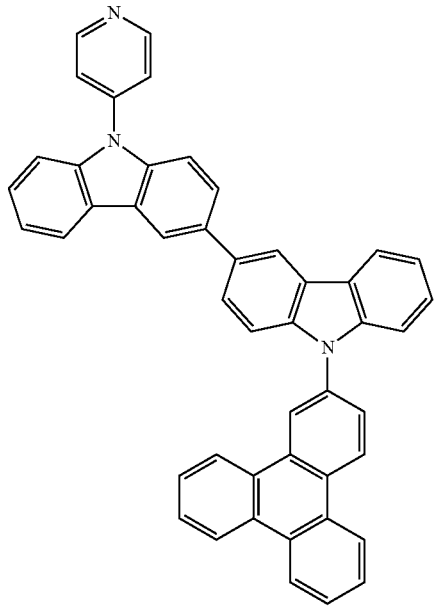

[B-27]
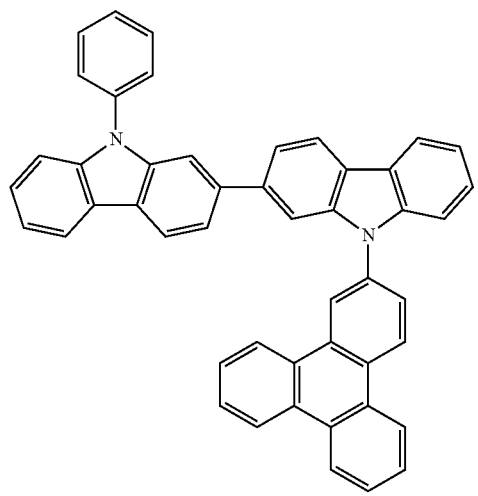
[B-28]
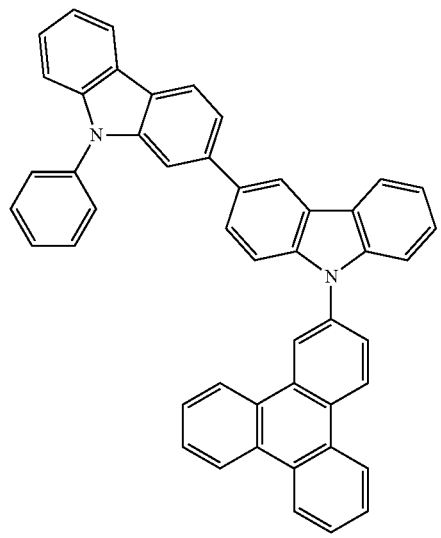
[B-29]
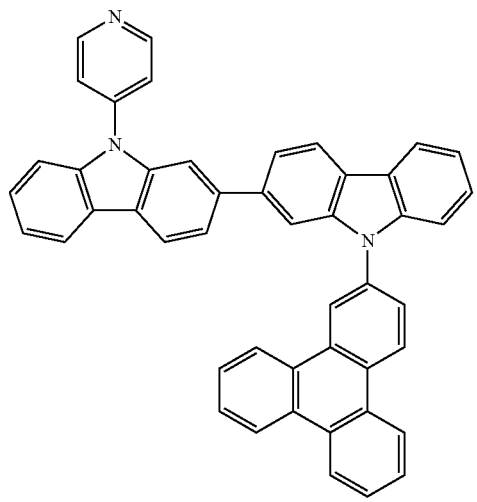
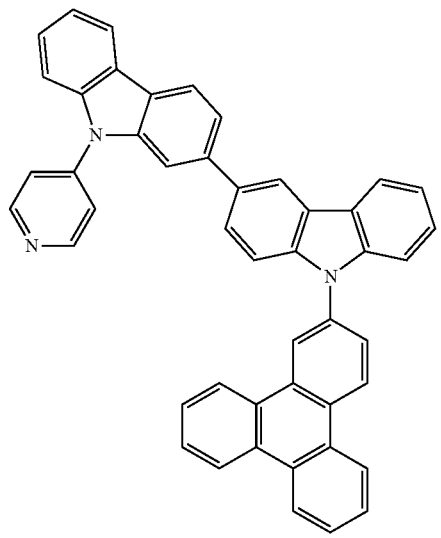

[B-30]
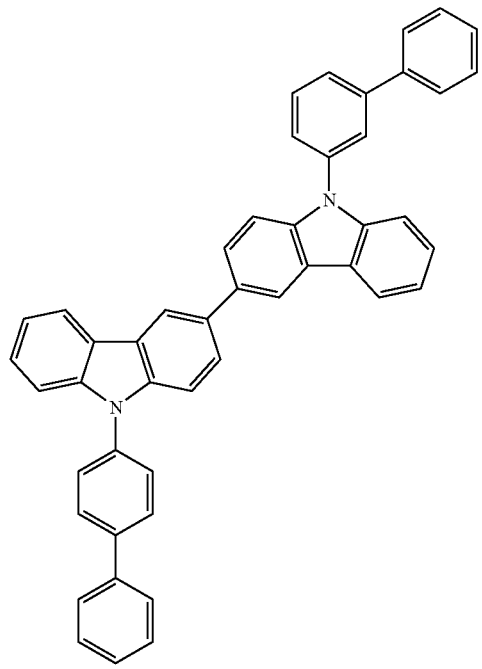
[B-31]
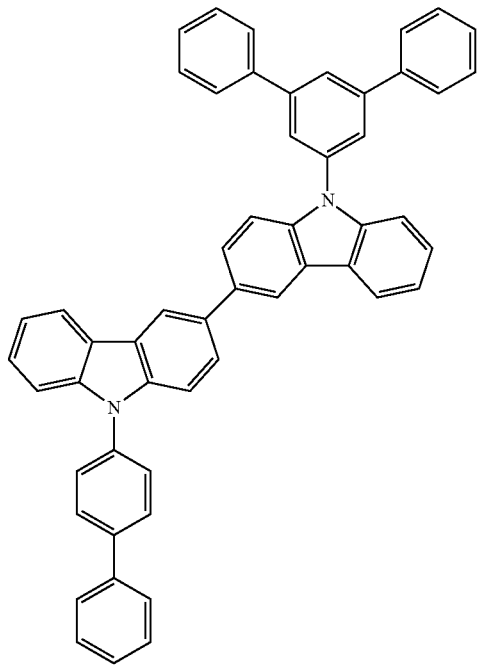
[B-32]
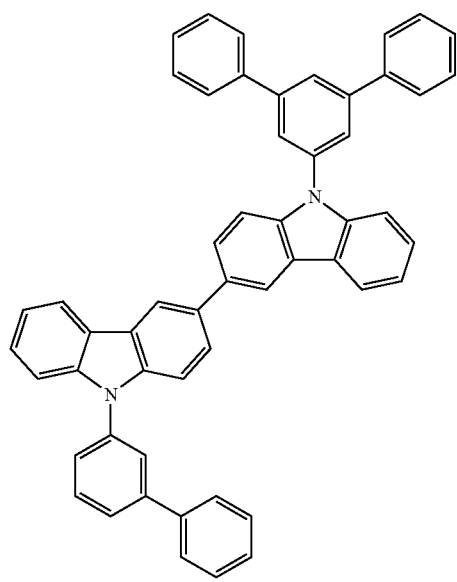
[B-33]
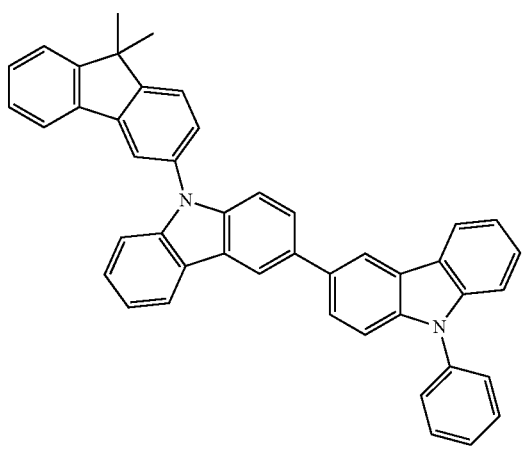

-continued
[B-34]
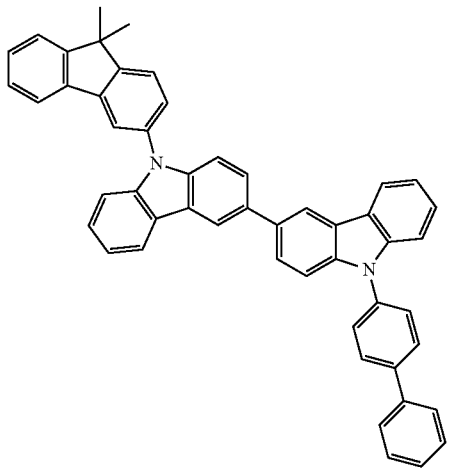
[B-35]
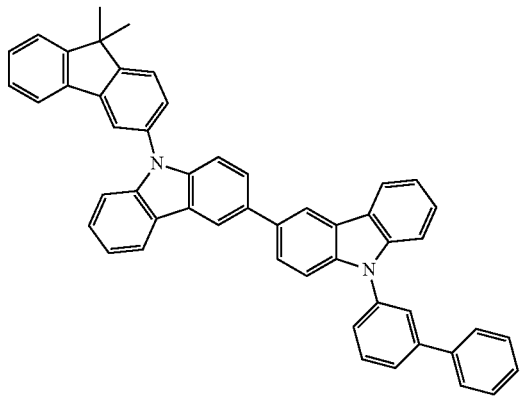
[B-36]
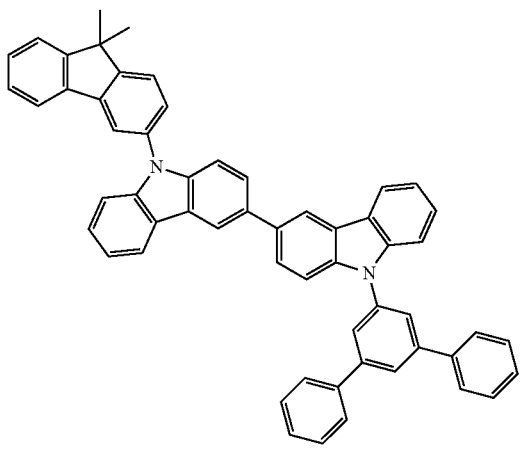
[B-37]
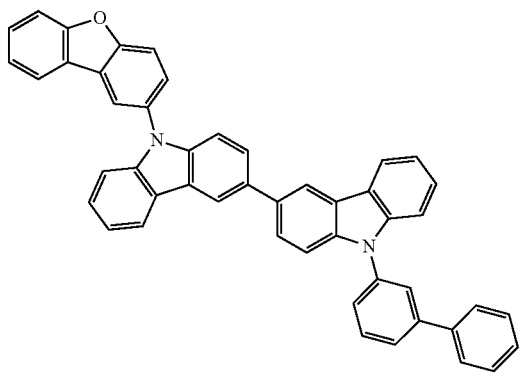
[B-38]
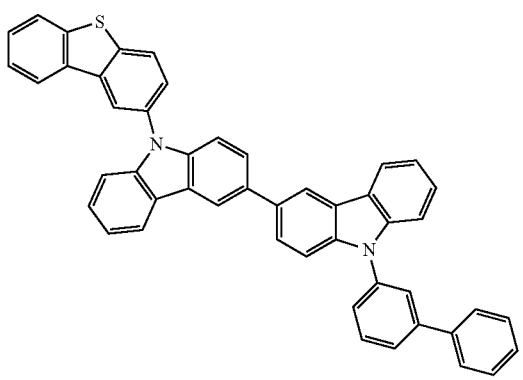
[B-39]
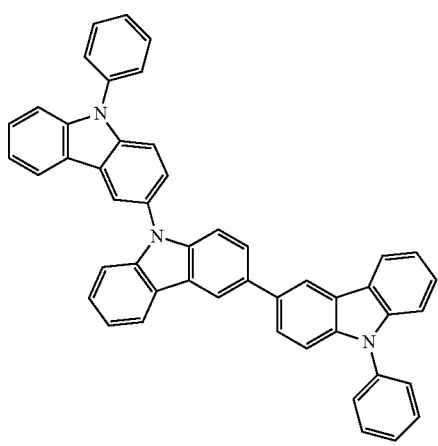

-continued
[B-40]
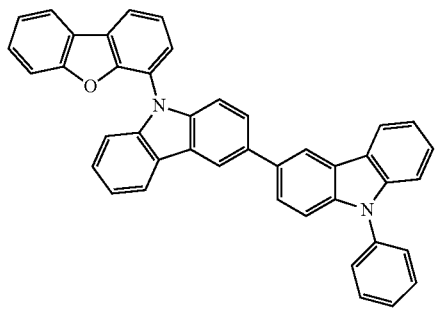
[B-41]
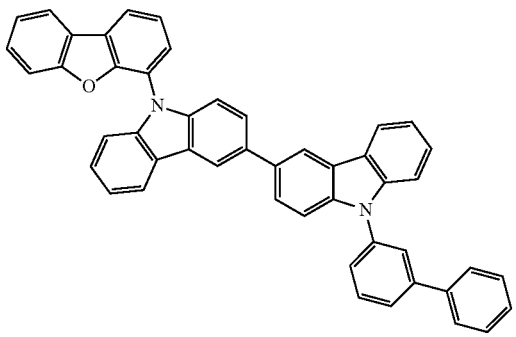
[B-42]
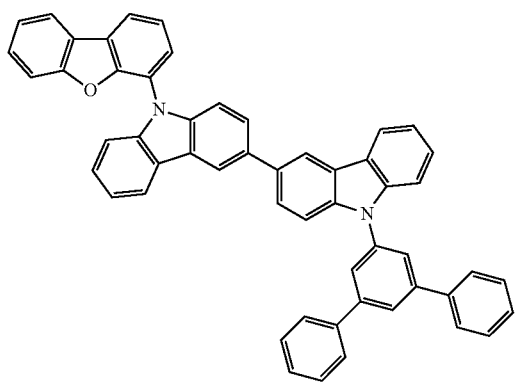
[B-43]
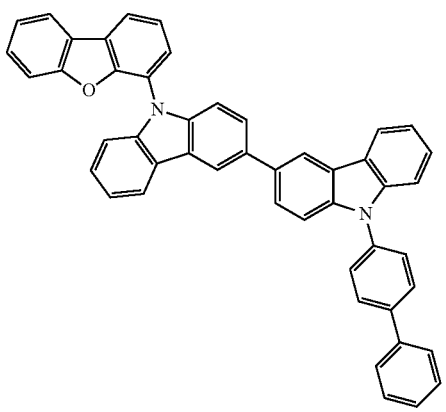
[B-44]
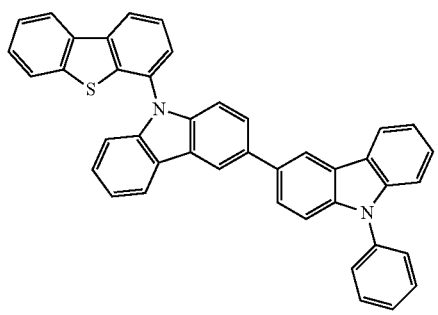
[B-45]
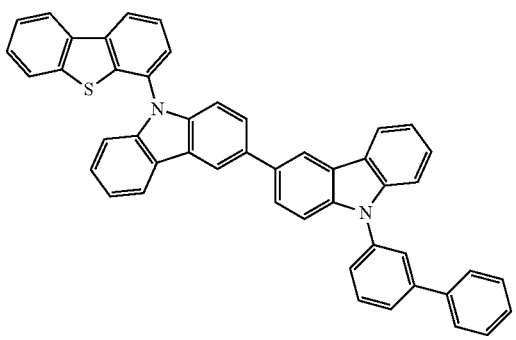
[B-46]
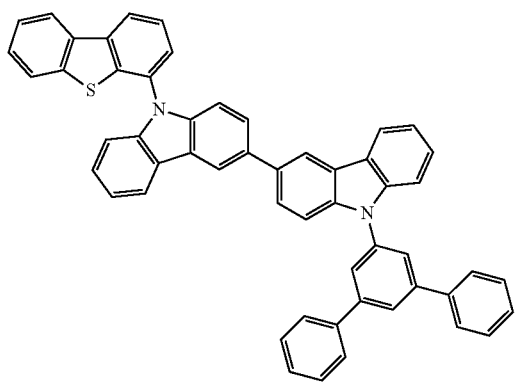
[B-47]
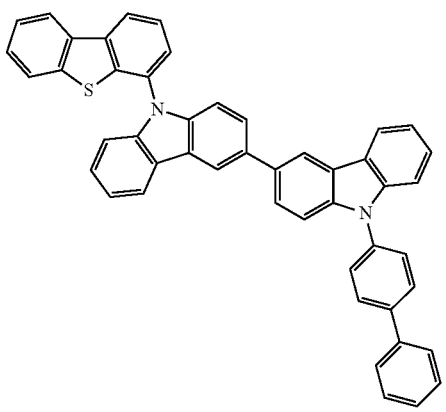

-continued
[B-48]
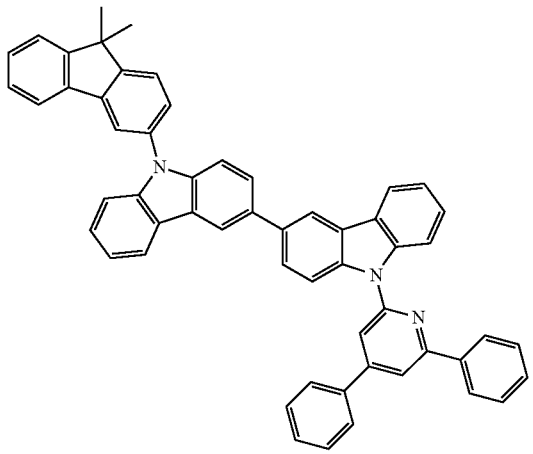
[B-49]
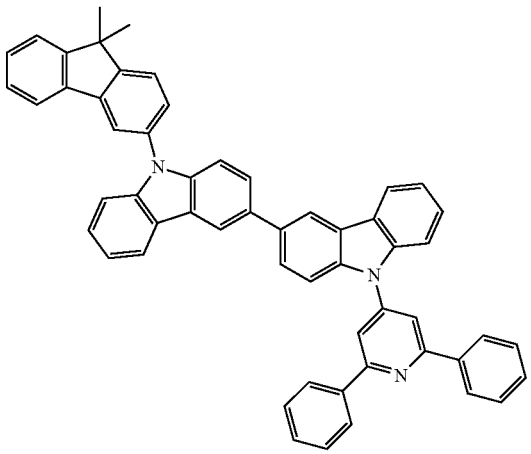
[B-50]
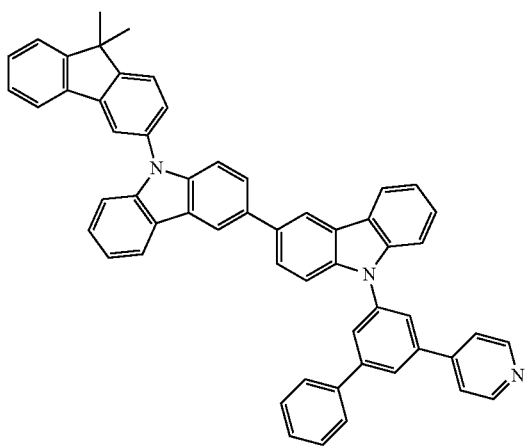
[B-51]
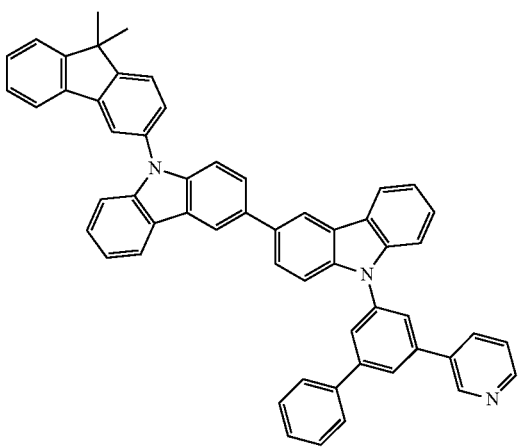
[B-52]
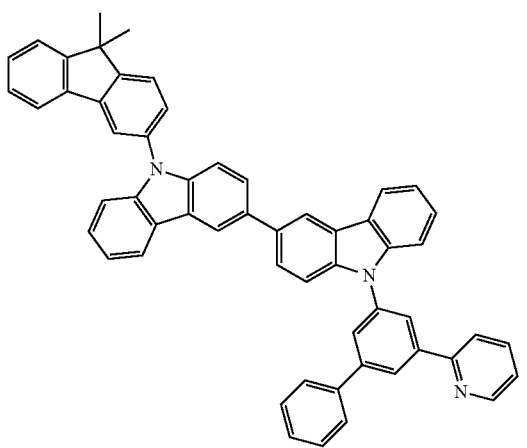
[B-53]
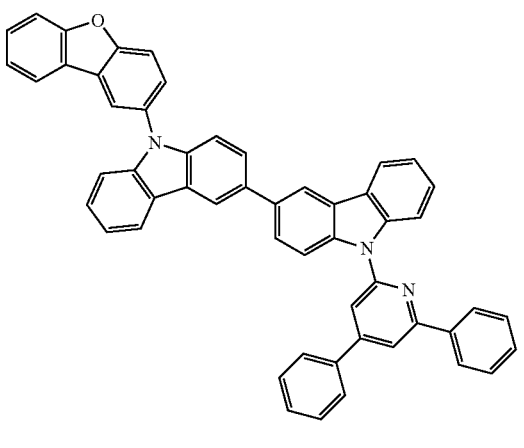

-continued
[B-54]
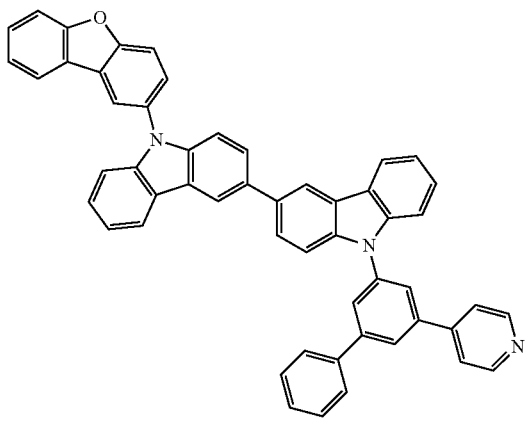
[B-55]
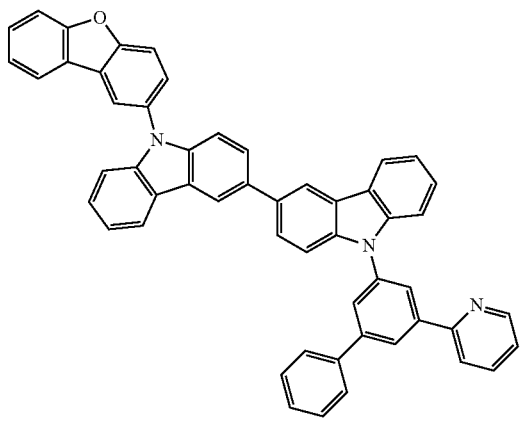
[B-56]
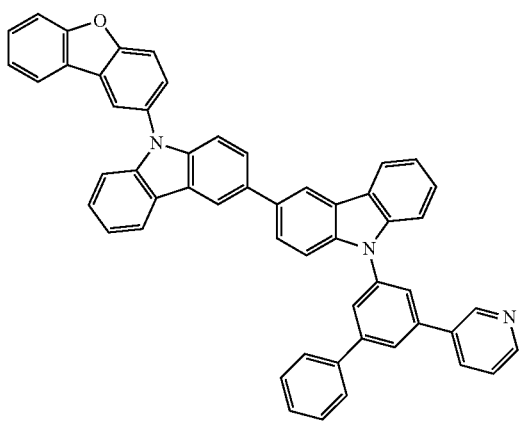
[B-57]
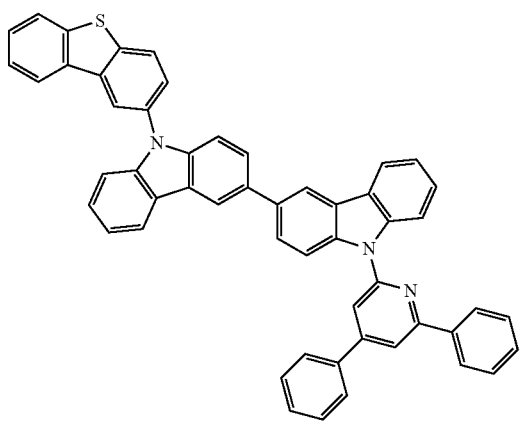
[B-58]
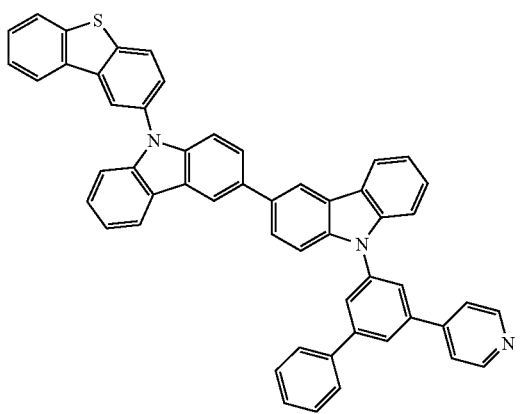
[B-59]
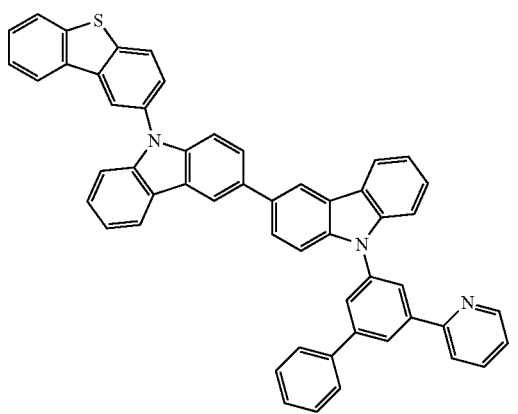

-continued
[B-60]
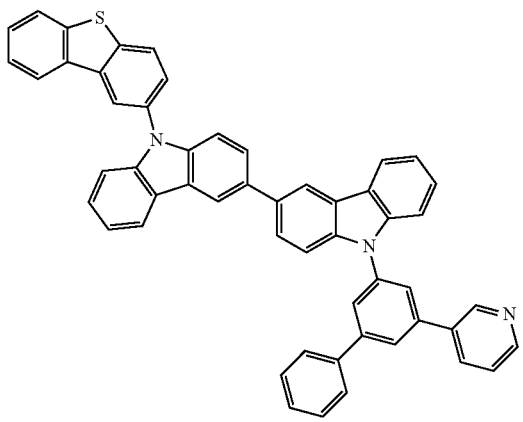
[B-61]
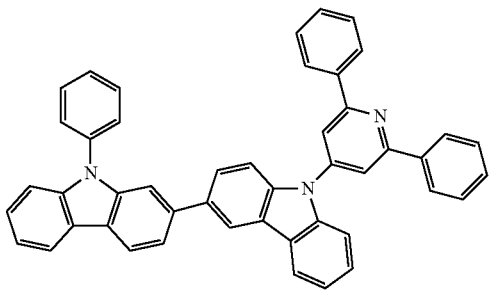
[B-62]
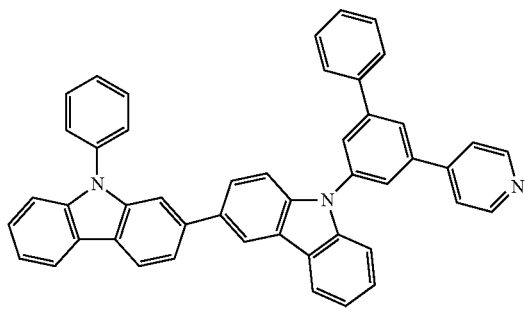
[B-63]
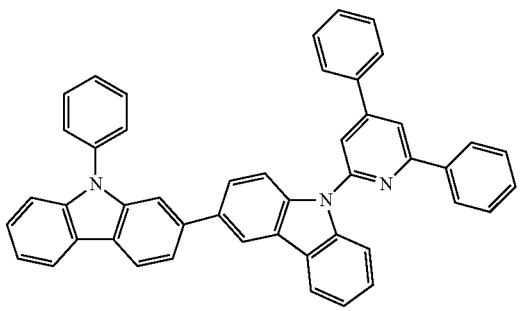
[B-64]
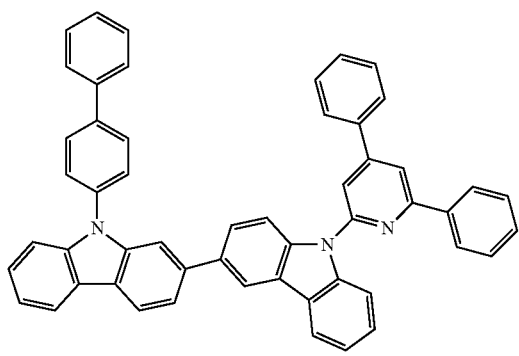
[B-65]
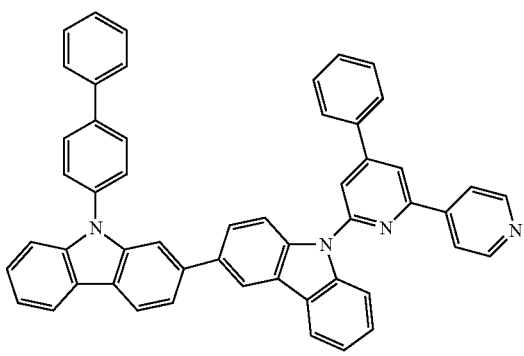
[B-66]
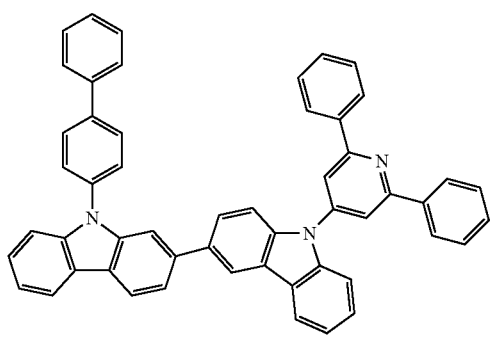
[B-67]
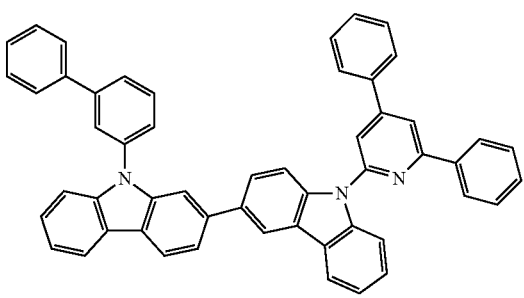

-continued
[B-68]
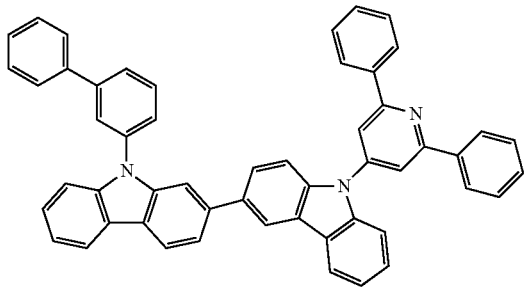
[B-69]
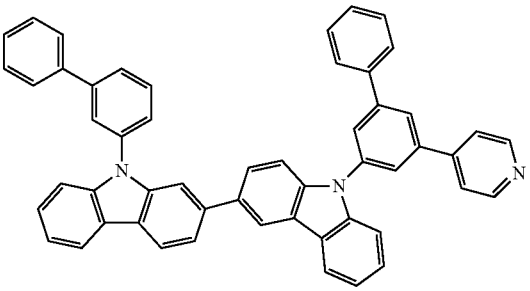
[B-70]
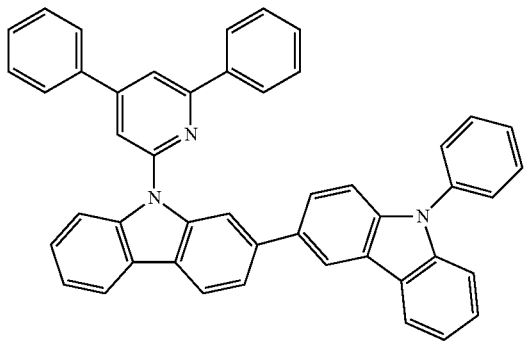
[B-71]
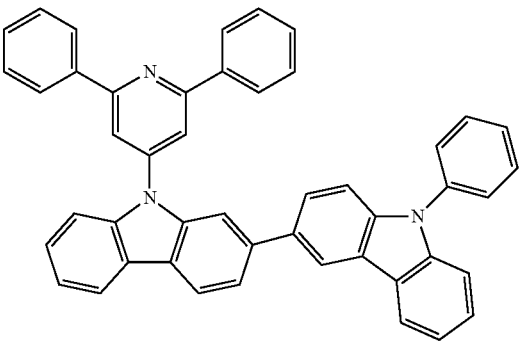
[B-72]
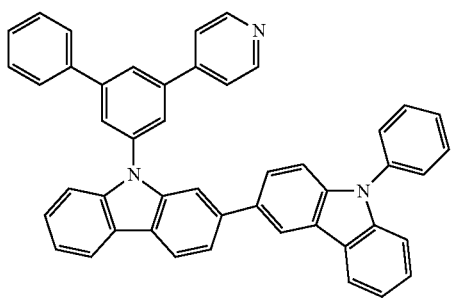
[B-73]
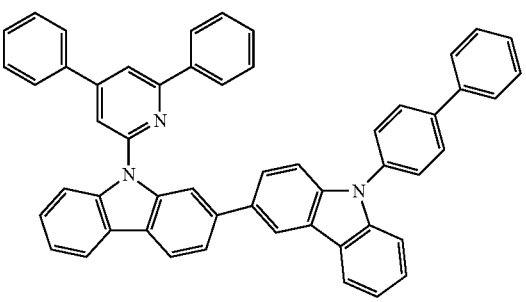
[B-74]
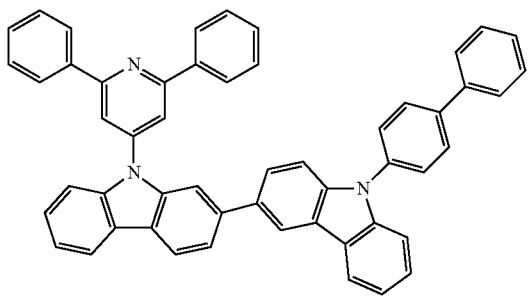
[B-75]
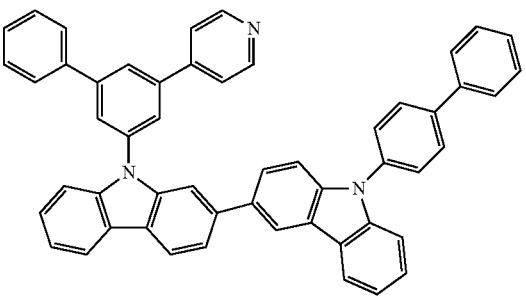
[B-76]
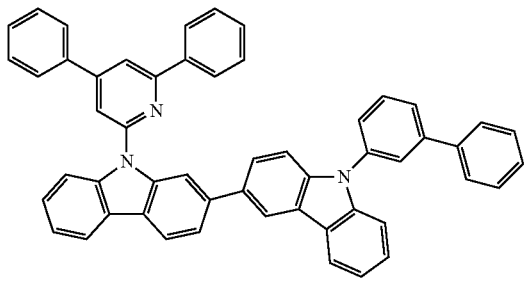
[B-77]
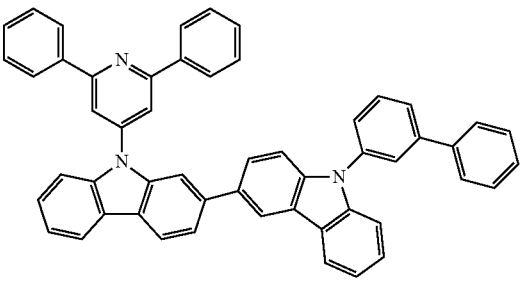

-continued
[B-78]
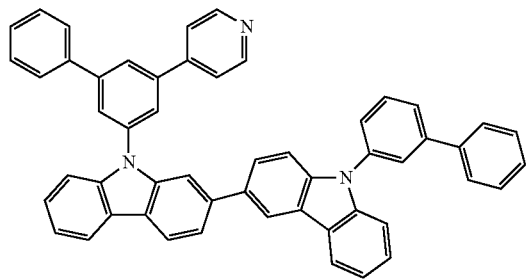
[B-79]
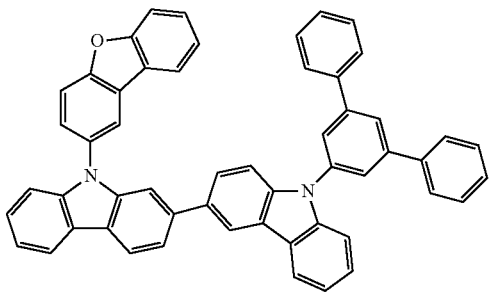
[B-80]
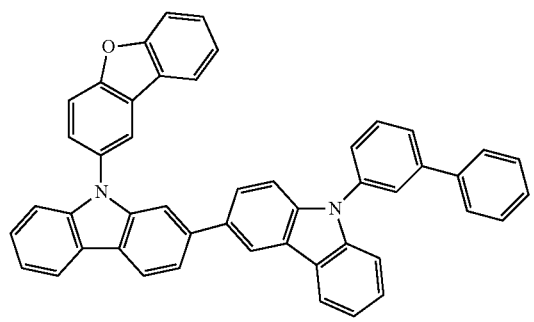
[B-81]
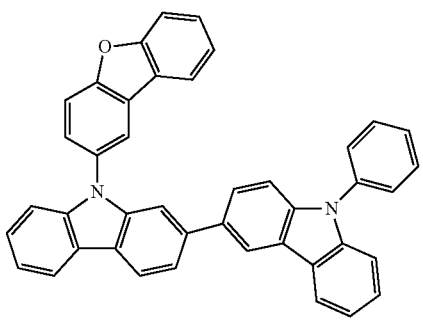
[B-82]
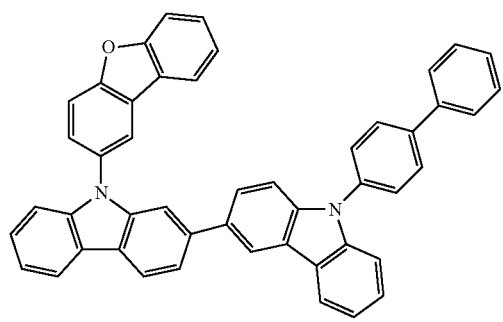
[B-83]
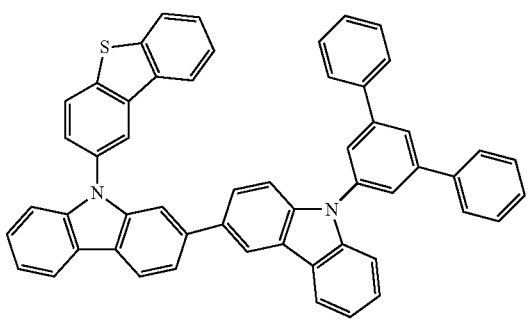
[B-84]
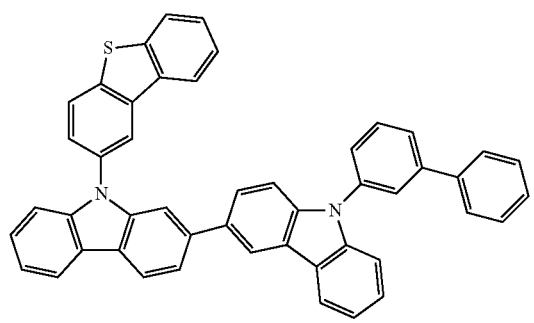
[B-85]
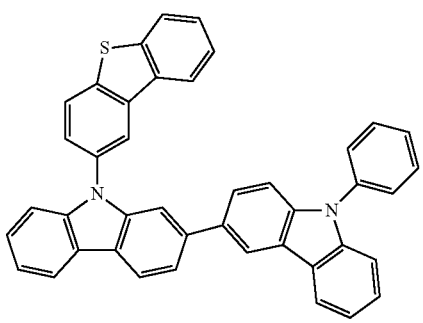

-continued
[B-86]
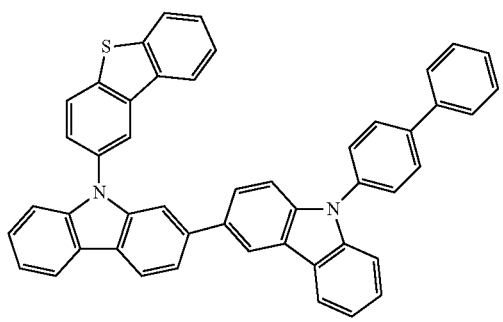
[B-87]
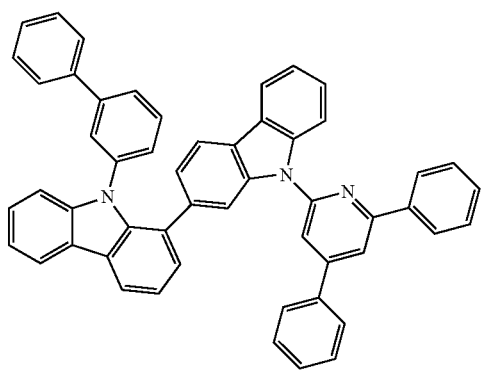
[B-88]
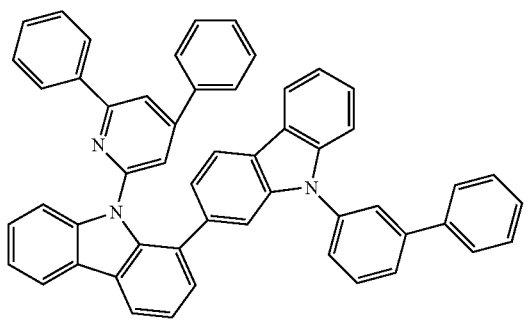
[B-89]
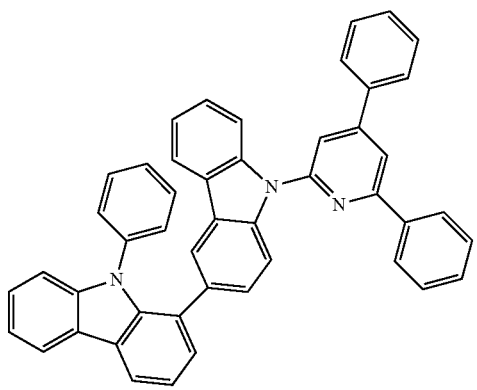
[B-90]
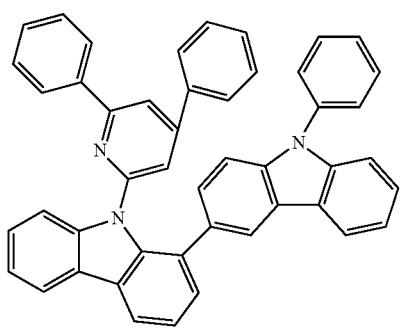
[B-91]
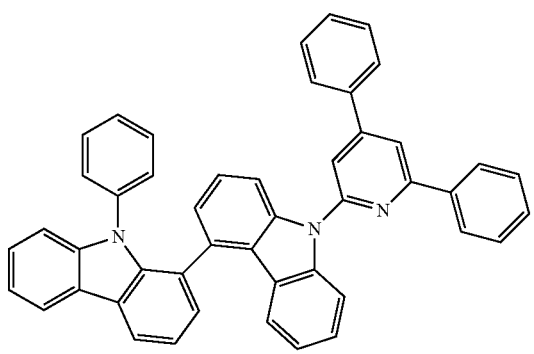
[B-92]
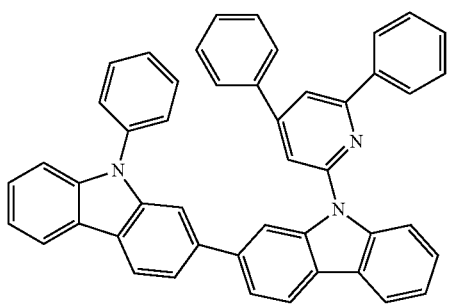
[B-93]
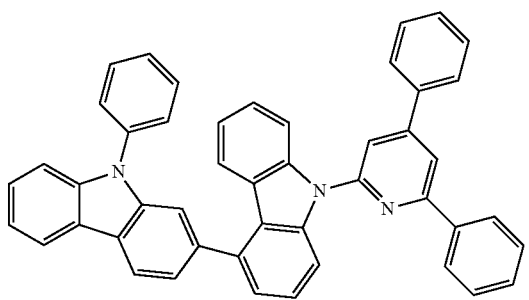

-continued
[B-94]
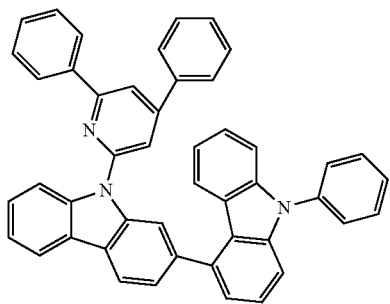
[B-95]
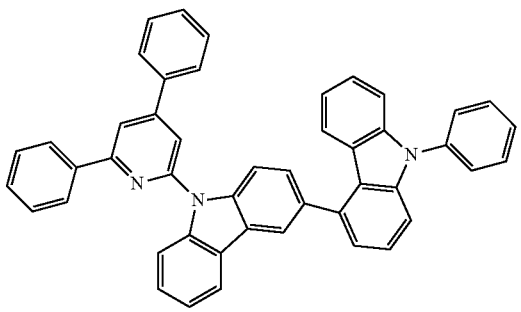
[B-96]
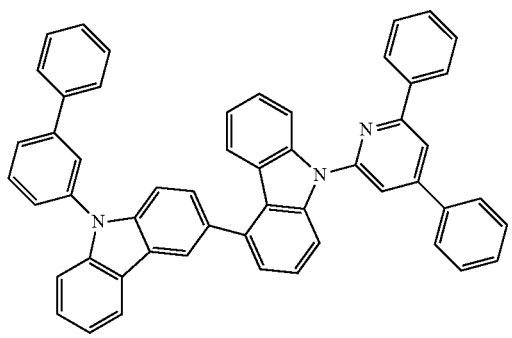
[B-97]
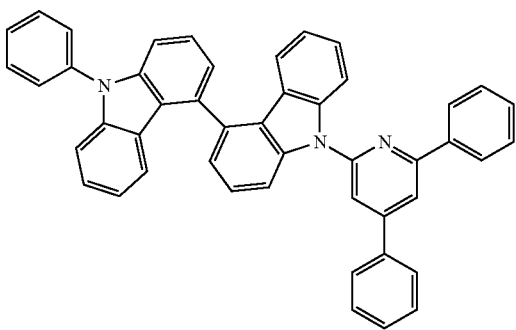
[B-98]
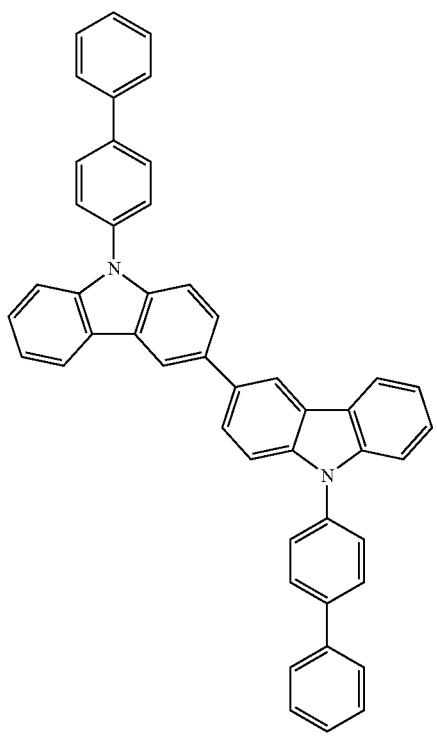
[B-99]
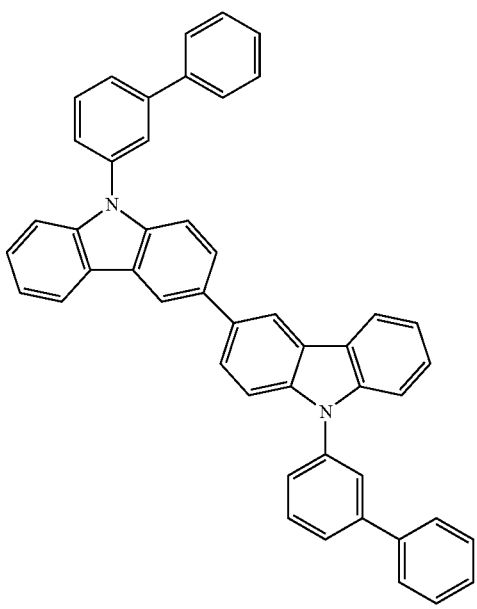

-continued
[B-100]
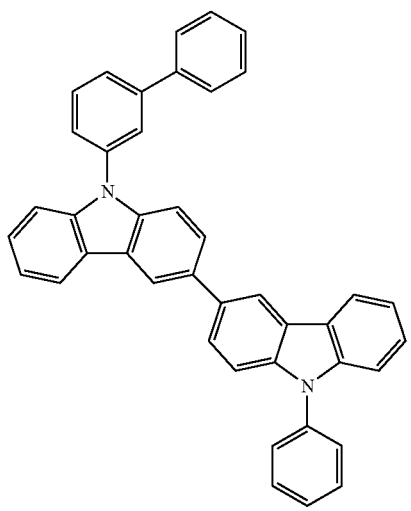
[B-101]
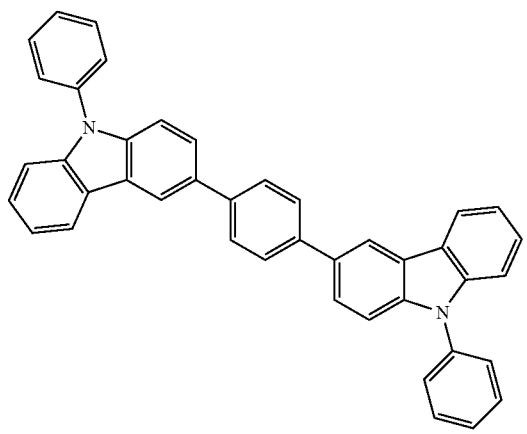
[B-102]
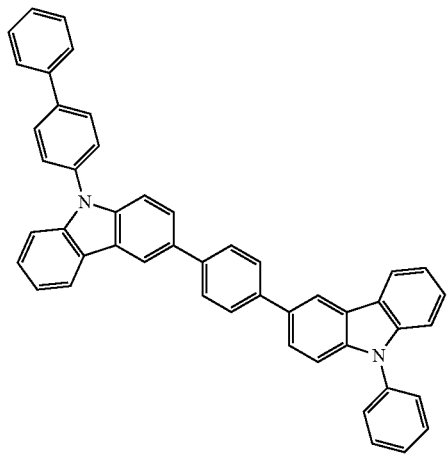
[B-103]
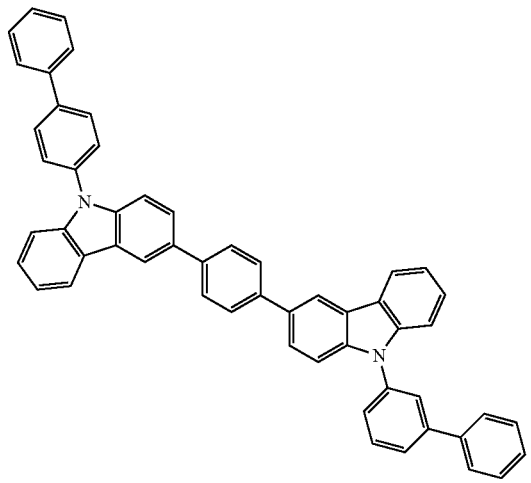
[B-104]
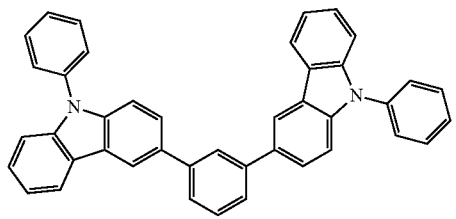
[B-105]
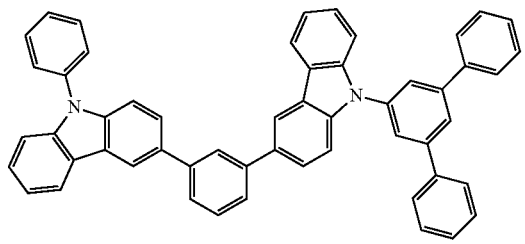

[B-106]
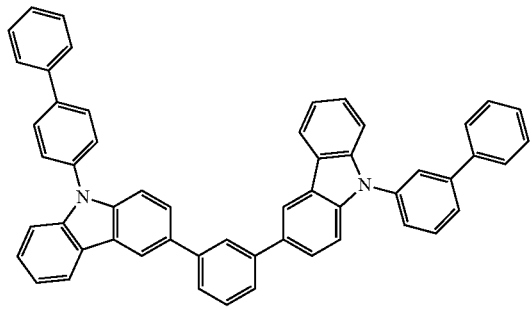
[B-107]
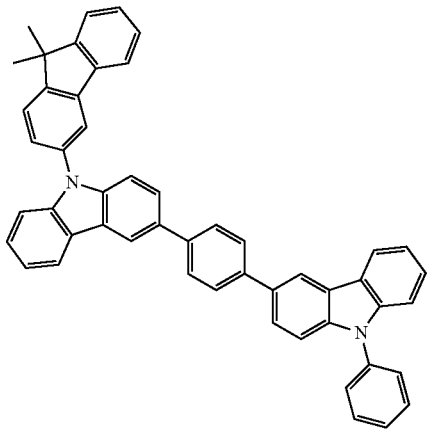
[B-108]
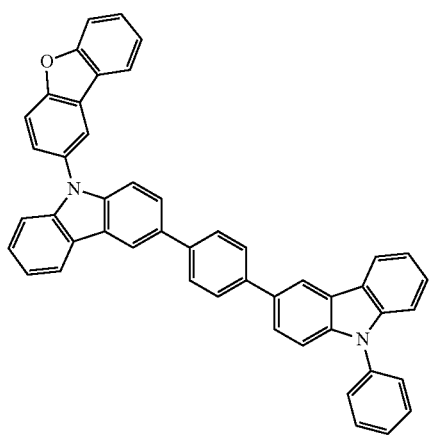
[B-109]
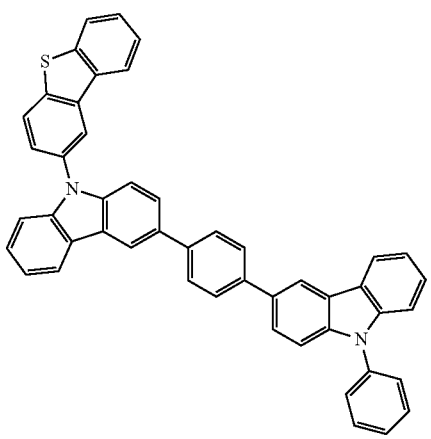
[B-110]
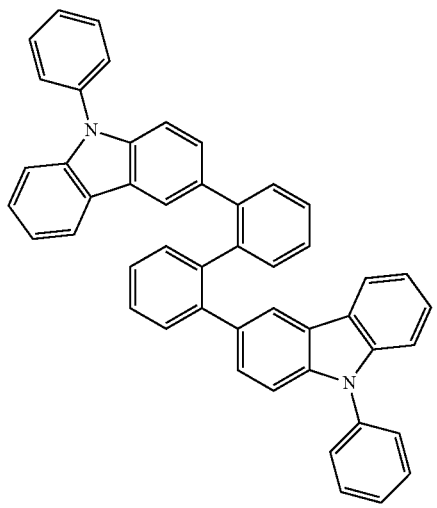
[B-111]
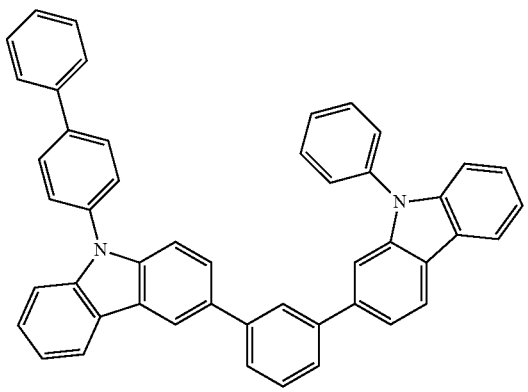

-continued
[B-112] 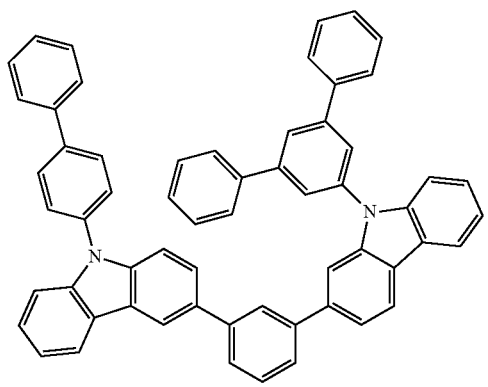
[B-113] 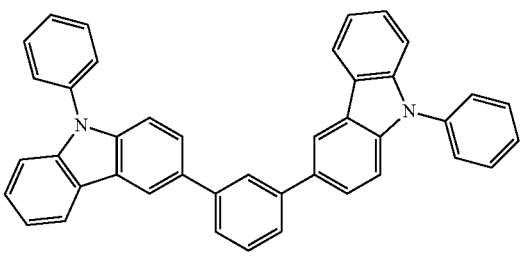
[B-114] 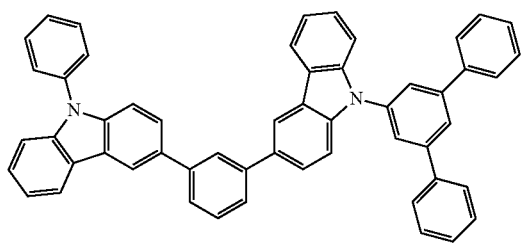
[B-115] 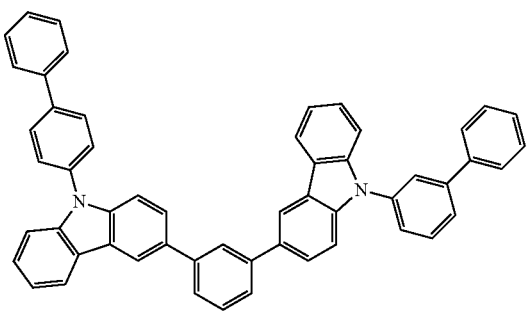
[B-116] 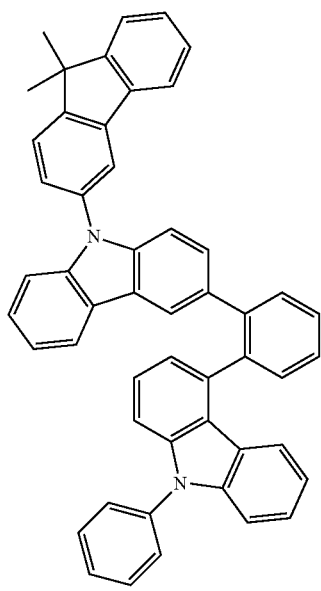
[B-117] 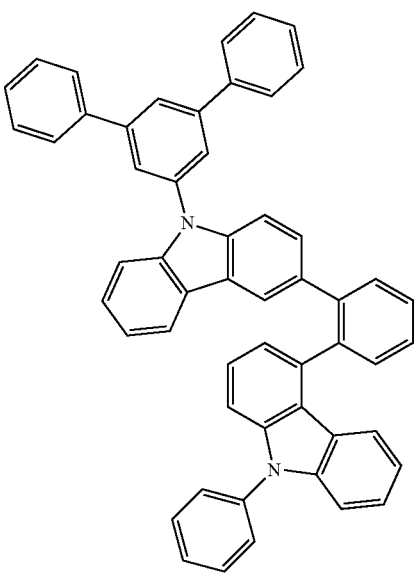

[B-118]
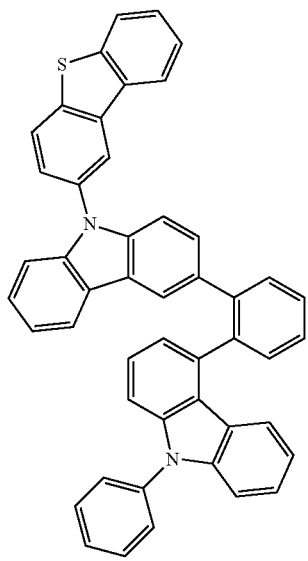
[B-119]
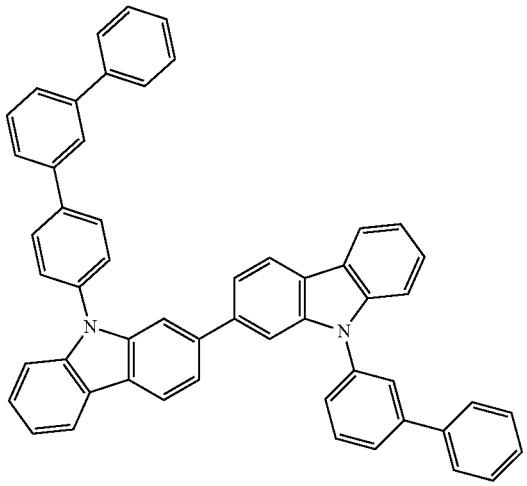
[B-120]
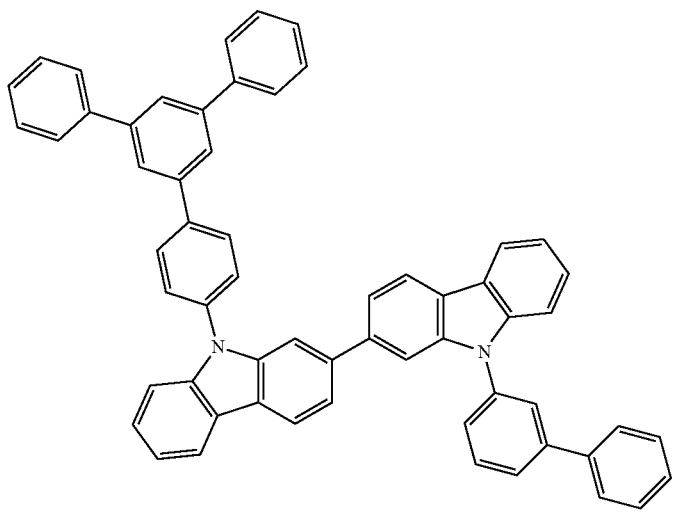
[B-121]
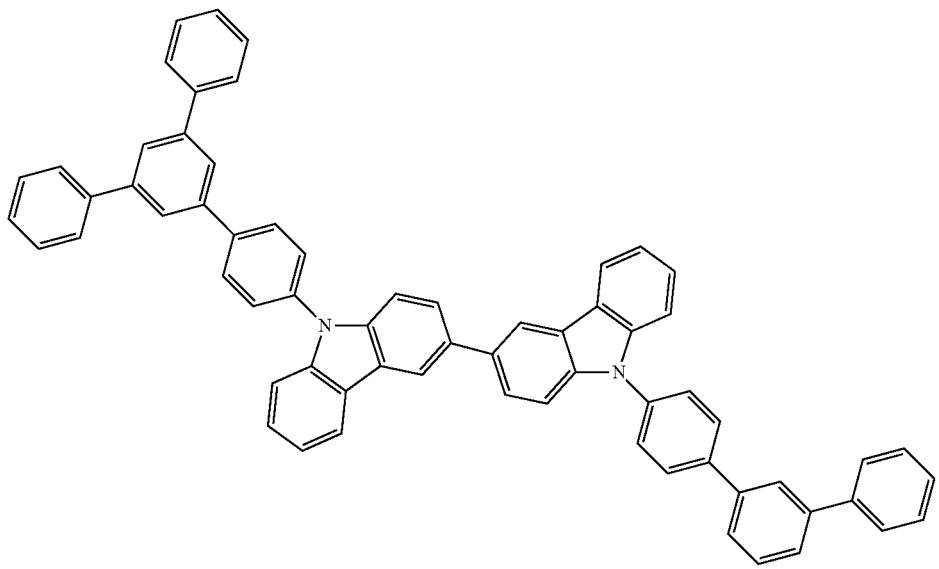

-continued
[B-122]
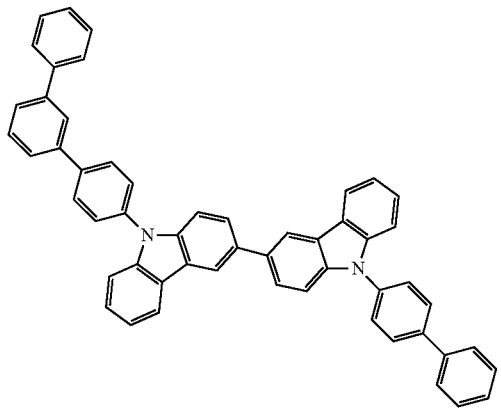
[B-123]
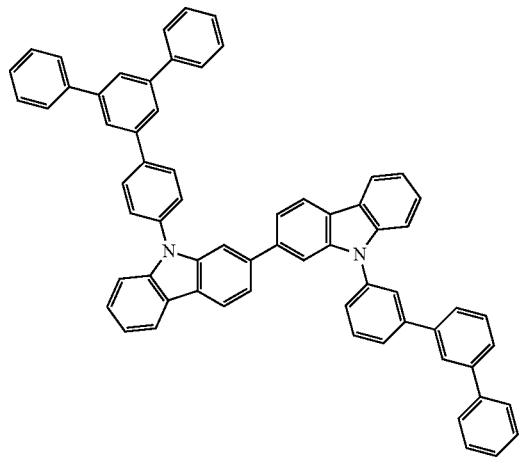
[B-124]
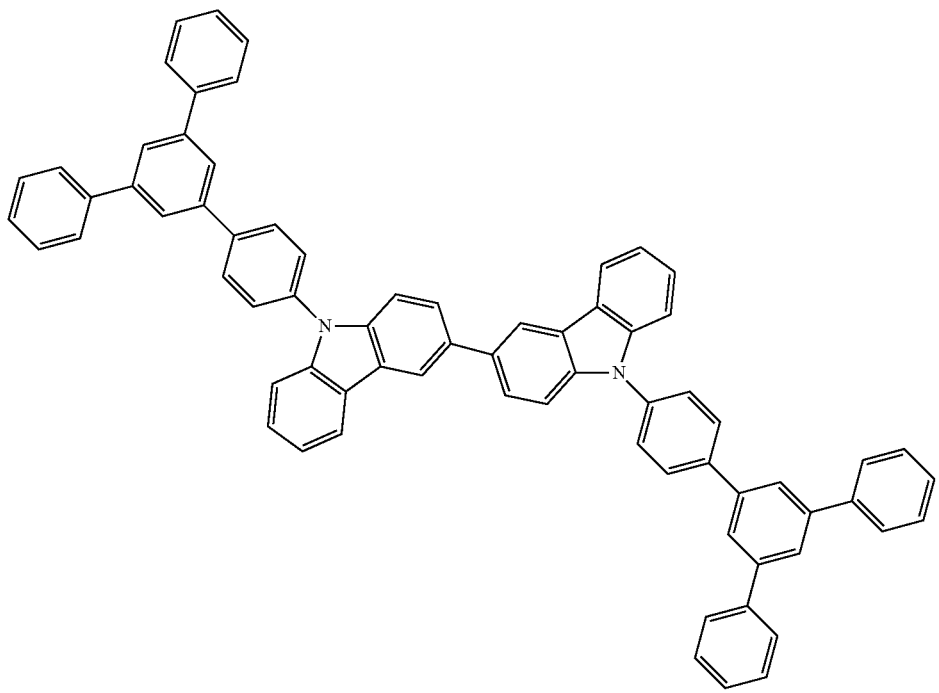

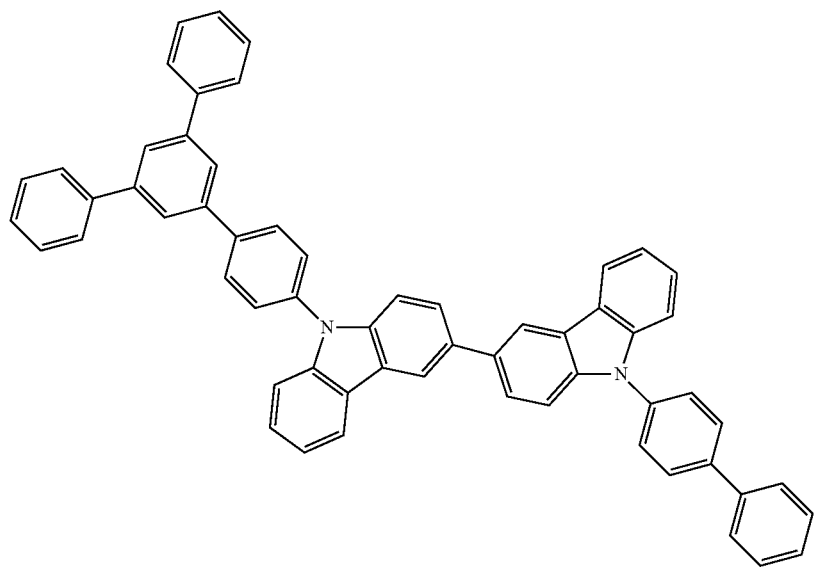
[B-125]
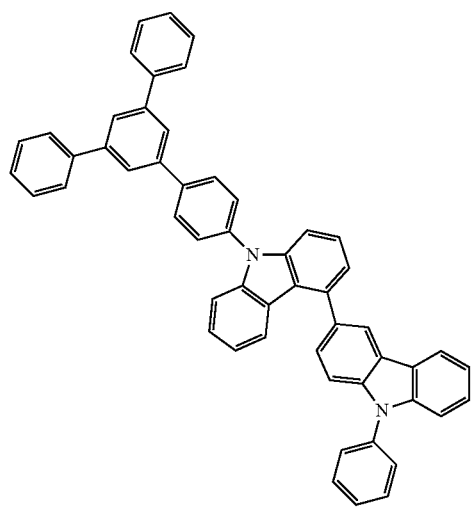
[B-126]
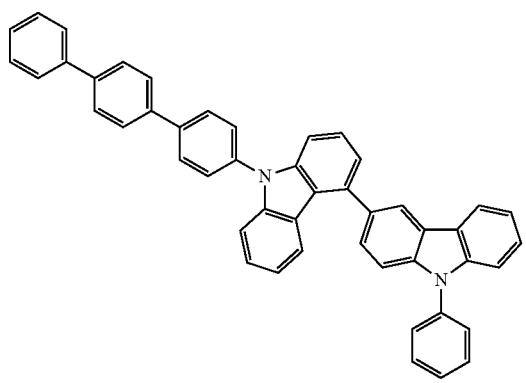
[B-127]

-continued
[B-128]
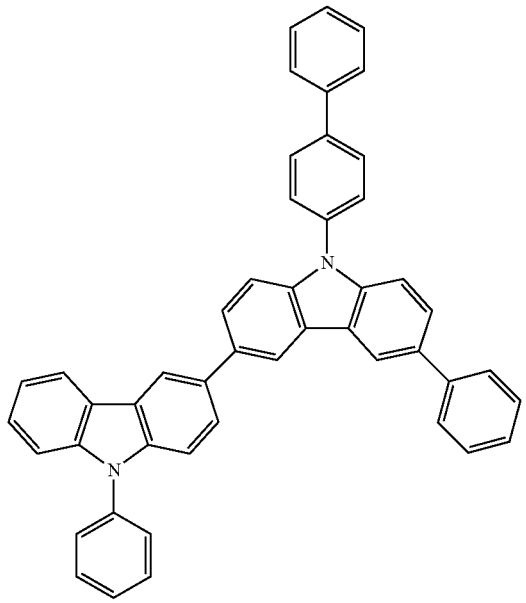
[B-129]
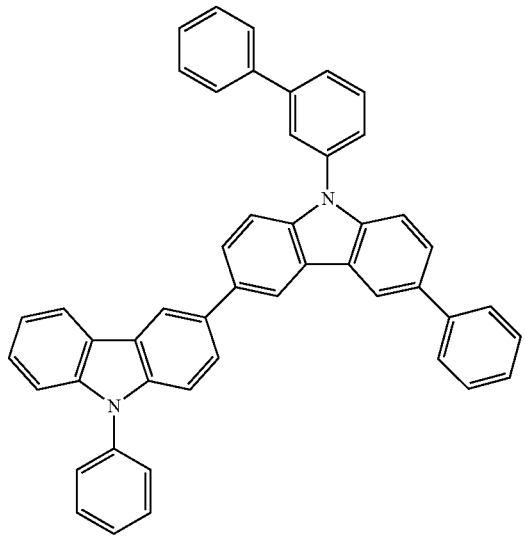
[B-130]
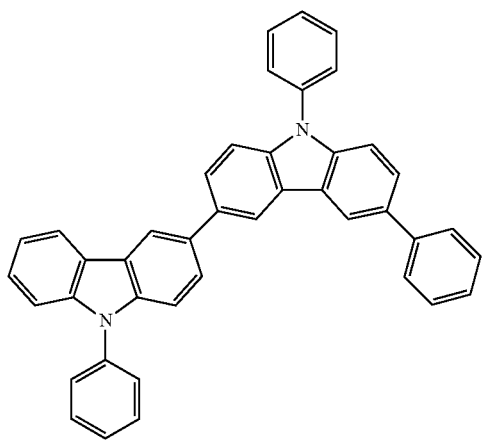
[B-131]
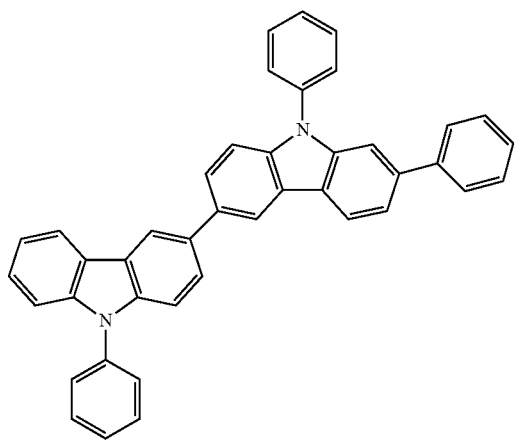
[B-132]
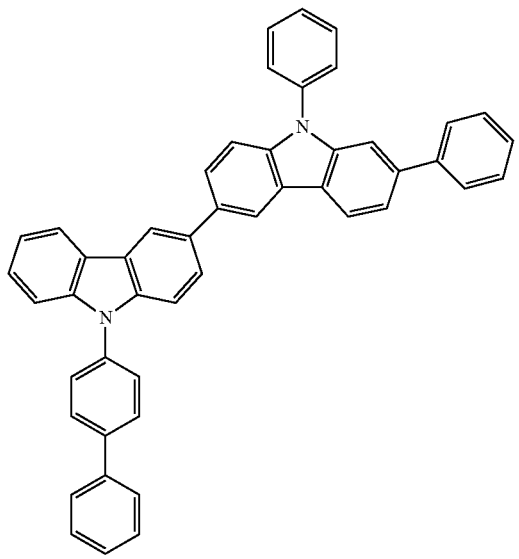
[B-133]
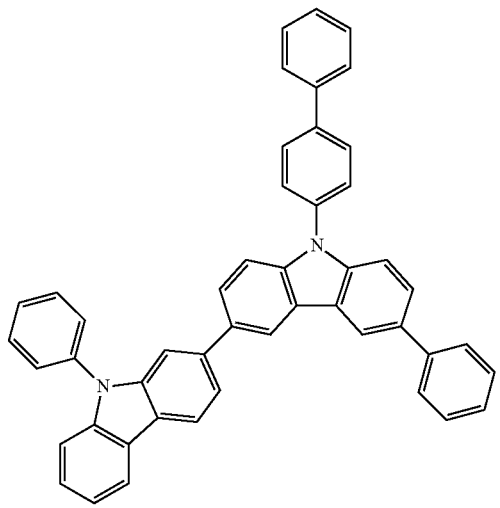

-continued
[B-134]
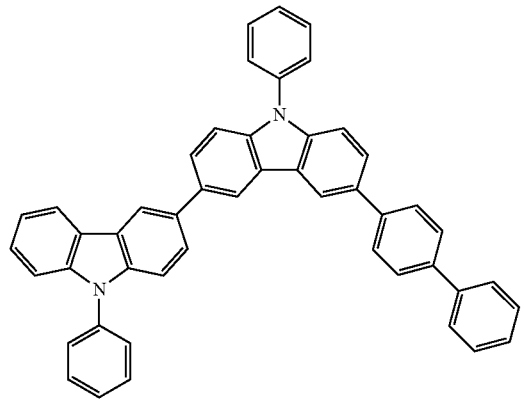
[B-135]
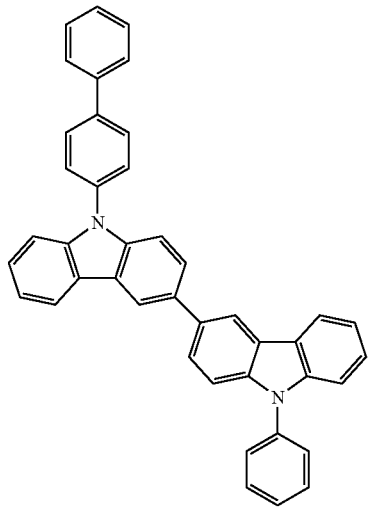
[B-136]
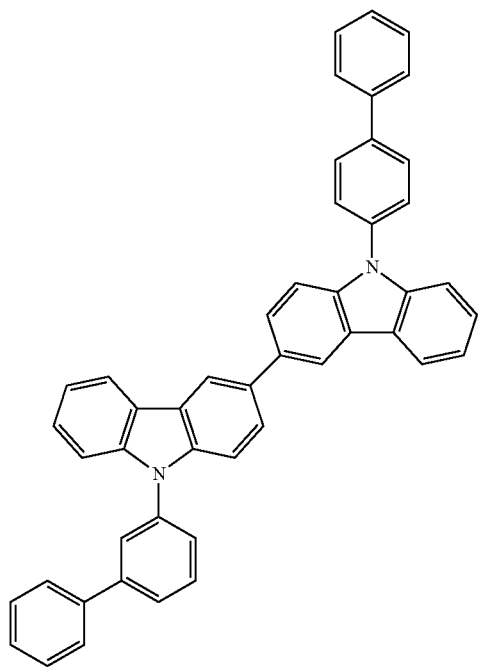
[B-137]
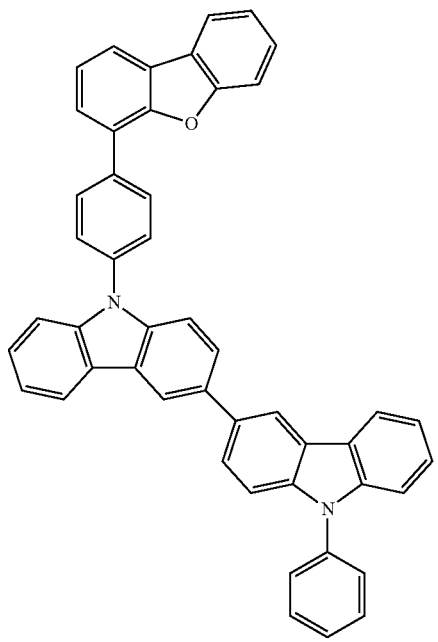

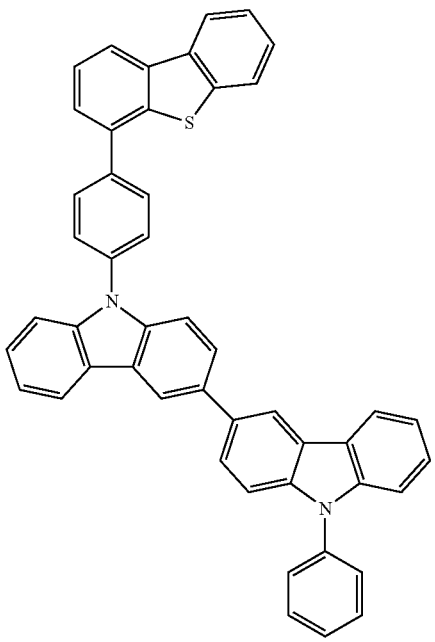

[B-138]

The second compound for an organic optoelectric device is a compound having relatively strong hole characteristics and is used with the first compound for an organic optoelectric device in a light-emitting layer and thus charge mobility and stability are increased and thus luminous efficiency and life-span characteristics are improved. Charge mobility may be controlled by adjusting a ratio of the second compound for an organic optoelectric device having hole characteristics and the first compound for an organic optoelectric device.

In addition, the first compound for an organic optoelectric device and the second compound for an organic optoelectric device may be, for example included in a weight ratio of about 1:9 to 9:1, and specifically about 2:8 to 8:2, about 3:7 to 7:3, about 4:6 to 6:4, and about 5:5. Within the ranges, bipolar characteristics are realized and efficiency and life-span may be improved simultaneously.

As an example of the composition for an organic optoelectric device, the first compound for an organic optoelectric device may be represented by Chemical Formula 1-A and the second compound for an organic optoelectric device may be represented by Chemical Formula 2.

The composition may further include at least one organic compound in addition to the first compound for an organic optoelectric device and the second compound for an organic optoelectric device.

The compound for an organic optoelectric device may further include a dopant. The dopant may be a red, green, or blue dopant.

The dopant is a material in small amount to cause light emission and may be generally a material such as a metal complex that emits light by multiple excitation into a triplet or more. The dopant may be, for example an inorganic, organic, or organic/inorganic compound, and one or more kinds thereof may be used.

One example of the dopant may be a phosphorescent dopant, examples of the phosphorescent dopant may be an organometal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

L$_2$MX            [Chemical Formula Z]

In Chemical Formula Z, M is a metal, and L and X are the same or different, and are a ligand to form a complex compound with M.

The M may be, for example, Ir, Pt, Os, Ti, Zr, Hf, Eu, Tb, Tm, Fe, Co, Ni, Ru, Rh, Pd, or a combination thereof and L and X may be, for example a bidendate ligand.

Hereinafter, an organic optoelectric device including the compound for an organic optoelectric device or the composition for an organic optoelectric device is described.

An organic optoelectric device according to another embodiment includes an anode and a cathode facing each other and at least one organic layer disposed between the anode and the cathode, wherein the organic layer includes the compound for an organic optoelectric device, or the composition for an organic optoelectric device.

For example, the organic layer may include a light-emitting layer and the light-emitting layer may include the compound for an organic optoelectric device or the composition for an organic optoelectric device.

Specifically, the compound for an organic optoelectric device, or the composition for an organic optoelectric device may be included as a host of the light-emitting layer.

Specifically, the compound for an organic optoelectric device or the composition for an organic optoelectric device may be used in an electron transport auxiliary layer of the organic layer.

For another example, the organic layer may include at least one auxiliary layer selected from a hole injection layer, a hole transport layer, an electron blocking layer, an electron transport layer, an electron injection layer, and a hole blocking layer, and the compound for an organic optoelectric device may be included in the auxiliary layer.

For another example, the electron transport layer may further include an electron transport auxiliary layer that is adjacent to the light-emitting layer and the compound for an organic optoelectric device may be included in the electron transport auxiliary layer.

The compound for an organic optoelectric device may be included in the organic layer using a dry film formation method such as chemical vapor deposition (CVD) or a solution process.

The organic optoelectric device may have a low driving voltage, a high efficiency, high luminance, and long life-span due to the organic layer including the compound for an organic optoelectric device represented by Chemical Formula 1.

FIGS. 1 to 4 show schematic cross-sections of the organic light emitting diodes 100, 200, 300, and 400 according to embodiments. Hereinafter, referring to FIG. 1, a structure and a manufacturing method of an organic light emitting diode according to one embodiment are as follows.

The organic light emitting diode 100 has a structure where a cathode 110, an organic layer 105, and an anode 120 are sequentially stacked.

A substrate may be further disposed under the cathode 110 or on the anode 120. The substrate may be a substrate that used in a general organic light emitting diode and may be a glass substrate or a transparent plastic substrate with strong mechanical strength, thermal stability, transparency, surface smoothness, ease of handling, and water resistance.

The anode 120 may be formed by depositing or sputtering an anode material on a substrate. The anode material may be selected from materials having a high work function that makes hole injection easy. The anode 120 may be a reflective electrode, a transflective electrode, or a transmissive electrode. The anode material may use indium tin oxide (ITO), indium zinc oxide (IZO), tin oxide ($SnO_2$), zinc oxide (ZnO), and the like. Or, it may be a metal such as magnesium (Mg), aluminum (Al), aluminum-lithium (Al—Li), calcium (Ca), magnesium-indium (Mg—In), or magnesium-silver (Mg—Ag).

The anode 120 may have a monolayer or a multi-layer structure of two or more layers.

An organic layer 105 is disposed on the anode 120.

The organic layer 105 may include a hole transport region; a light-emitting layer; and an electron transport region. For example, referring to FIG. 2, an organic light emitting diode according to an embodiment of the present invention is described.

The organic layer 105 further includes a hole auxiliary layer 140 between the anode 120 and the light-emitting layer 130.

Referring to FIG. 3, the hole transport region may include at least two layered hole auxiliary layer, and in this case, a hole auxiliary layer contacting the light-emitting layer is defined as a hole transport auxiliary layer 33 and a hole auxiliary layer contacting an anode is defined as a hole transport layer 31.

The hole transport region may include at least one of a hole injection layer, a hole transport layer, an electron blocking layer, and a buffer layer.

The hole transport region may include only hole injection layer or only hole transport layer. Or, the hole transport region may have a structure where a hole injection layer 37/hole transport layer 31 or hole injection layer 37/hole transport layer 31/electron blocking layer is sequentially stacked from the anode 120.

For example, the hole injection layer 37 and the electron injection layer 36 are additionally included and as shown in FIG. 4, anode 120/hole injection layer 37/hole transport layer 31/hole transport auxiliary layer 33/light-emitting layer 130/electron transport auxiliary layer 35/electron transport layer 34/electron injection layer 36/cathode 110 are sequentially stacked.

The hole injection layer 37 may improve interface properties between ITO as an anode and an organic material used for the hole transport layer 31, and is applied on a non-planarized ITO and thus planarizes the surface of the ITO. For example, the hole injection layer 37 may include a material having a median value, particularly desirable conductivity between a work function of ITO and HOMO of the hole transport layer 31, in order to adjust a difference a work function of ITO as an anode and HOMO of the hole transport layer 31. In connection with the present invention, the hole injection layer 37 may include N4,N4'-diphenyl-N4,N4'-bis (9-phenyl-9H-carbazol-3-yl)biphenyl-4,4'-diamine), but is not limited thereto. In addition, the hole injection layer 37 may further include a conventional material, for example, copper phthlalocyanine (CuPc), aromatic amines such as N,N'-dinaphthyl-N,N'-phenyl-(1,1'-biphenyl)-4,4'-diamine (NPD), 4,4',4"-tris[methylphenyl(phenyl)amino] triphenyl amine (m-MTDATA), 4,4',4"-tris[1-naphthyl(phenyl) amino] triphenyl amine (1-TNATA), 4,4',4"-tris[2-naphthyl (phenyl)amino]triphenyl amine (2-TNATA), 1,3,5-tris[N-(4-diphenylaminophenyl)phenylamino] benzene (p-DPA-TDAB), and the like, compounds such as 4,4'-bis[N-[4-{N, N-bis(3-methylphenyl)amino}phenyl]-N-phenylamino] biphenyl (DNTPD), hexaazatriphenylene-hexacarbonitirile (HAT-CN), and the like, a polythiophene derivative such as poly(3,4-ethylenedioxythiophene)-poly(styrnesulfonate) (PEDOT) as a conductive polymer. The hole injection layer 37 may be, for example coated on ITO as an anode in a thickness of about 10 to 300 Å.

When the hole transport region includes a hole injection layer 37, the hole injection layer may be formed on the anode 120 by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-8}$ torr to about $10^{-3}$ torr, and a deposition rate of about 0.01 to about 100 Å/sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

Conditions for forming the hole transport layer and the electron blocking layer may be defined based on the above-described formation conditions for the hole injection layer.

Å thickness of the hole transport region may be from about 100 Å to about 10000 Å, for example, about 100 Å to about 1000 Å. When the hole transport region includes the hole injection layer and the hole transport layer, a thickness of the hole injection layer may be from about 100 Å to about 10,000 Å, for example about 100 Å to about 1000 Å and a thickness of the hole transport layer may be from about 50 Å to about 2,000 Å, for example about 100 Å to about 1500 Å. When the thicknesses of the hole transport region, the HIL, and the HTL are within these ranges, satisfactory hole transport characteristics may be obtained without a substantial increase in a driving voltage.

The hole transport region may further include a charge-generating material to improve conductivity, in addition to the materials as described above. The charge-generating material may be homogeneously or non-homogeneously dispersed in the hole transport region.

The charge-generating material may be, for example, a p-dopant. The p-dopant may be one of a quinine derivative, a metal oxide, and a cyano group-containing compound, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound HT-D1 below.

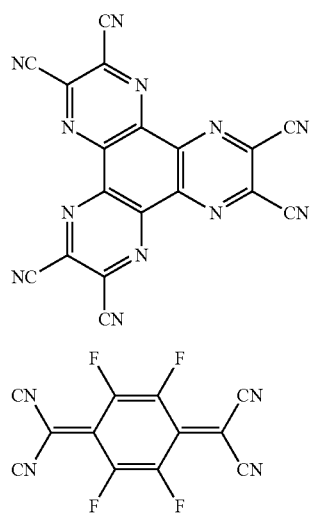

<Compound HT-D1>

<F4-TCNQ>

The hole transport region may further include a buffer layer.

The buffer layer may compensate for an optical resonance distance of light according to a wavelength of the light emitted from the light-emitting layer, and thus may increase efficiency.

The light-emitting layer (EML) may be formed on the hole transport region by using vacuum deposition, spin coating, casting, LB method, or the like. When the light-emitting layer is formed using vacuum deposition or spin coating, the conditions for deposition and coating may be similar to those for the formation of the hole injection layer, though the conditions for the deposition and coating may vary depending on the material that is used to form the light-emitting layer.

The light-emitting layer may include a host and a dopant.

A thickness of the light-emitting layer may be about 100 Å to about 1000 Å, for example about 200 Å to about 600 Å. When the thickness of the light-emitting layer is within these ranges, the light-emitting layer may have improved emission characteristics without a substantial increase in a driving voltage.

Next, an electron transport region is disposed on the light-emitting layer upper.

The electron transport region may include at least one of a hole blocking layer, an electron transport layer, and an electron injection layer.

For example, the electron transport region may have a structure of a hole blocking layer/electron transport layer/electron injection layer or electron transport layer/electron injection layer, but is not limited thereto. For example, an organic light emitting diode according to an embodiment of the present invention includes at least two electron transport layers in the electron transport region, and in this case, an electron transport layer contacting the light-emitting layer is defined as an electron transport auxiliary layer 35.

The electron transport layer may have a monolayer or multi-layer structure including two or more different materials.

The electron transport region may include the compound represented by Chemical Formula 1 for an organic optoelectric device. For example, the electron transport region may include an electron transport layer, and the electron transport layer may include the compound for an organic optoelectric device represented by Chemical Formula 1. More specifically, the electron transport auxiliary layer may include the compound represented by Chemical Formula 1 for an organic optoelectric device.

The formation conditions of the hole blocking layer, electron transport layer, and electron injection layer of the electron transport region refers to the formation condition of the hole injection layer.

When the electron transport region includes the hole blocking layer, the hole blocking layer may include at least one of BCP, Bphen, and BAlq, but is not limited thereto.

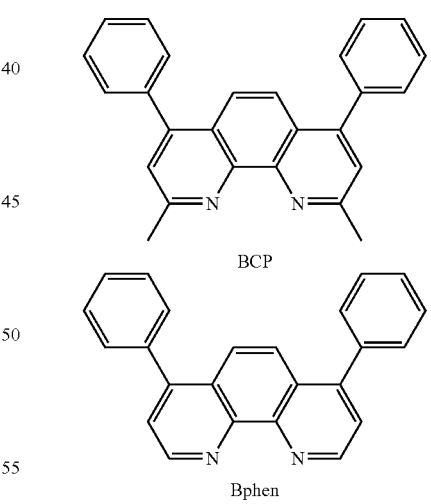

BCP

Bphen

A thickness of the hole blocking layer may be from about 20 Å to about 1000 Å, for example about 30 Å to about 300 Å. When the thickness of the hole blocking layer is within these ranges, the hole blocking layer may have improved hole blocking ability without a substantial increase in driving voltage.

The electron transport layer may further include at least one of the BCP, Bphen and the following Alq$_3$, Balq, TAZ, and NTAZ.

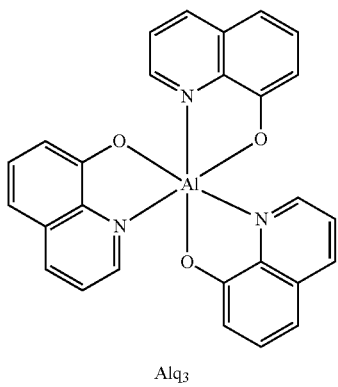

Alq₃

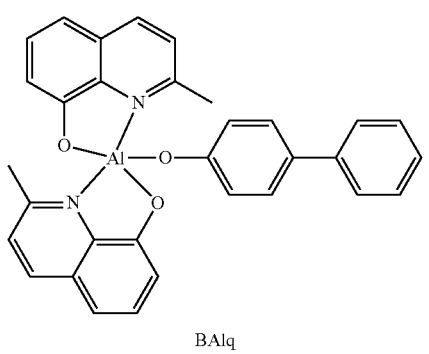

BAlq

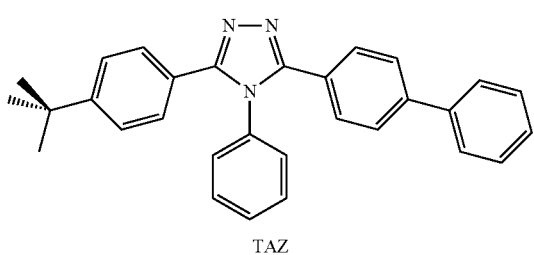

TAZ

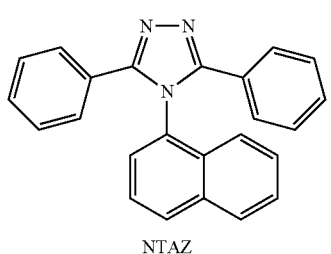

NTAZ

Or, the electron transport layer may include at least one of Compounds ET1 and ET2, but is not limited thereto.

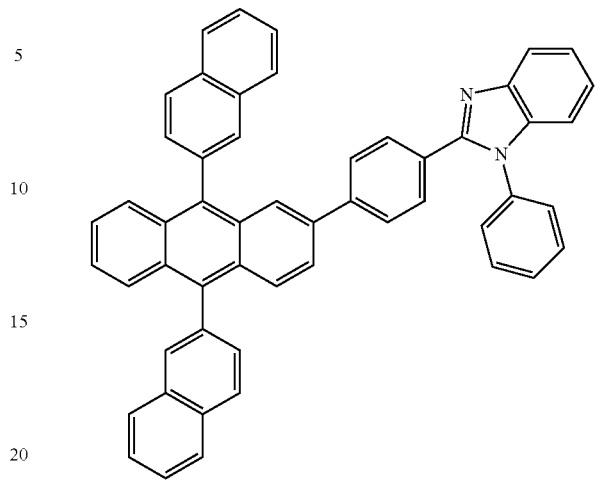

ET1

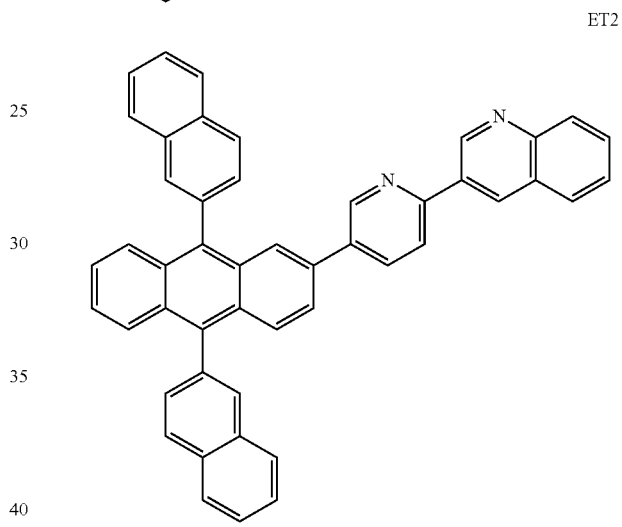

ET2

Å thickness of the electron transport layer may be about 100 Å to about 1000 Å, for example about 150 Å to about 500 Å. When the thickness of the electron transport layer is within these ranges, the electron transport layer may have satisfactory electron transporting ability without a substantial increase in a driving voltage.

The electron transport layer may further include a metal-containing material, in addition to the above-described materials.

In addition, the electron transport region may include an electron injection layer (EIL) that may facilitate injection of electrons from the cathode 110.

The electron injection layer 36 is disposed on an electron transport layer and may play a role of facilitating an electron injection from a cathode and ultimately improving power efficiency and be formed by using any material used in a related art without a particular limit, for example, LiF, Liq, NaCl, CsF, Li₂O, BaO, and the like.

The electron injection layer may include at least one selected from LiF, NaCl, CsF, Li₂O, and BaO.

Å thickness of the electron injection layer may be from about 1 Å to about 100 Å, or about 3 Å to about 90 Å. When the thickness of the electron injection layer is within these ranges, the electron injection layer may have satisfactory electron injection ability without a substantial increase in driving voltage.

The cathode 110 is disposed on the organic layer 105. A material for the cathode 110 may be a metal, an alloy, or an electrically conductive compound that have a low work function, or a combination thereof. Specific examples of the material for the cathode 110 may be lithium (Li), magnesium (Mg), aluminum (Al), aluminum-lithium (Al—Li), calcium (Ca), magnesium-indium (Mg—In), magnesium-silver (Mg—Ag), etc. In order to manufacture a top-emission light-emitting device, the cathode 110 may be formed as a transmissive electrode from, for example, indium tin oxide (ITO) or indium zinc oxide (IZO).

The organic light emitting diode may be applied to an organic light emitting display device.

Hereinafter, the embodiments are illustrated in more detail with reference to examples. These examples, however, are not in any sense to be interpreted as limiting the scope of the invention (Synthesis of First Compound for Organic Optoelectric Device)

Hereinafter, starting materials and reactants used in Examples and Synthesis Examples were available from Sigma-Aldrich Co. Ltd. or TCI Inc. as far as there in no particular comment and may be easily synthesized as publicly known materials.

In the following Synthesis Examples, when "'B' is used instead of 'A'", the amounts of 'A' and 'B' are the same as based on a mole equivalent.

As specific examples of the compound for an organic optoelectric device of the present invention, the compound of Chemical Formula 1 was synthesized by the following Reaction Schemes.

Synthesis Example 1: Synthesis of Compound 1

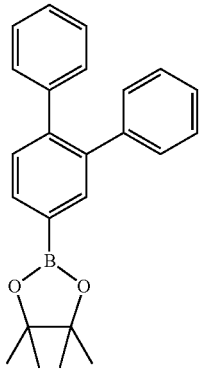

Intermediate 1-3

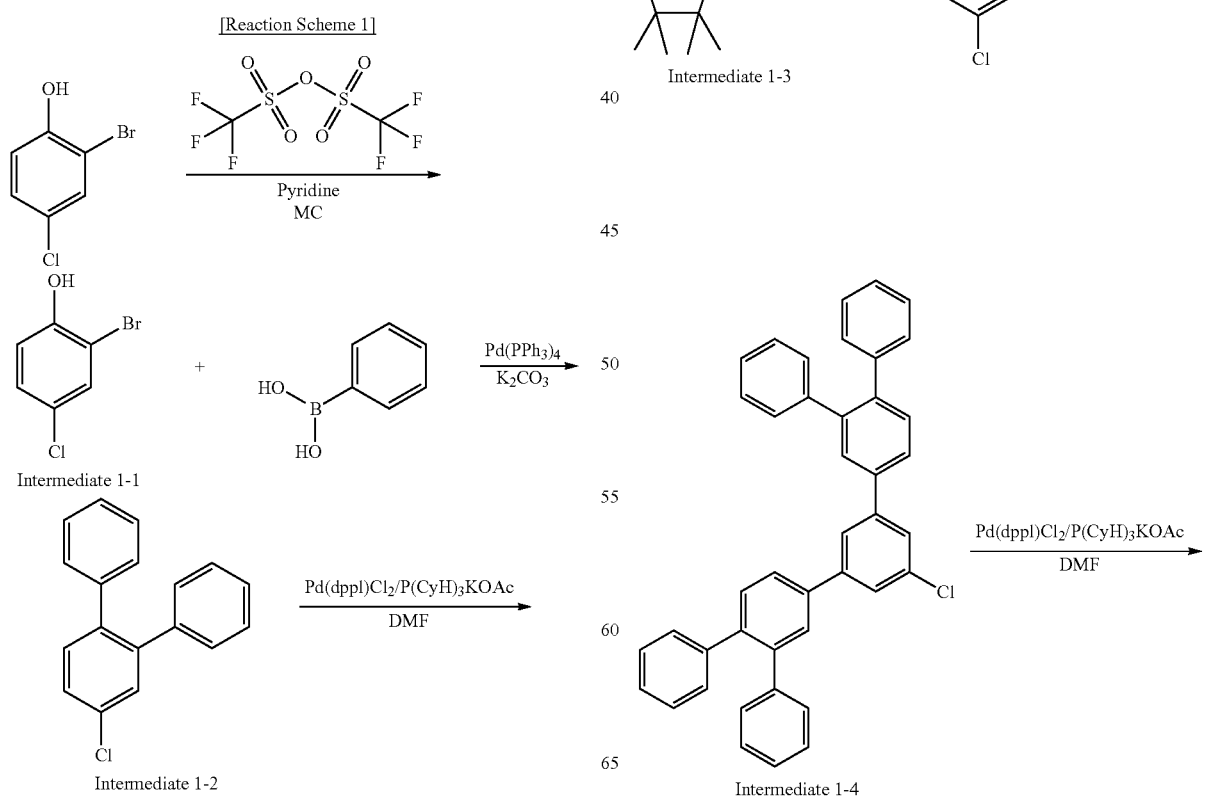

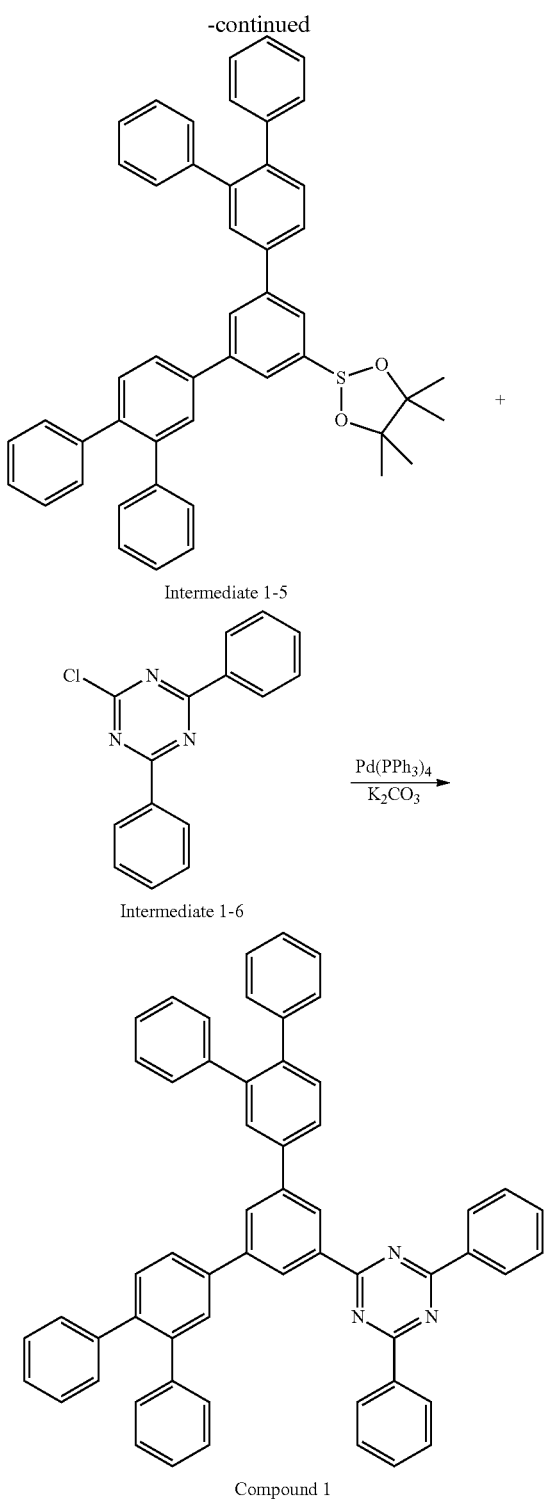

Intermediate 1-5

Intermediate 1-6

Compound 1

First Step: Synthesis of Intermediate 1-1

200.0 g (0.96 mol) of 2-bromo-4-chlorophenol and 155.3 g (0.16 mol) of pyridine were added to 2500 mL of methylene chloride in a 5000 mL flask, and 177.5 g (1.06 mol) of trifluoromethanesulfoic anhydride was slowly added thereto in a dropwise fashion for 2 hours after decreasing a temperature down to −20° C. The resultant was reacted at room temperature under a nitrogen flow for 24 hours. When a reaction was complete, the reactant was added in a dropwise to ice/water to wash an organic material, and an organic layer therein was separated and then, concentrated after removing moisture with magnesium sulfate to obtain Intermediate 1-1 (320.8 g, yield of 98%).

calcd. C7H3BrClF3O3S: C, 24.76; H, 0.89; Br, 23.53; Cl, 10.44; F, 16.79; O, 14.14; S, 9.44; found: C, 24.75; H, 0.89; Br, 23.52; Cl, 10.45; F, 16.79; O, 14.14; S, 9.44.

Second Step: Synthesis of Intermediate 1-2

100.0 g (294.5 mmol) of Intermediate 1-1, 75.4 g (618.54 mmol) of phenylboronic acid, 101.8 g (736.4 mmol) of potassium carbonate, and 10.2 g (8.8 mmol) of tetrakis(triphenylphosphine) palladium (0) were added to 1000 mL of 1,4-dioxane and 500 mL of water in a 3000 mL flask, and the mixture was heated at 80° C. for 24 hours under a nitrogen flow. The obtained mixture was added to 3000 mL of methanol to crystallize a solid, and the solid was filtered, dissolved in monochlorobenzene, filtered with silica gel/Celite, and then, recrystallized with methanol after removing an appropriate amount of the organic solvent to obtain Intermediate 1-2 (68.8 g, yield of 78%).

calcd. C18H13Cl: C, 81.66; H, 4.95; Cl, 13.39; found: C, 81.65; H, 4.94; Cl, 13.39.

Third Step: Synthesis of Intermediate 1-3

60.0 g (226.6 mmol) of Intermediate 1-2, 69.1 g (271.9 mmol) of 4,4,4',4',5,5,5',5'-octamethyl-2,2'-bi(1,3,2-dioxaborolane), 66.7 g (279.9 mmol) of acetic acid potassium (KOAc), 11.1 g (13.6 mmol) of 1,1'-bis(diphenylphosphino)ferrocene-palladium (II) dichloride, and 19.1 g (34.00 mmol) of tricyclohexylphosphine were added to 500 mL of N,N-dimethylformamide in a 1 L flask, and the mixture was stirred at 130° C. for 24 hours. When a reaction was complete, the reaction solution was extracted with water and EA, and an organic layer therefrom was concentrated after removing moisture by using magnesium sulfate, and purified through column chromatography to obtain white solid Intermediate 1-3 (60.6 g, yield of 75%).

calcd. C24H25BO2: C, 80.91; H, 7.07; B, 3.03; O, 8.98; found: C, 80.91; H, 7.07; B, 3.03; O, 8.98.

Fourth Step: Synthesis of Intermediate 1-4

59.1 g (163.1 mmol) of Intermediate 1-3, 21.0 g (77.68 mmol) of 1,3-dibromo-5-chlorobenzene, 26.8 g (194.2 mmol) of potassium carbonate, and 2.7 g (2.3 mmol)tetrakis(triphenylphosphine) palladium (0) were added to 260 mL of 1,4-dioxane and 130 mL of water in a 1000 mL flask, and the mixture was heated at 80° C. under a nitrogen flow for 24 hours. The obtained mixture was added to 500 mL of methanol to crystallize a solid, and the solid was filtered, dissolved in monochlorobenzene, filtered with silica gel/Celite, and then, recrystallized with methanol after removing an appropriate amount of the organic solvent to obtain Intermediate 1-4 (33.6 g, yield of 76%).

calcd. C42H29Cl: C, 88.63; H, 5.14; Cl, 6.23; found: C, 88.62; H, 5.14; Cl, 6.23.

Fifth Step: Synthesis of Intermediate 1-5

33.0 g (57.98 mmol) of Intermediate 1-4, 17.7 g (59.58 mmol) of 4,4,4',4',5,5,5',5'-octamethyl-2,2'-bi(1,3,2-dioxaborolane), 17.07 g (173.95 mmol) of acetic acid potassium (KOAc), 2.84 g (3.48 mmol) of 1,1'-bis(diphenylphosphino)ferrocene-palladium (II) dichloride, and 4.88 g (8.70 mmol) of tricyclohexyiphosphine were added to 200 mL of N,N-dimethylformamide in a 500 mL flask, and the mixture was stirred at 130° C. for 24 hours. When a reaction was complete, the reaction solution was extracted with water and EA, and an organic layer therefrom was concentrated after removing moisture with magnesium sulfate and purified through column chromatography to obtain Intermediate 1-5 (26.8 g, yield of 70%).

calcd. C48H41BO2: C, 87.26; H, 6.26; B, 1.64; O, 4.84; found: C, 87.26; H, 6.26; B, 1.63; O, 4.84.

Sixth Step: Synthesis of Compound 1

5.0 g (7.57 mmol) of Intermediate 1-5, 2.03 g (7.57 mmol) of Intermediate 1-6, 2.6 g (18.9 mmol) of potassium carbonate, and 0.26 g (0.23 mmol) of tetrakis(triphenylphosphine) palladium (0) were added to 30 mL of 1,4-dioxane and 15 mL of water in a 100 mL flask, and the mixture was heated at 80° C. under a nitrogen flow for 24 hours. The obtained mixture was added to 100 mL of methanol to crystallize a solid, and the solid was dissolved in monochlorobenzene, filtered with silica gel/Celite, and then, recrystallized with methanol after removing an appropriate amount of the organic solvent to obtain the Compound 1 (4.0 g, 69%).

calcd. C57H39N3: C, 89.38; H, 5.13; N, 5.49; found: C, 89.38; H, 5.13; N, 5.49.

Synthesis Example 2: Synthesis of Compound 2

[Reaction Scheme 2]

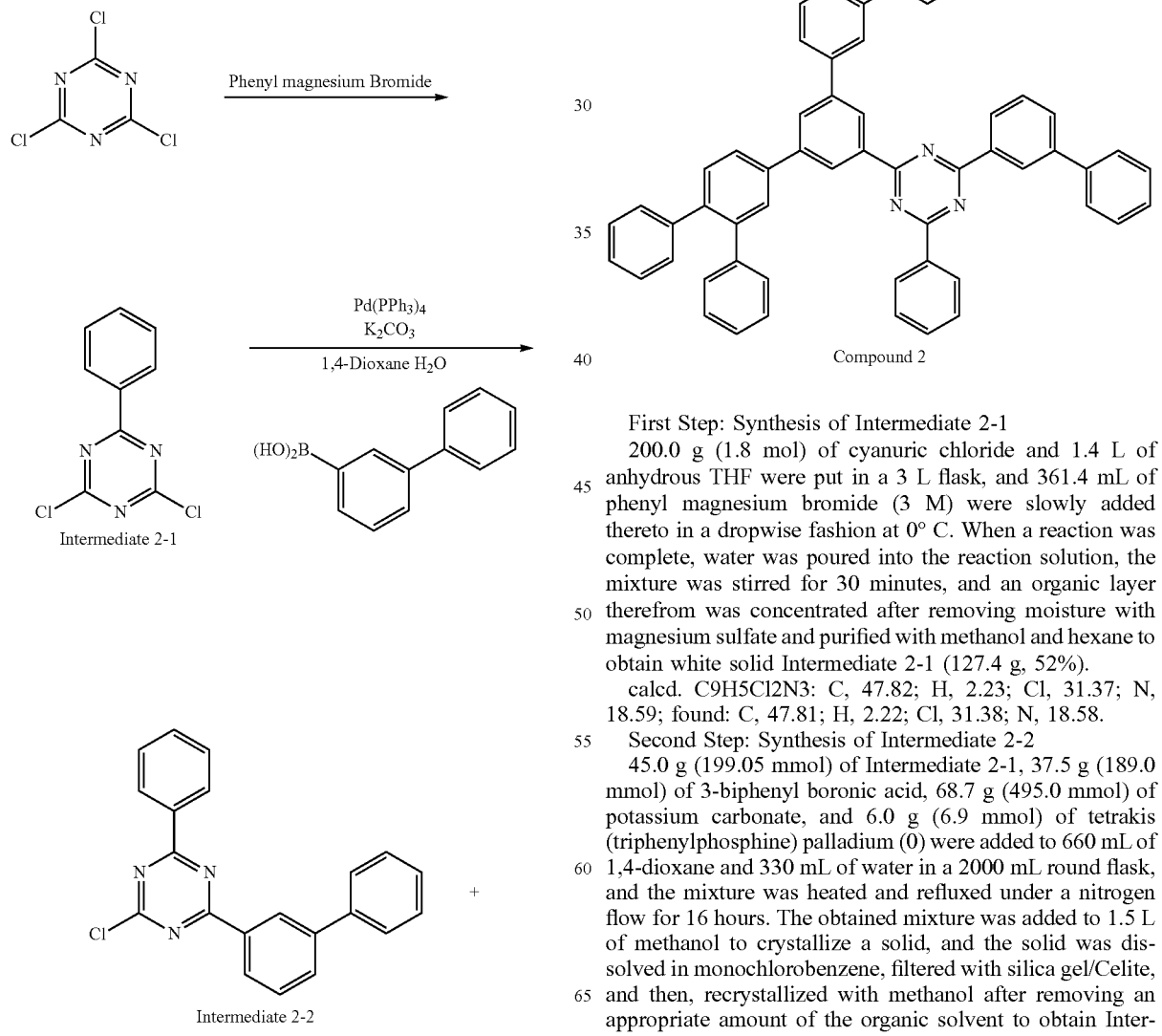

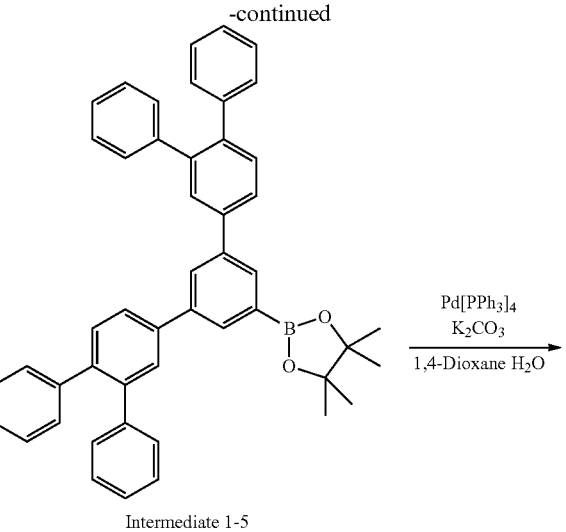

First Step: Synthesis of Intermediate 2-1

200.0 g (1.8 mol) of cyanuric chloride and 1.4 L of anhydrous THF were put in a 3 L flask, and 361.4 mL of phenyl magnesium bromide (3 M) were slowly added thereto in a dropwise fashion at 0° C. When a reaction was complete, water was poured into the reaction solution, the mixture was stirred for 30 minutes, and an organic layer therefrom was concentrated after removing moisture with magnesium sulfate and purified with methanol and hexane to obtain white solid Intermediate 2-1 (127.4 g, 52%).

calcd. C9H5Cl2N3: C, 47.82; H, 2.23; Cl, 31.37; N, 18.59; found: C, 47.81; H, 2.22; Cl, 31.38; N, 18.58.

Second Step: Synthesis of Intermediate 2-2

45.0 g (199.05 mmol) of Intermediate 2-1, 37.5 g (189.0 mmol) of 3-biphenyl boronic acid, 68.7 g (495.0 mmol) of potassium carbonate, and 6.0 g (6.9 mmol) of tetrakis (triphenylphosphine) palladium (0) were added to 660 mL of 1,4-dioxane and 330 mL of water in a 2000 mL round flask, and the mixture was heated and refluxed under a nitrogen flow for 16 hours. The obtained mixture was added to 1.5 L of methanol to crystallize a solid, and the solid was dissolved in monochlorobenzene, filtered with silica gel/Celite, and then, recrystallized with methanol after removing an appropriate amount of the organic solvent to obtain Intermediate 2-2 (47.7 g, yield of 70%).

calcd. C21H14ClN3: C, 73.36; H, 4.10; Cl, 10.31; N, 12.22; found: C, 73.36; H, 4.11; Cl, 10.30; N, 12.23.

Third Step: Synthesis of Compound 2

3.0 g (8.73 mmol) of Intermediate 2-2, 5.76 g (8.73 mmol) of Intermediate 1-5, 3.0 g (21.8 mmol) of potassium carbonate, and 0.3 g (0.26 mmol) of tetrakis(triphenylphosphine) palladium (0) were added to 30 mL of 1,4-dioxane and 15 mL of water in a 100 mL flask, and the mixture was heated at 80° C. under a nitrogen flow for 24 hours. The obtained mixture was added to 100 mL of methanol to crystallize a solid, and the solid was filtered, dissolved in monochlorobenzene, filtered with silica gel/Celite, and then, recrystallized with methanol after removing an appropriate amount of the organic solvent to obtain Compound 2 (5.3 g, yield of 73%).

calcd. C63H43N3: C, 89.86; H, 5.15; N, 4.99; found: C, 89.86; H, 5.15; N, 4.99.

Synthesis Example 3: Synthesis of Compound 3

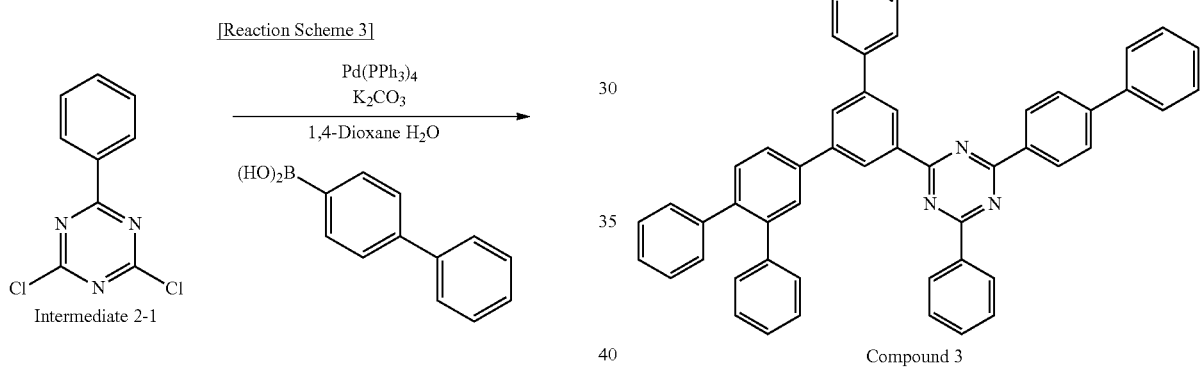

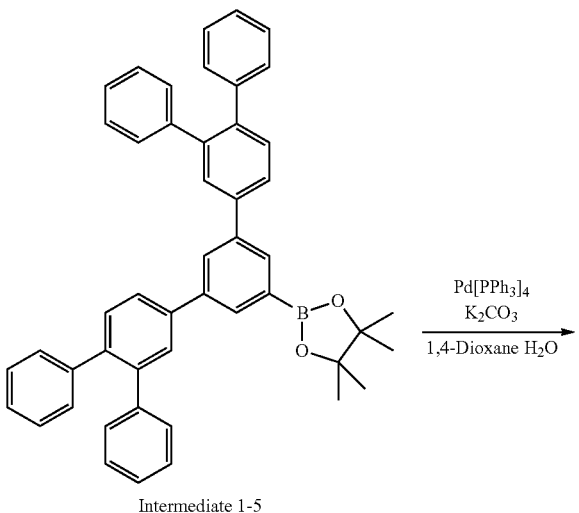

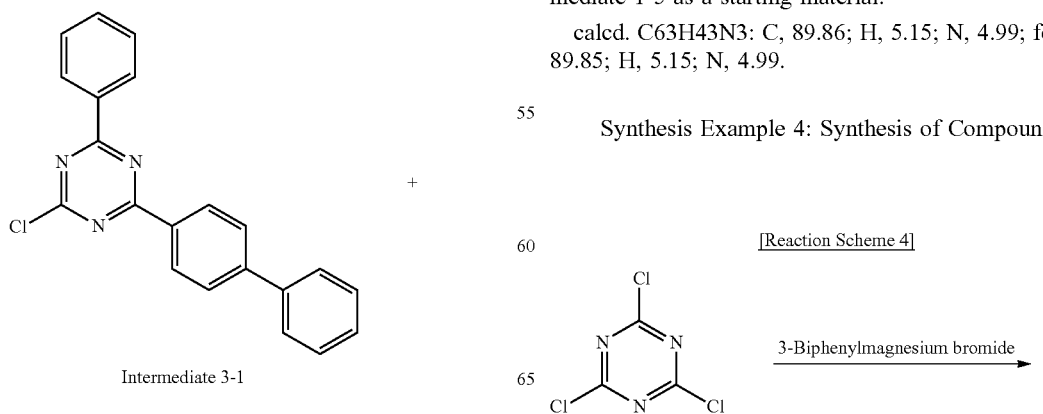

Intermediate 3-1 (43.0 g, yield of 63%) was obtained by using 4-biphenyl boronic acid instead of the 3-biphenylboronic acid in the second step of Synthesis Example 2 as a reactant.

Then, Compound 3 (5.1 g, yield of 70%) was obtained according to the same synthesis reaction as the third step of Synthesis Example 2 by using Intermediate 3-1 and Intermediate 1-5 as a starting material.

calcd. C63H43N3: C, 89.86; H, 5.15; N, 4.99; found: C, 89.85; H, 5.15; N, 4.99.

Synthesis Example 4: Synthesis of Compound 5

[Reaction Scheme 4]

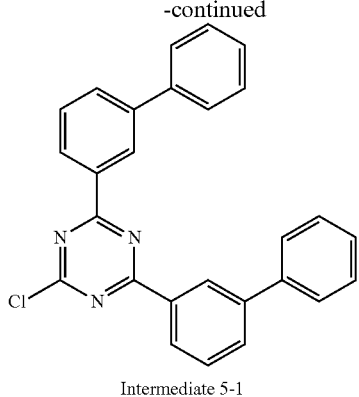

Intermediate 5-1

+

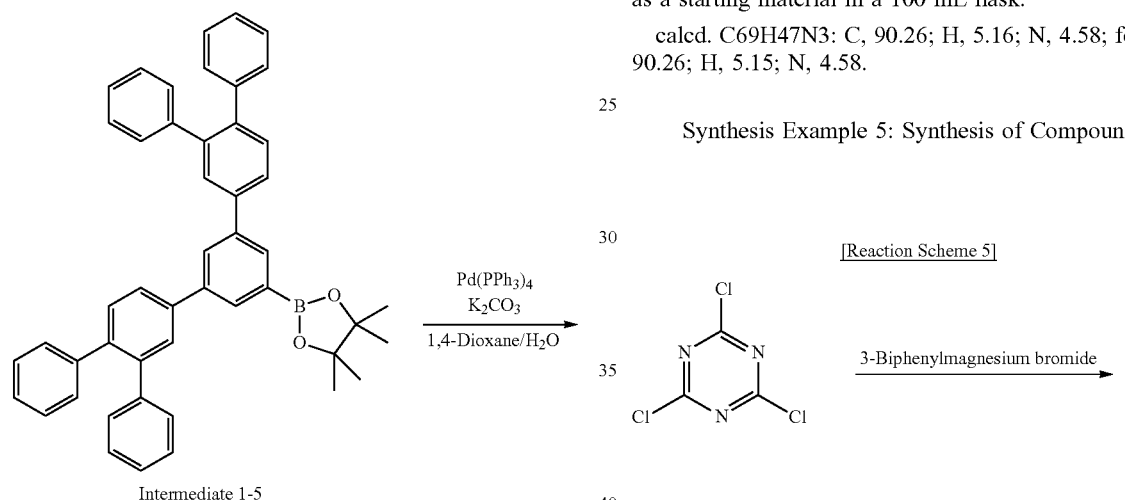

Intermediate 1-5

Compound 5

First Step: Synthesis of Intermediate 5-1

100.0 g (542.3 mmol) of cyanuric chloride and 700 mL of anhydrous THF were put in a 2 L flask, 361.4 mL of 3-Biphenylmagnesium bromide (3 M) was added thereto, and the mixture was slowly added thereto in a dropwise fashion at 0° C. When a reaction was complete, water was poured into the reaction solution, the mixture was stirred for 30 minutes, and an organic layer therefrom was separated, concentrated after removing moisture by using magnesium sulfate, and purified with methanol and hexane to obtain white solid Intermediate 5-1 (122.9 g, yield of 55%).

calcd. C27H18ClN3: C, 77.23; H, 4.32; Cl, 8.44; N, 10.01; found: C, 77.25; H, 4.31; Cl, 8.44; N, 10.00.

Second Step: Synthesis of Compound 5

Compound 5 (4.3 g, yield of 65%) was obtained according to the same synthesis reaction as the third step of Synthesis Example 2 by using the 3.0 g (7.14 mmol) of Intermediate 5-1 and 4.72 g (7.14 mmol) of Intermediate 1-5 as a starting material in a 100 mL flask.

calcd. C69H47N3: C, 90.26; H, 5.16; N, 4.58; found: C, 90.26; H, 5.15; N, 4.58.

Synthesis Example 5: Synthesis of Compound 6

[Reaction Scheme 5]

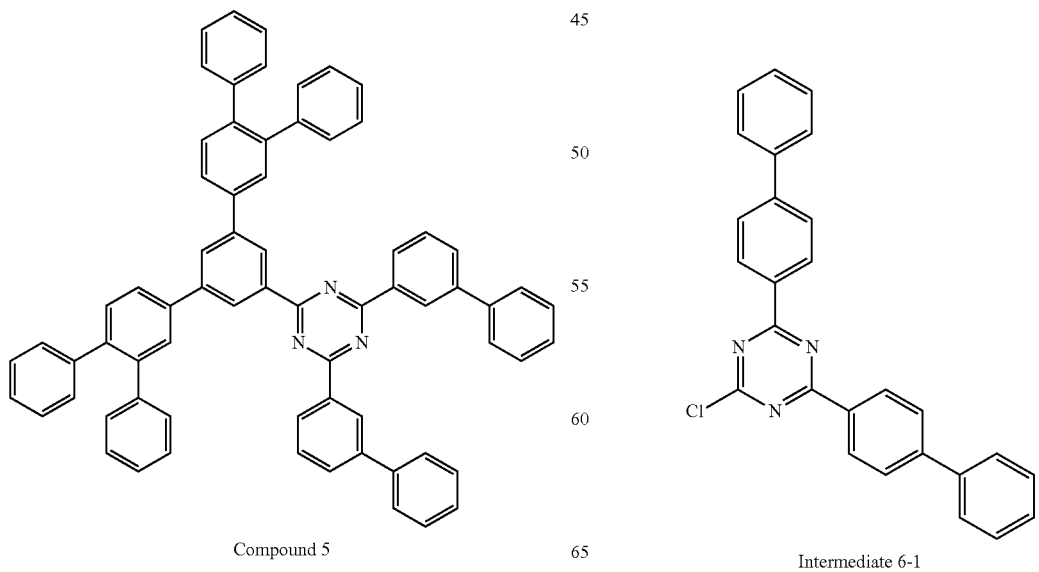

Intermediate 6-1

-continued

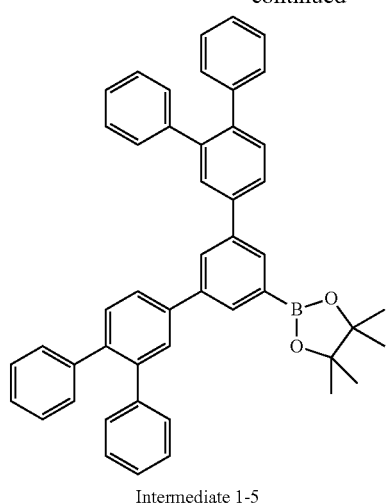

Intermediate 1-5

Compound 5

White solid Intermediate 6-1 (132.1 g, yield of 58%) was obtained in the first step of Synthesis Example 4 by using 4-biphenylmagnesium bromide instead of the 3-biphenylmagnesium bromide. Subsequently, Compound 6 (4.5 g, yield of 68%) as Intermediate 6-1 was synthesized according to the same synthesis as the second step of Synthesis Example 4.

calcd. C69H47N3: C, 90.26; H, 5.16; N, 4.58; found: C, 90.25; H, 5.15; N, 4.58.

Synthesis Example 6: Synthesis of Compound 7

[Reaction Scheme 6]

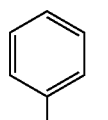

+

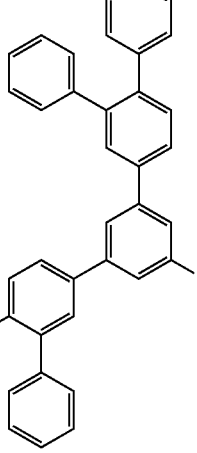

Intermediate 1-5

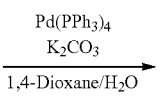

Compound 7

First Step: Synthesis of Compound 7

Compound 7 (5.94 g, yield of 69%) was obtained according to the same synthesis reaction as the third step of Synthesis Example 2 by using 3.0 g (11.25 mmol) of Intermediate 7-1 and 7.43 g (11.25 mmol) of Intermediate 1-5 in a 100 mL flask.

calcd. C58H40N2: C, 91.07; H, 5.27; N, 3.66; found: C, 91.08; H, 5.27; N, 3.66.

Synthesis Example 7: Synthesis of Compound 8

[Reaction Scheme 7]

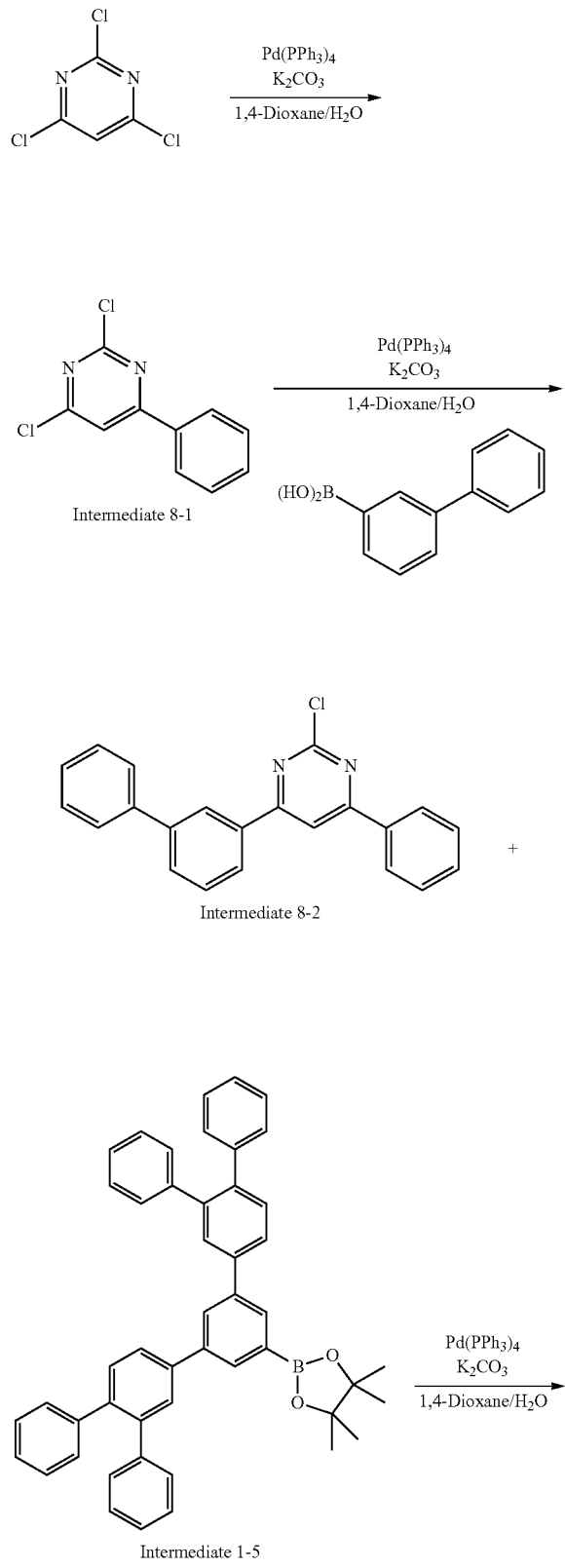

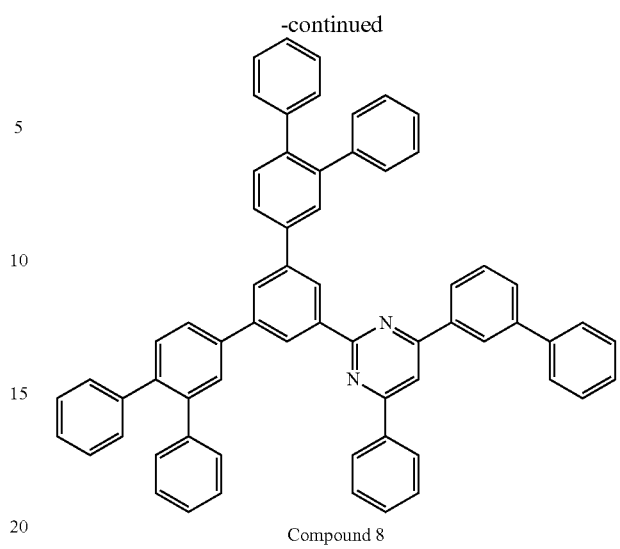

Compound 8

First Step: Synthesis of Intermediate 8-1

100.0 g (545.2 mmol) of 1,3,5-trichloro pyrimidine, 59.83 g (490.68 mmol) of phenylboronic acid, 188.38 g (1.36 mol) of potassium carbonate, and 18.90 g (16.36 mmol) of tetrakis(triphenylphosphine) palladium (0) were added to 800 mL of 1,4-dioxane and 400 mL of water in a 2 L flask, and the mixture was heated at 60° C. under a nitrogen flow for 12 hours. The obtained mixture was added to 2000 mL of methanol to crystallize a solid, and the solid was filtered, dissolved in monochlorobenzene, filtered with silica gel/ Celite, and then, recrystallized with methanol after removing an appropriate of the organic solvent to obtain Intermediate 8-1 (65.0 g, yield of 53%).

calcd. C10H6Cl2N2: C, 53.36; H, 2.69; Cl, 31.50; N, 12.45; found: C, 53.36; H, 2.69; Cl, 31.50; N, 12.44.

Second Step: Synthesis of Intermediate 8-2

20.0 g, (88.86 mmol) of Intermediate 8-1, 17.6 g (88.86 mmol) of 3-biphenyl boronic acid, 30.7 g (222.15 mol) of potassium carbonate, and 3.08 g (2.67 mmol) of tetrakis (triphenylphosphine) palladium (0) were added to 300 mL of 1,4-dioxane and 150 mL of water in a 1 L flask, and the mixture was heated at 80° C. under a nitrogen flow for 12 hours. The obtained mixture was added to 1000 mL of methanol to crystallize a solid, and the solid was filtered, dissolved in monochlorobenzene, filtered with silica gel/ Celite, and then, recrystallized with methanol after removing an appropriate amount of the organic solvent to obtain Intermediate 8-2 (20.7 g, yield of 68%).

calcd. C22H15ClN2: C, 77.08; H, 4.41; Cl, 10.34; N, 8.17; found: C, 77.08; H, 4.41; Cl, 10.33; N, 8.16.

Third Step: Synthesis of Compound 8

Compound 8 (8.8 g, yield of 72%) was obtained according to the same method as the third step of Synthesis Example 2 by reacting 5.0 g (14.58 mmol) of Intermediate 8-2 and 9.64 g (14.58 mmol) of Intermediate 1-5 in a 100 mL flask.

calcd. C64H44N2: C, 91.40; H, 5.27; N, 3.33; found: C, 91.41; H, 5.27; N, 3.32.

Synthesis Example 8: Synthesis of Compound 9

[Reaction Scheme 8]

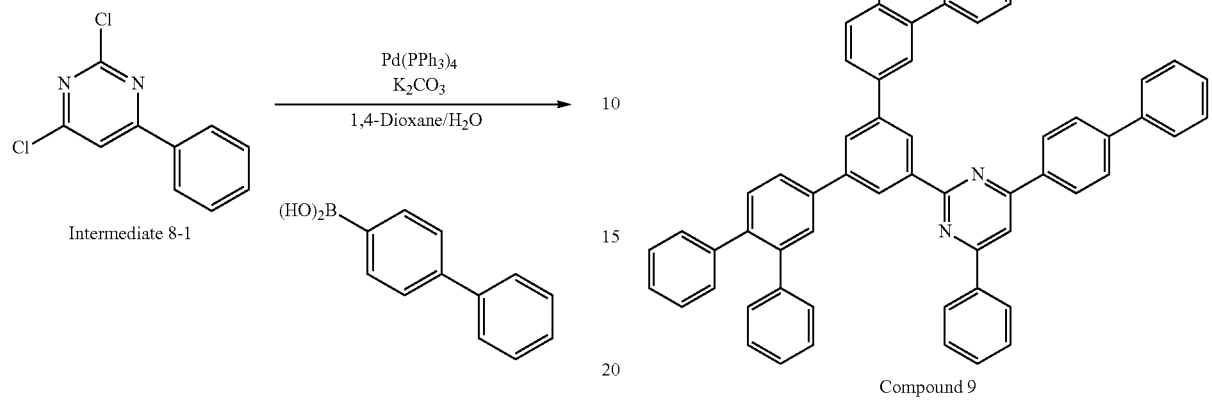

First Step: Synthesis of Intermediate 9-1

20.0 g (88.86 mmol) of Intermediate 8-1, 17.6 g (88.86 mmol) of 4-biphenyl boronic acid, 30.7 g (222.15 mol) of potassium carbonate, and 3.08 g (2.67 mmol) of tetrakis (triphenylphosphine) palladium (0) were added to 300 mL of 1,4-dioxane and 150 mL of water in a 1 L flask, and the mixture was heated at 80° C. under a nitrogen flow for 12 hours. The obtained mixture was added to 1000 mL of methanol to crystallize a solid, and the solid was filtered, dissolved in monochlorobenzene, filtered with silica gel/Celite, and then, recrystallized with methanol after removing an appropriate amount of the organic solvent to obtain Intermediate 9-1 (22.7 g, yield of 73%).

calcd. C22H15ClN2: C, 77.08; H, 4.41; Cl, 10.34; N, 8.17; found: C, 77.07; H, 4.40; Cl, 10.34; N, 8.16.

Second Step: Synthesis of Compound 9

Compound 9 (8.4 g, yield of 69%) was obtained according to the same method as the third step of Synthesis Example 2 by reacting 5.0 g (14.58 mmol) of Intermediate 9-1 and 9.64 g (14.58 mmol) of Intermediate 1-5 in a 100 mL flask.

calcd. C64H44N2: C, 91.40; H, 5.27; N, 3.33; found: C, 91.40; H, 5.27; N, 3.33.

Synthesis Example 9: Synthesis of Compound 11

[Reaction Scheme 9]

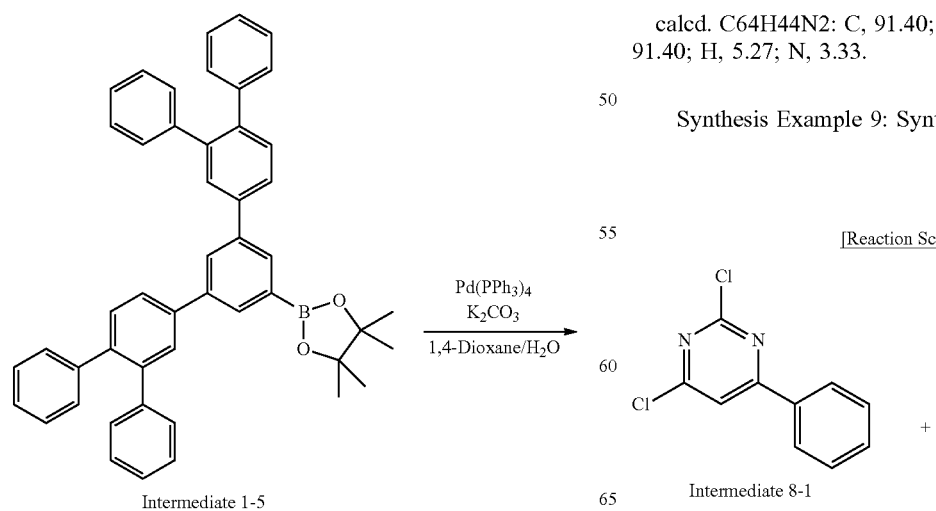

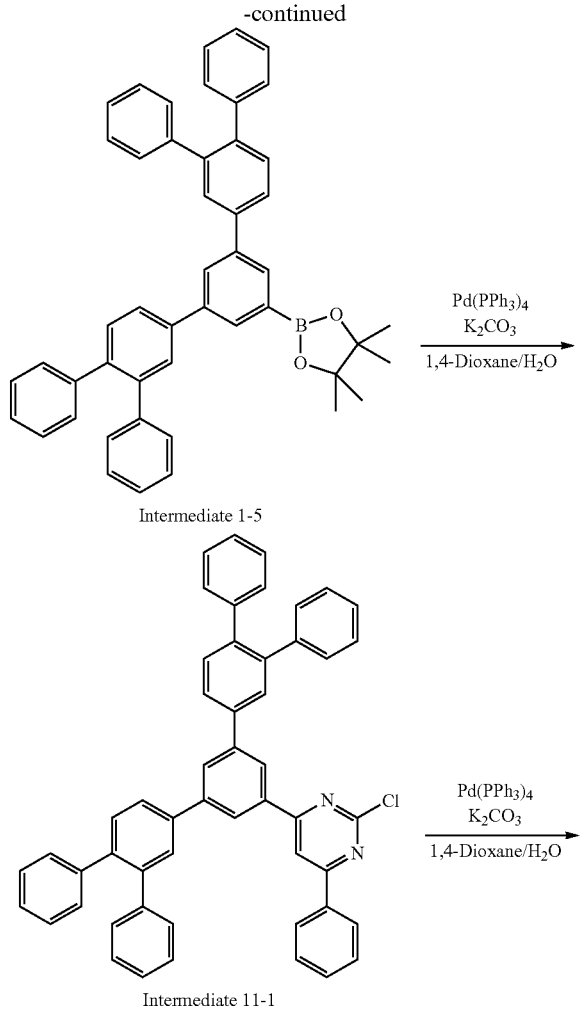

Intermediate 1-5

Intermediate 11-1

First Step: Synthesis of Intermediate 11-1

5.0 g (22.22 mmol) of Intermediate 8-1, 14.68 g (22.22 mmol) of Intermediate 1-5, 7.68 g (55.54 mmol) of potassium carbonate, and 0.77 g (0.67 mmol) of tetrakis(triphenylphosphine) palladium (0) were added to 80 mL of 1,4-dioxane and 40 mL of water in a 250 mL flask, and the mixture was heated at 60° C. under a nitrogen flow for 12 hours. The obtained mixture was added to 200 mL of methanol to crystallize a solid, and the solid was filtered, dissolved in monochlorobenzene, filtered with silica gel/Celite, and then, recrystallized with methanol after removing an appropriate amount of the organic solvent to obtain Intermediate 11-1 (10.44 g, yield of 65%).

calcd. C52H35ClN2: C, 86.35; H, 4.88; Cl, 4.90; N, 3.87; found: C, 86.35; H, 4.88; Cl, 4.90; N, 3.86.

Second Step: Synthesis of Compound 11

7.0 g (9.68 mmol) of Intermediate 11-1, 1.18 g (9.68 mmol) of phenylboronic acid, 3.34 g (24.19 mmol) of potassium carbonate, and 0.34 g (0.29 mmol) of tetrakis (triphenylphosphine) palladium (0) were added to 30 mL of 1,4-dioxane and 15 mL of water in a 100 mL flask, and the mixture was heated at 80° C. under a nitrogen flow for 12 hours. The obtained mixture was added to 100 mL of methanol to crystallize a solid, and the solid was filtered, dissolved in monochlorobenzene, filtered with silica gel/Celite, and then, recrystallized with methanol after removing an appropriate amount of the organic solvent to obtain Compound 11 (4.59 g, yield of 62%).

calcd. C58H40N2: C, 91.07; H, 5.27; N, 3.66; found: C, 91.07; H, 5.27; N, 3.66.

Synthesis Example 10: Synthesis of Compound 12

[Reaction Scheme 10]

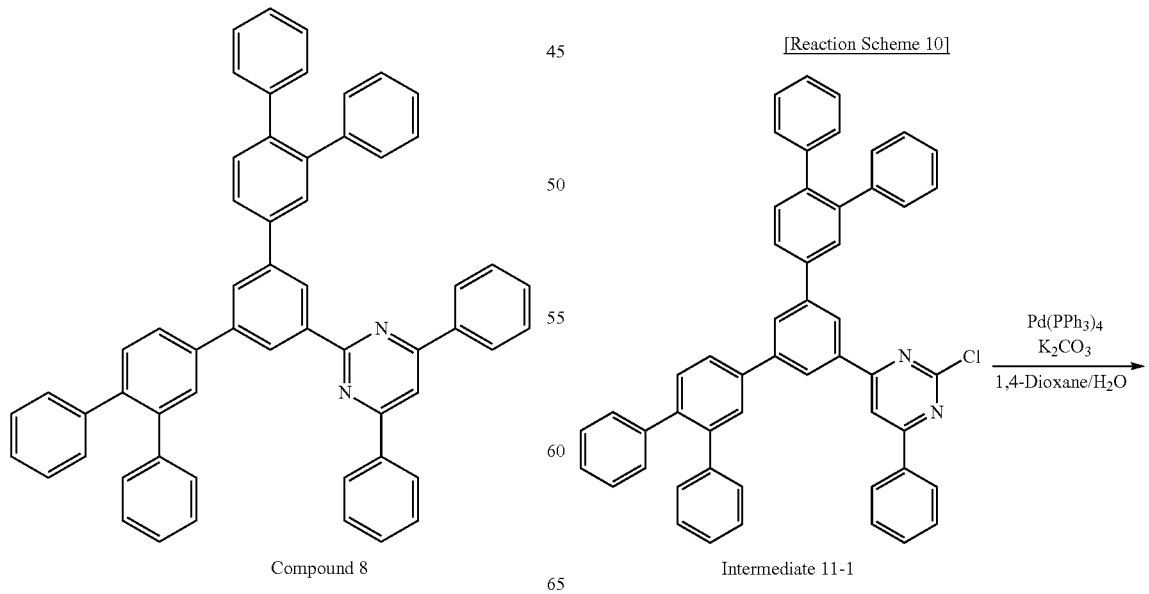

Compound 8

Intermediate 11-1

-continued

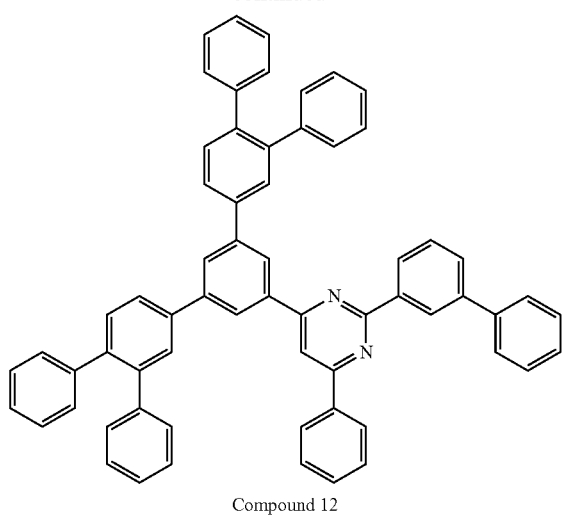

Compound 12

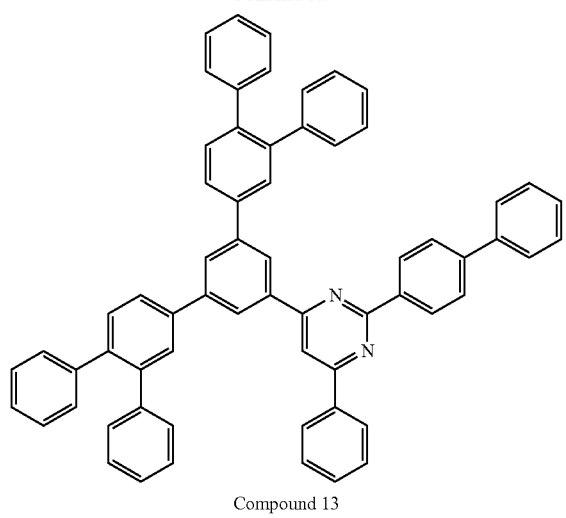

Compound 13

Compound 12 (5.45 g, yield of 67%) was obtained by using 3-biphenyl boronic acid instead of the phenylboronic acid in the second step of Synthesis Example 9.

calcd. C64H44N2: C, 91.40; H, 5.27; N, 3.33; found: C, 91.41; H, 5.26; N, 3.33.

Synthesis Example 11: Synthesis of Compound 13

Compound 13 (5.2 g, yield of 64%) was obtained by using 4-biphenyl boronic acid instead of the phenylboronic acid in the second step of Synthesis Example 9.

calcd. C64H44N2: C, 91.40; H, 5.27; N, 3.33; found: C, 91.40; H, 5.26; N, 3.33.

Synthesis Example 12: Synthesis of Compound 25

[Reaction Scheme 11]

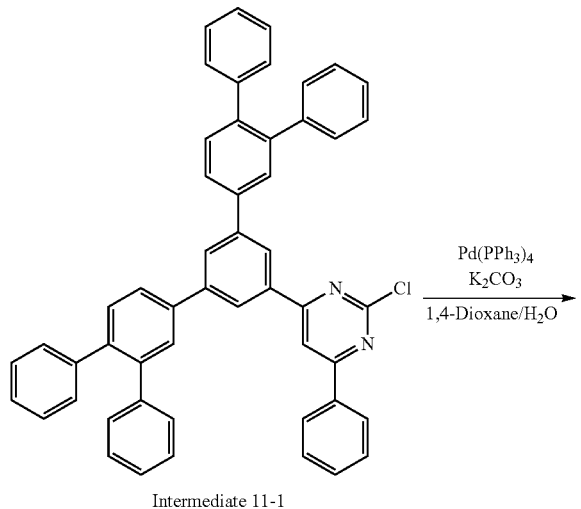

Intermediate 11-1

[Reaction Scheme 12]

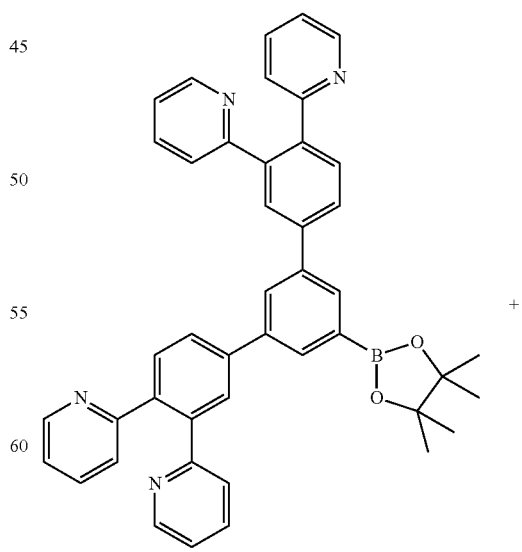

Intermediate 25-1

Synthesis Example 13: Synthesis of Compound 29

[Reaction Scheme 13]

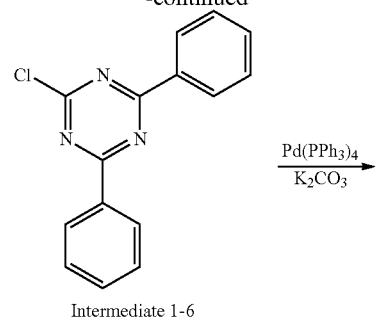

Intermediate 1-6

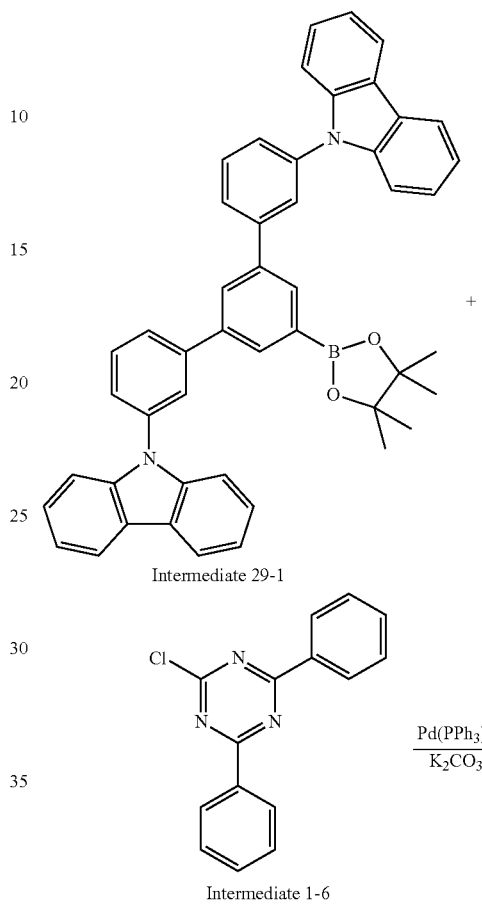

Intermediate 29-1

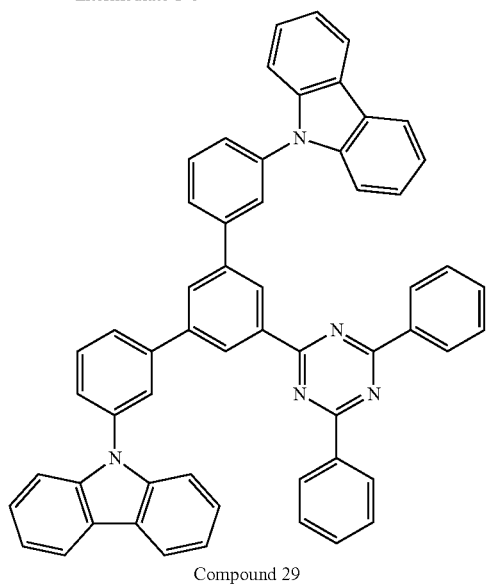

Compound 29

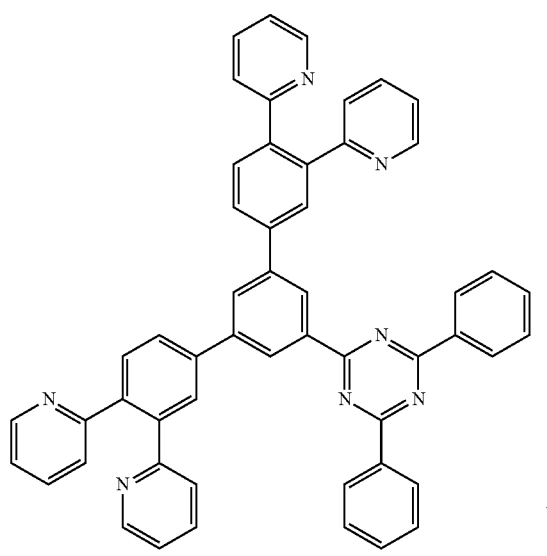

Compound 25

First Step: Synthesis of Intermediate 25-1

Intermediate 25-1 (25.2 g, yield of 66%) was obtained according to the same method as the method of synthesizing Intermediate 1-5 of Synthesis Example 1 except for using pyridineboronic acid instead of the phenylboronic acid as the reactant of the step 2 of Synthesis Example 1.

Second Step: Synthesis of Compound 25

10.0 g (15.05 mmol) of Intermediate 25-1, 4.03 g (15.05 mmol) of Intermediate 1-6, 5.20 g (37.62 mmol) of potassium carbonate, and 0.52 g (0.45 mmol) of tetrakis(triphenylphosphine) palladium (0) were added to 50 mL of 1,4-dioxane and 25 mL of water in a 250 mL flask, and the mixture was heated at 80° C. under a nitrogen flow for 12 hours. The obtained mixture was added to 150 mL of methanol to crystallize a solid, and the solid was filtered, dissolved in monochlorobenzene, filtered with silica gel/Celite, and then, recrystallized with methanol after removing an appropriate amount of the organic solvent to obtain Compound 25 (8.3 g, yield of 72%).

calcd. C53H35N7: C, 82.68; H, 4.58; N, 12.74; found: C, 82.68; H, 4.56; N, 12.74.

First Step: Synthesis of Intermediate 29-1

Intermediate 29-1 (21.5 g, yield of 63%) was obtained according to the same method as the method of synthesizing Intermediate 1-5 according to Synthesis Example 1 except for using 3-(9H-carbazole-9-yl)phenylboronic acid instead of Intermediate 1-3 as a starting material in the fourth step of Synthesis Example 1.

Second Step: Synthesis of Compound 29

7.0 g (10.19 mmol) of Intermediate 29-1, 2.73 g (10.19 mmol) of Intermediate 1-6, 3.52 g (25.49 mmol) of potassium carbonate, and 0.35 g (0.31 mmol) of tetrakis(triphenylphosphine) palladium (0) were added to 30 mL of 1,4-dioxane and 15 mL of water in a 100 mL flask, and the mixture was heated at 80° C. under a nitrogen flow for 12 hours. The obtained mixture was added to 100 mL of methanol to crystallize a solid, and the solid was dissolved in monochlorobenzene, filtered with silica gel/Celite, and then, recrystallized with methanol after removing an appropriate amount of the organic solvent to obtain Compound 29 (5.6 g, yield of 70%).

calcd. C57H37N5: C, 86.45; H, 4.71; N, 8.84; found: C, 86.44; H, 4.71; N, 8.84.

Synthesis Example 14: Synthesis of Compound 33

[Reaction Scheme 14]

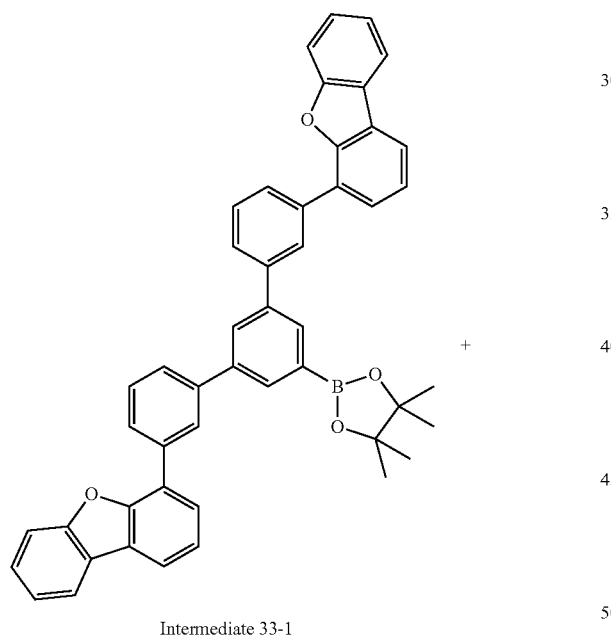

Intermediate 33-1

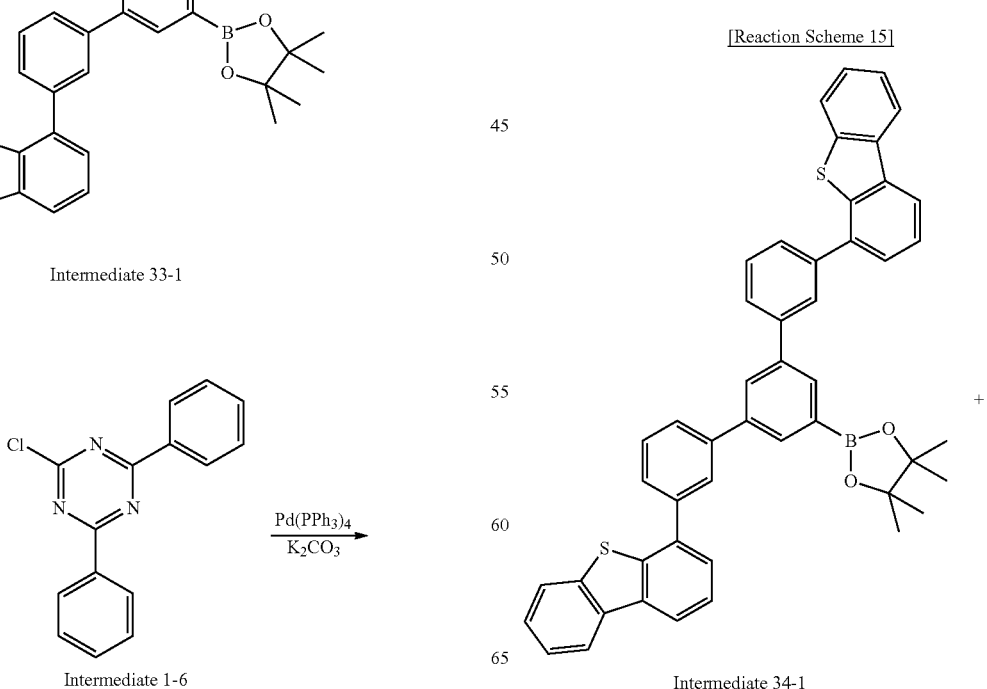

Intermediate 1-6

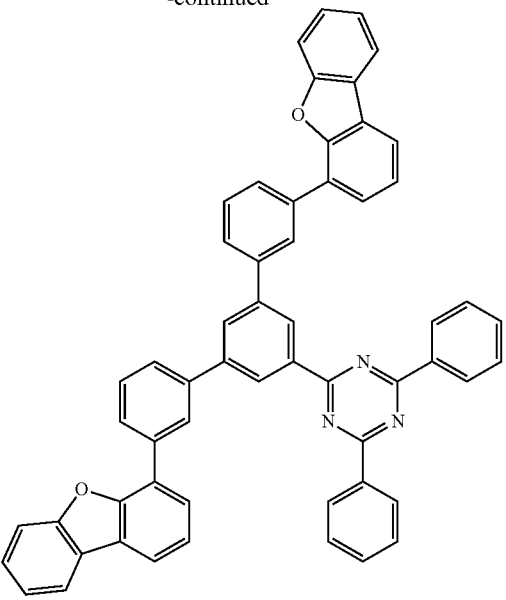

Compound 33

Intermediate 33-1 (27.1 g, yield of 63%) was synthesized according to the same method as the method of synthesizing Intermediate 1-5 according to Synthesis Example 1 by using 3-(dibenzofuran-4-yl)phenylboronic acid instead of Intermediate 1-3 as a starting material in the fourth step of Synthesis Example 1.

Compound 33 (5.3 g, yield of 66%) was obtained according to the same reaction as the second step of Synthesis Example 13 except for using Intermediate 33-1 instead of Intermediate 29-1.

calcd. C57H35N3O2: C, 86.23; H, 4.44; N, 5.29; O, 4.03; found: C, 86.23; H, 4.44; N, 5.28; O, 4.02.

Synthesis Example 15: Synthesis of Compound 34

[Reaction Scheme 15]

Intermediate 34-1

-continued

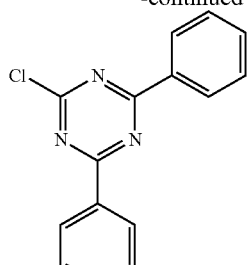

Intermediate 1-6

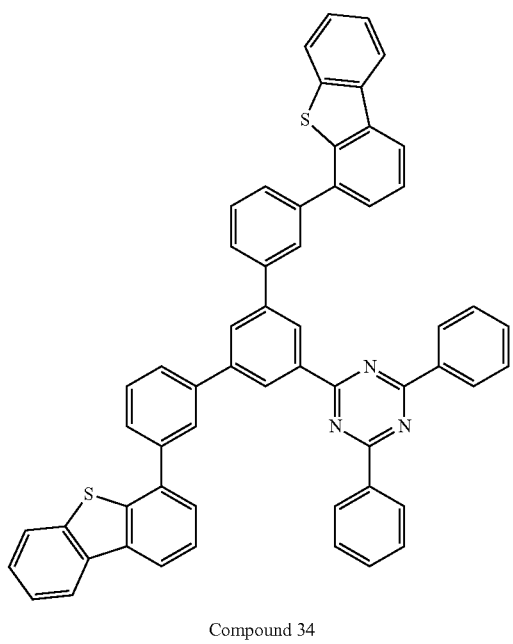

Compound 34

First Step: Synthesis of Intermediate 34-1

Intermediate 34-1 (15.8 g, yield of 66%) was synthesized according to the same method as the method of synthesizing Intermediate 1-5 of Synthesis Example 1 except for using 3-(dibenzothiophenyl-4-yl)phenylboronic acid instead of Intermediate 1-3 as a starting material in the fourth step of Synthesis Example 1.

Compound 34 (5.05 g, yield of 63%) was obtained according to the same method as the second step of Synthesis Example 13 except for using Intermediate 34-1 instead of Intermediate 29-1 of Synthesis Example 13.

calcd. C57H35N3S2: C, 82.88; H, 4.27; N, 5.09; S, 7.76; found: C, 82.88; H, 4.27; N, 5.09; S, 7.76.

Synthesis Example 16: Synthesis of Compound 50

[Reaction Scheme 16]

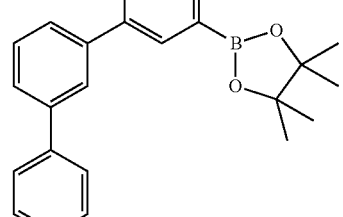

Intermediate 50-1

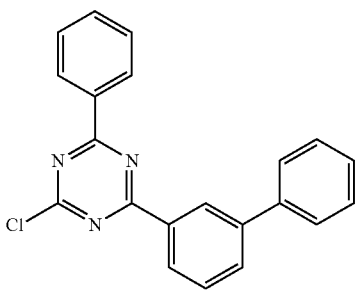

Intermediate 2-2

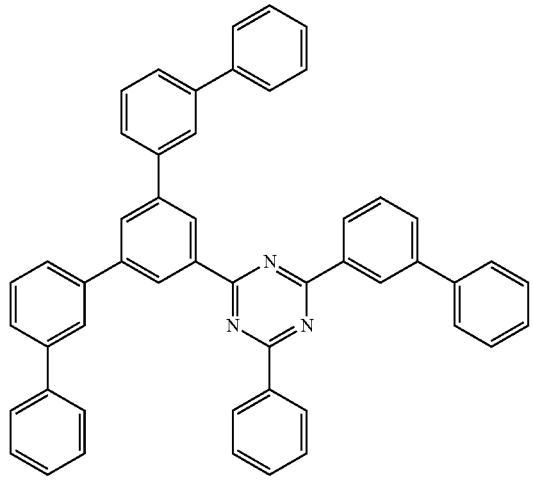

Compound 50

First Step: Synthesis of Intermediate 50-1

Intermediate 50-1 was synthesized according to the same method as the method of synthesizing Intermediate 1-5 of Synthesis Example 1 except for using biphenyl-3-boronic acid instead of Intermediate 1-3 as a starting material in the fourth step of Synthesis Example 1. (45.2 g, yield of 73%)

Second Step: Synthesis of Compound 50

Compound 50 (6.56 g, yield of 69%) was obtained according to the same as the second step of Synthesis Example 13 except for using Intermediate 50-1 instead of Intermediate 29-1 and Intermediate 2-2 instead of Intermediate 1-6.

calcd. C51H35N3: C, 88.79; H, 5.11; N, 6.09; found: C, 88.79; H, 5.11; N, 6.09.

(Synthesis of Second Compound for Organic Optoelectronic Device)

Synthesis Example 17: Synthesis of Compound B-129

[Reaction Scheme 17]

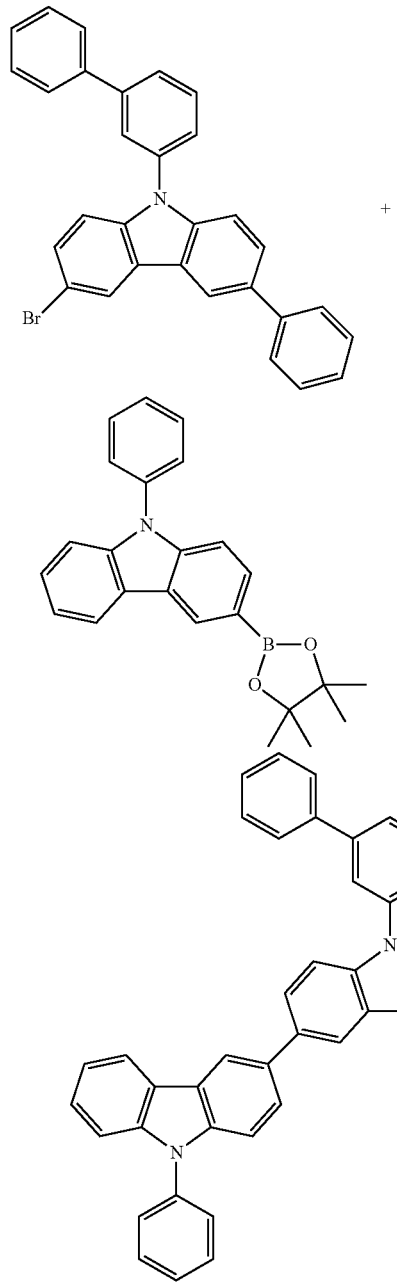

Compound B-129

20.00 g (42.16 mmol) of 3-bromo-6-phenyl-N-metabiphenylcarbazole and 17.12 g (46.38 mmol) of N-phenylcarbazole-3-boronic ester were mixed with 175 mL of tetrahydrofuran and toluene (1:1) and 75 mL of a 2 M-potassium carbonate aqueous solution under a nitrogen atmosphere in a 500 mL round-bottomed flask equipped with an agitator, 1.46 g (1.26 mmol) of tetrakistriphenylphosphinepalladium (0) was added thereto, and the mixture was heated and refluxed under a nitrogen flow for 12 hours. When a reaction was complete, the reactant was poured into methanol, and a solid therein was filtered, sufficiently cleaned with water and methanol, and dried. The resulting material was heated and dissolved in 700 mL of chlorobenzene, the solution was silica gel-filtered, and a filtrate therefrom was heated and dissolved in 400 mL of chlorobenzene after completely removing the solvent and then, recrystallized to obtain Compound B-129 (18.52 g, yield of 69%).

calcd. $C_{42}H_{32}N_2$: C, 90.54; H, 5.07; N, 4.40; found: C, 90.54; H, 5.07; N, 4.40.

Synthesis Example 18: Synthesis of Compound B-98

[Reaction Scheme 18]

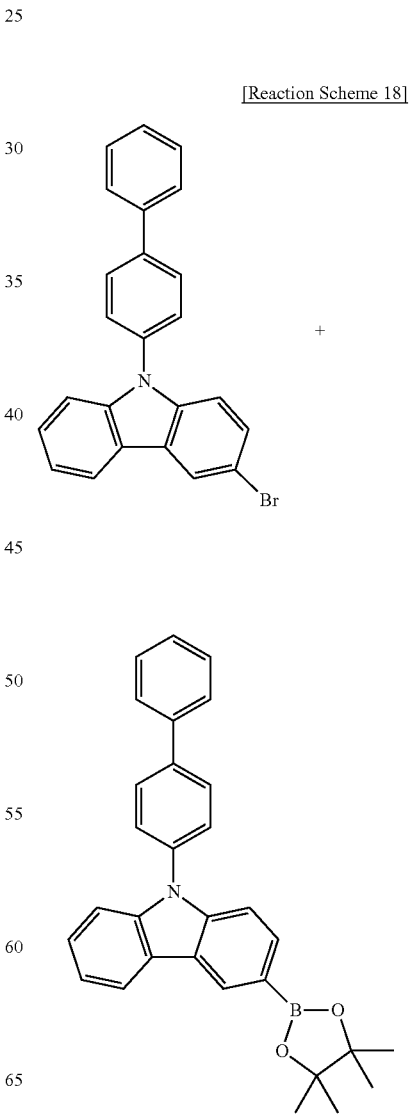

-continued

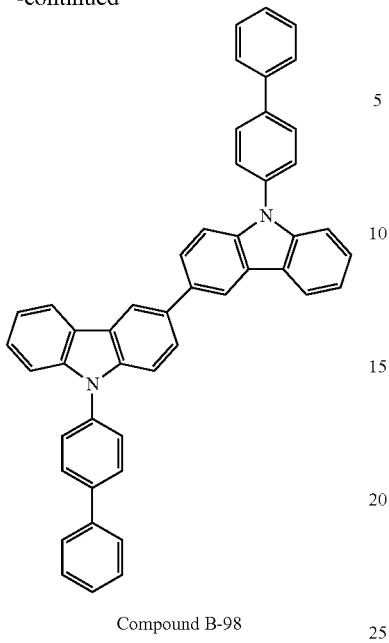

Compound B-98

15.00 g (37.66 mmol) of 3-bromo-N-biphenylcarbazole and 16.77 g (37.66 mmol) of 3-boronic ester-N-biphenyl carbazole were mixed with 200 mL of tetrahydrofuran and toluene (1:1) and 100 mL of a 2 M-potassium carbonate aqueous solution under a nitrogen atmosphere in a 500 mL round-bottomed flask equipped with an agitator, 2.18 g (1.88 mmol) of tetrakistriphenylphosphinepalladium (0) was added thereto, and the mixture was heated and refluxed under a nitrogen flow for 12 hours. When a reaction was complete, the reactant was poured into methanol, and a solid therein was filtered, sufficiently cleaned with water and methanol, and dried. The resulting material was dissolved in 500 mL of chlorobenzene, the solution was silica gel-filtered, and a filtrate therein was heated and dissolved in 400 mL of toluene after completely removing the solvent, and recrystallized to obtain Compound B-98 (16.54 g, yield of 69%).

calcd. $C_{48}H_{32}N_2$: C, 90.54; H, 5.07; N, 4.40; found: C, 90.52; H, 5.06; N, 4.42.

Synthesis Example 19: Synthesis of Compound B-136

[Reaction Scheme 19]

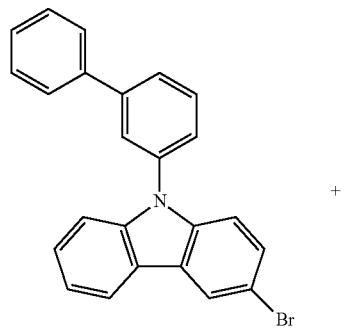

+

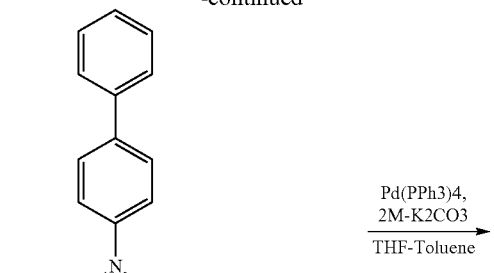

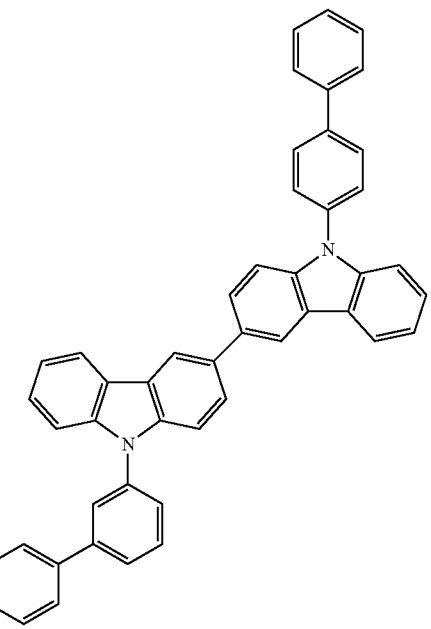

15.00 g (37.66 mmol) of 3-bromo-N-metabiphenylcarbazole and 16.77 g (37.66 mmol) of 3-boronic ester-N-biphenyl carbazole were mixed with 200 mL of tetrahydrofuran and toluene (1:1) and 100 mL of a 2 M-potassium carbonate aqueous solution in a 500 mL round-bottomed flask equipped with an agitator under a nitrogen atmosphere, 2.18 g (1.88 mmol) of tetrakistriphenylphosphinepalladium (0) was added thereto, and the mixture was heated and refluxed under a nitrogen flow for 12 hours. When a reaction was complete, the reactant was poured into methanol, and a solid therefrom was filtered, sufficiently cleaned with water and methanol, and dried. The obtained resulting material was dissolved in 500 mL of chlorobenzene, the solution was silica-gel filtered, and a filtrate therefrom was heated and dissolved in 400 mL of toluene after completely removing the solvent and recrystallized to obtain Compound B-136 (16.07 g, yield of 67%).

calcd. $C_{48}H_{32}N_2$: C, 90.54; H, 5.07; N, 4.40; found: C, 90.71; H, 5.01; N, 4.27.

Synthesis Example 20: Synthesis of Compound B-137

[Reaction Scheme 20]

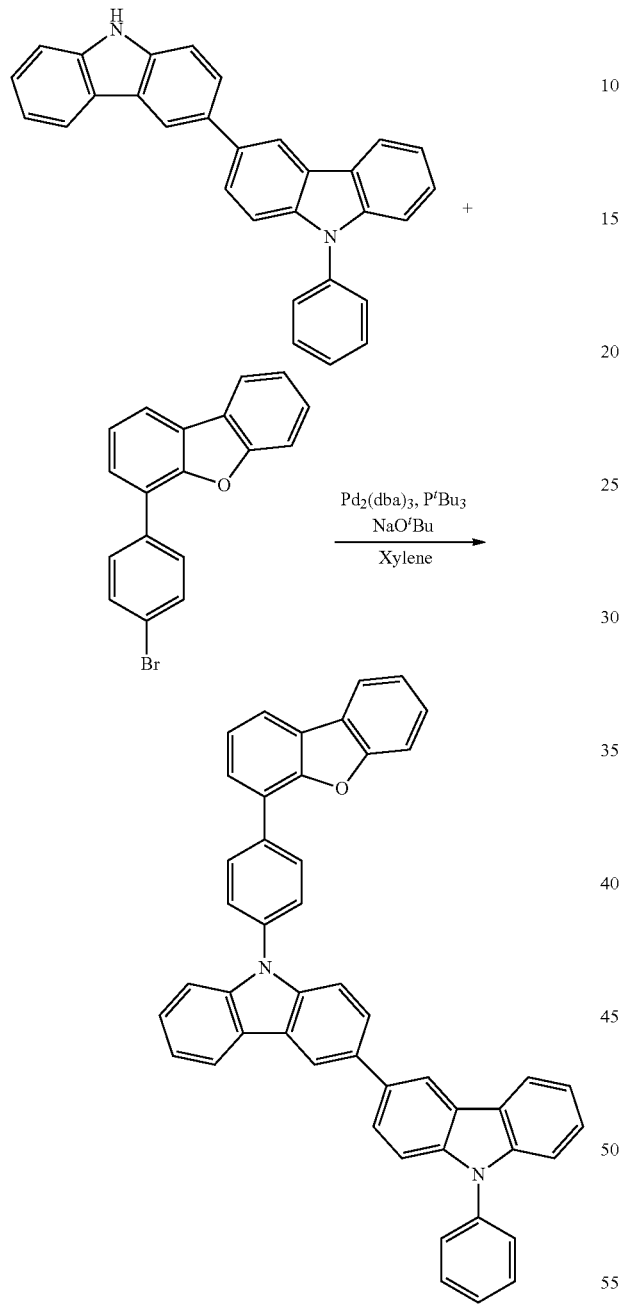

6.3 g (15.4 mmol) of N-phenyl-3,3-bicarbazole, 5.0 g (15.4 mmol) of 4-(4-bromophenyl)dibenzo[b,d]furan, 3.0 g (30.7 mmol) of sodium t-butoxide, 0.9 g (1.5 mmol) of tris(dibenzylideneacetone)dipalladium, and 1.2 mL of tri t-butylphosphine (50% in toluene) were mixed with 100 mL of xylene in a 250 mL round flask, and the mixture was heated and refluxed under a nitrogen flow for 15 hours. The obtained mixture was added to 300 mL of methanol, and a solid crystallized therein was filtered, dissolved in dichlorobenzene, filtered with silica gel/Celite, and then, recrystallized with methanol after removing an appropriate amount of the organic solvent to obtain Intermediate B-137 (7.3 g, yield of 73%).

calcd. C48H30N2O: C, 88.59; H, 4.65; N, 4.30; O, 2.46; found: C, 88.56; H, 4.62; N, 4.20; O, 2.43.

Comparative Synthesis Example 1: Compound a

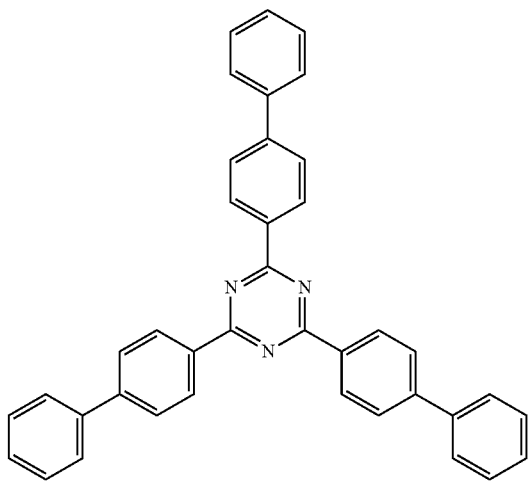 [SMILES: c1ccc(-c2ccc(-c3nc(-c4ccc(-c5ccccc5)cc4)nc(-c4ccc(-c5ccccc5)cc4)n3)cc2)cc1]

Comparative Synthesis Example 2: Compound b

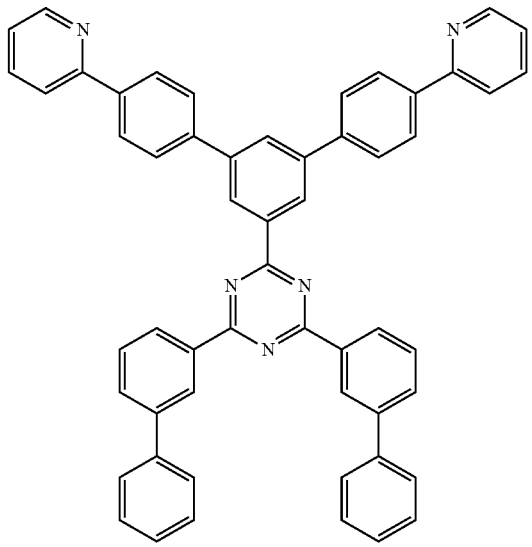 [SMILES: c1ccc(-c2cccc(-c3nc(-c4cccc(-c5ccccc5)c4)nc(-c4cc(-c5ccc(-c6ccccn6)cc5)cc(-c5ccc(-c6ccccn6)cc5)c4)n3)c2)cc1]

(Manufacture of Organic Light Emitting Diode)

Example 1

An organic light emitting diode was manufactured by using the compound 1 according to Synthesis Example 1 as a host and Ir(PPy)$_3$ as a dopant.

A 1000 Å-thick ITO was used as an anode, and a 1000 Å-thick aluminum (Al) as a cathode. Specifically, the organic light emitting diode was manufactured in a method of cutting an ITO glass substrate having sheet resistance of 15 Ω/cm² into a size of 50 mm×50 mm×0.7 mm, ultrasonic wave-cleaning it in acetone, isopropylalcohol, and pure water respectively for 15 minutes and UV ozone-cleaning it for 30 minutes.

On the substrate, an 800 Å-thick hole transport layer was formed by depositing N4,N4'-di(naphthalen-1-yl)-N4,N4'-diphenylbiphenyl-4,4'-diamine (NPB) (80 nm) under a vacuum degree of 650×10⁻⁷ Pa at a deposition rate of 0.1 to 0.3 nm/s. Subsequently, a 300 Å-thick film as an light-emitting layer was formed by using the compound 1 according to Synthesis Example 1 under the same vacuum deposition condition as above, and Ir(PPy)₃ as a phosphorescent dopant was simultaneously deposited. Herein, the phosphorescent dopant was deposited in an amount of 10 wt % based on 100 wt % of the total amount of the light-emitting layer by adjusting a deposition rate.

On the light-emitting layer, a 50 Å-thick film as a hole blocking layer was formed by depositing bis(2-methyl-8-quinolinolate)-4-(phenylphenolato)aluminum (BAlq) under the same vacuum deposition condition as above. Subsequently, a 200 Å-thick film as an electron transport layer was formed by depositing Alq3 under the same vacuum deposition condition as above. On the electron transport layer, LiF and Al were sequentially deposited as a cathode, manufacturing an organic light emitting diode.

A structure of the organic light emitting diode has ITO/NPB (80 nm)/EML (Compound 1 (90 wt %)+Ir(PPy)₃ (10 wt %), 30 nm)/BAlq (5 nm)/Alq3 (20 nm)/LiF (1 nm)/Al (100 nm).

Examples 2 to 16

Each organic light emitting diode of Example 2 to Example 16 was manufactured according to the same method as Example 1 by using Compounds 2, 3, 5 to 9, 11 to 13, 25, 29, 33, 34, and 50, respectively, instead of the Compound 1 of Synthesis Example 1.

Comparative Examples 1 and 2

Each organic light emitting diode of Comparative Examples 1 and 2 was manufactured according to the same method as Example 1 by using Compound a of Comparative Synthesis Example 1 and Compound b of Comparative Synthesis Example 2, instead of the Compound 1 of Synthesis Example 1.

Evaluation Example 1: Evaluation of Characteristics of Organic Light Emitting Diode (I)

Luminous efficiency and life-span characteristics of each organic light emitting diode according to Examples 1 to 16 and Comparative Examples 1 and 2 were evaluated.

Specific measurement methods are as follows, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm²) were calculated by using the luminance, current density, and voltages (V) from the items (1) and (2).

TABLE 1

| Nos. | Compounds | Dopant | Driving voltage (V) | Current efficiency (cd/A) | Color (EL color) |
|---|---|---|---|---|---|
| Example 1 | 1 | Ir(ppy)₃ | 3.88 | 42.5 | green |
| Example 2 | 2 | Ir(ppy)₃ | 3.81 | 44.7 | green |
| Example 3 | 3 | Ir(ppy)₃ | 3.79 | 43.5 | green |
| Example 4 | 5 | Ir(ppy)₃ | 3.69 | 43.3 | green |
| Example 5 | 6 | Ir(ppy)₃ | 3.64 | 45.5 | green |
| Example 6 | 7 | Ir(ppy)₃ | 4.28 | 41.9 | green |
| Example 7 | 8 | Ir(ppy)₃ | 4.15 | 42.5 | green |
| Example 8 | 9 | Ir(ppy)₃ | 4.09 | 42.0 | green |
| Example 9 | 11 | Ir(ppy)₃ | 4.23 | 42.5 | green |
| Example 10 | 12 | Ir(ppy)₃ | 4.11 | 43.1 | green |
| Example 11 | 13 | Ir(ppy)₃ | 4.04 | 43.4 | green |
| Example 12 | 25 | Ir(ppy)₃ | 3.57 | 43.3 | green |
| Example 13 | 29 | Ir(ppy)₃ | 4.00 | 47.1 | green |
| Example 14 | 33 | Ir(ppy)₃ | 3.93 | 46.3 | green |
| Example 15 | 34 | Ir(ppy)₃ | 3.91 | 45.8 | green |
| Example 16 | 50 | Ir(ppy)₃ | 4.04 | 43.1 | green |
| Comparative Example 1 | a | Ir(ppy)₃ | 4.35 | 35.5 | green |
| Comparative Example 2 | b | Ir(ppy)₃ | 4.03 | 39.9 | green |

Referring to Table 1, the organic light emitting diodes of Examples 1 to 16 according to an example embodiment of the present invention had a low driving voltage and high efficiency compared with the organic light emitting diodes of Comparative Examples 1 and 2.

The Compounds according to the embodiment of the present invention had excellent charge transport characteristics as a phosphorescent host material and were well overlapped with an absorption spectrum of a dopant and thus improved performance of increasing efficiency but decreasing a driving voltage and showed maximized capability as an OLED material.

Manufacture of Organic Light Emitting Diode (Light-Emitting Layer Device-Mixed Host)

Example 17

An organic light emitting diode was manufactured according to the same method as Example 1 except for codepositing Ir(ppy)₃(dopant), Compound 1 (a first host), and Compound B-136 (a second host) in a weight ratio of 10:45:45 on a hole transport layer (HTL) to form a 400 Å-thick light-emitting layer.

Examples 18 to 26

Organic light emitting diodes of Examples 18 to 26 were manufactured according to the same method as Example 17 except for respectively using Compound 2, Compound 3, Compound 5, Compound 6, Compound 25, Compound 29, Compound 33, Compound 34, and Compound 50 as each first host during forming the light-emitting layer, instead of Compound 1.

Examples 27 to 31

Organic light emitting diodes of Examples 27 to 31 were manufactured according to the same method as Example 17 except for respectively using Compound 2, Compound 6, Compound 29, Compound 33, and Compound 34 as each first host and using B-98 as a second host during forming the light-emitting layer, instead of Compound 1.

Comparative Examples 3 and 4

Organic light emitting diodes of Comparative Example 3 and 4 were synthesized according to the same method as Example 17 except for respectively using Comparative Compound a or Comparative Compound b alone during forming the light-emitting layer, instead of a mixed host of Compound 1 and Compound B-136.

Evaluation Example 2: Evaluation of Characteristics of Organic Light Emitting Diode (II)

A driving voltage, efficiency, luminance, and a life-span of the organic light emitting diodes according to Examples 17 to 31 and Comparative Examples 3 and 4 were measured by supplying power from a current voltage meter (Keithley SMU 236) and using a luminance meter, PR650 Spectroscan Source Measurement Unit (Photo Research Inc.), and the results are shown in Table 2. A $T_{95}$ life-span was evaluated as time (hr) taken until 95% of luminance relative to 100% of initial luminance was obtained.

TABLE 2

| Examples | First host | Second host | Driving Voltage (V) | Current efficiency (cd/A) | Luminance (cd/m$^2$) |
|---|---|---|---|---|---|
| 17 | 1 | B-136 | 3.76 | 43.2 | 6000 |
| 18 | 2 | B-136 | 3.72 | 45.0 | 6000 |
| 19 | 3 | B-136 | 3.65 | 44.1 | 6000 |
| 20 | 5 | B-136 | 3.59 | 43.5 | 6000 |
| 21 | 6 | B-136 | 3.57 | 45.8 | 6000 |
| 22 | 25 | B-136 | 3.48 | 44.2 | 6000 |
| 23 | 29 | B-136 | 3.91 | 47.5 | 6000 |
| 24 | 33 | B-136 | 3.78 | 46.9 | 6000 |
| 25 | 34 | B-136 | 3.82 | 46.1 | 6000 |
| 26 | 50 | B-136 | 3.89 | 44.1 | 6000 |
| 27 | 2 | B-98 | 3.68 | 45.2 | 6000 |
| 28 | 6 | B-98 | 3.54 | 45.8 | 6000 |
| 29 | 29 | B-98 | 3.77 | 47.6 | 6000 |
| 30 | 33 | B-98 | 3.68 | 47.0 | 6000 |
| 31 | 34 | B-98 | 3.74 | 46.4 | 6000 |
| Comparative Example 3 | Compound a | | 4.41 | 36 | 6000 |
| Comparative Example 4 | Compound b | | 4.14 | 35 | 6000 |

Referring to Table 2, the organic light emitting diodes of Examples 17 to 31 used both first and second host materials, which were the compounds of the present invention, and thus had a low driving voltage or high efficiency.

Manufacture of Organic Light Emitting Diode (ETB Device)

Example 32

A glass substrate coated with ITO (indium tin oxide) as a 1500 Å-thick thin film was washed with distilled water. After washed with distilled water, the glass substrate was ultrasonic wave-washed with a solvent such as isopropyl alcohol, acetone, methanol, and the like and dried, moved to a plasma cleaner, cleaned with oxygen plasma for 10 minutes, and moved to a vacuum depositor. This obtained ITO transparent electrode was used as an anode, and HT13 was vacuum-deposited on the ITO substrate to form a 400 Å-thick hole injection and transport layer. Then, a 200 Å-thick light-emitting layer was formed on the hole transport layer by vacuum-depositing BH113 and BD370 (available from SFC Inc.) as a blue fluorescent light emitting host and a dopant in a dopant concentration of 5 wt %. Then, on the light-emitting layer, 50 Å-thick electron transport auxiliary layer was formed by vacuum-depositing Compound 1 of Synthesis Example 1. On the electron transport auxiliary layer, a 310 Å-thick electron transport layer was formed by vacuum-depositing tris(8-hydroxyquinoline) aluminum (Alq3) and on the electron transport layer, a cathode was formed by sequentially vacuum-depositing Liq to be 15 Å thick and Al to be 1200 Å thick, manufacturing an organic light emitting diode.

The organic light emitting diode had a five-layered organic thin layer, and specifically ITO/HT13 1400 Å//EML[BH113:BD370=95:5 wt %] 200 Å/Compound 1 50 Å/Alq3 310 Å/Liq 15 Å/Al 1200 Å.

Examples 33 to 41

Organic light emitting diodes of Examples 33 to 41 were manufactured according to the same method as Example 32 except for respectively using Compound 2, Compound 3, Compound 5, Compound 6, Compound 25, Compound 29, Compound 33, Compound 34, and Compound 50, instead of Compound 1 of Example 32.

Comparative Example 5

An organic light emitting diode was manufactured according to the same method as Example 32 except for using no electron transport auxiliary layer.

Evaluation Example 3: Evaluation of Characteristics of Organic Light Emitting Diode (III)

Current density changes, luminance changes, and luminous efficiency of each organic light emitting diode according to Examples 32 to 41 and Comparative Example 5 were measured, and the results are shown in Table 3.

T97 life-spans of the organic light emitting diodes according to Examples 32 to 41, and Comparative Example 5 were measured as a time when their luminance decreased down to 97% relative to the initial luminance (cd/m$^2$) after emitting light with 750 cd/m$^2$ as the initial luminance (cd/m$^2$) and measuring their luminance decreases depending on a time with a Polanonix life-span measurement system.

TABLE 3

| Devices | Electron transport auxiliary layer | Driving voltage | Light emitting efficiency | Color coordinate (x, y) | T97 life-span (h)@750 nit |
|---|---|---|---|---|---|
| Example 32 | Compound 1 | 4.3 | 7.3 | (0.133, 0.147) | 175 |
| Example 33 | Compound 2 | 4.2 | 7.2 | (0.133, 0.147) | 172 |

TABLE 3-continued

| Devices | Electron transport auxiliary layer | Driving voltage | Light emitting efficiency | Color coordinate (x, y) | T97 life-span (h)@750 nit |
|---|---|---|---|---|---|
| Example 34 | Compound 3 | 4.2 | 6.8 | (0.133, 0.147) | 163 |
| Example 35 | Compound 5 | 4.0 | 7.3 | (0.133, 0.147) | 166 |
| Example 36 | Compound 6 | 4.2 | 7.2 | (0.133, 0.147) | 172 |
| Example 37 | Compound 25 | 4.0 | 7.2 | (0.133, 0.147) | 176 |
| Example 38 | Compound 29 | 4.4 | 6.9 | (0.133, 0.147) | 143 |
| Example 39 | Compound 33 | 4.4 | 7.1 | (0.133, 0.147) | 163 |
| Example 40 | Compound 34 | 4.5 | 7.2 | (0.133, 0.147) | 170 |
| Example 41 | Compound 50 | 4.4 | 7.0 | (0.133, 0.147) | 168 |
| Comparative Example 5 | Not used | 5.02 | 6.8 | (0.133, 0.147) | 126 |

Referring to Table 3, the organic light emitting diodes manufactured by using the compounds of the present invention of Examples 32 to 41 showed about 1.4 times longer life-span than the organic light emitting diode of Comparative Example 5.

Accordingly, life-span characteristics of the organic light emitting diodes were improved by the electron transport auxiliary layer.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS

100, 200, 300, 400: organic light emitting diode
105: organic layer
110: cathode
120: anode
130: light-emitting layer
140: hole auxiliary layer
10: organic light emitting diode
31: hole transport layer
33: hole transport auxiliary layer
34: electron transport layer
35: electron transport auxiliary layer
36: electron injection layer

What is claimed is:

1. A compound for an organic optoelectric device represented by Chemical Formula 1:

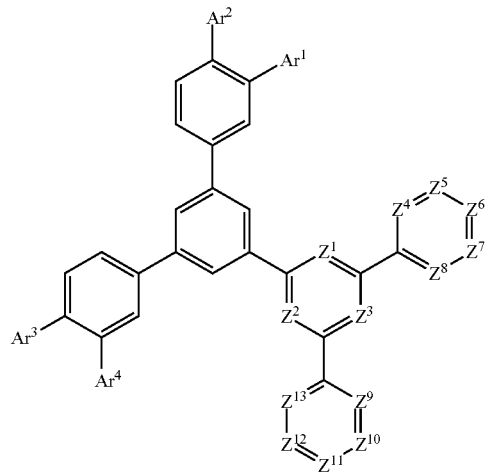

[Chemical Formula 1]

wherein, in Chemical Formula 1,

Ar$^1$ to Ar$^4$ are independently selected from substituents of Group I,

Z$^1$ to Z$^{13}$ are independently N or CR$^a$, provided that at least one of Z$^1$ to Z$^{13}$ is N, R$^a$ is independently hydrogen, deuterium, a substituted or unsubstituted C1 to C10 alkyl group, a C6 to C18 aryl group, or a combination thereof, and the "substituted" refers to replacement of at least one hydrogen by deuterium, a C1 to C4 alkyl group, or a C6 to C18 aryl group,

[Group I]

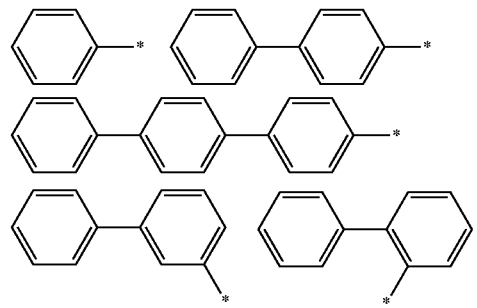

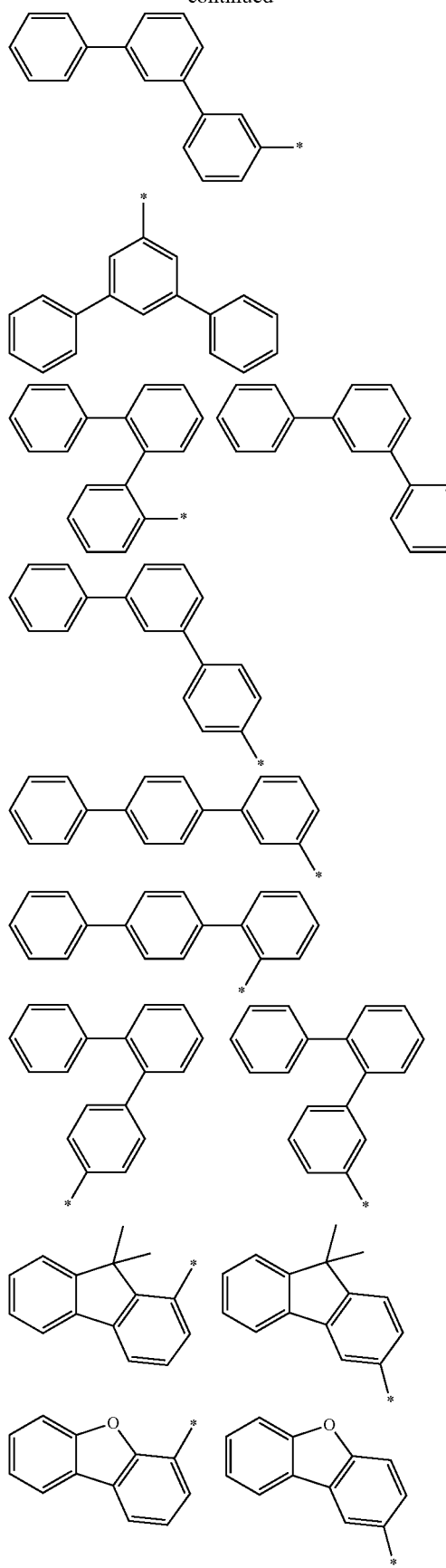
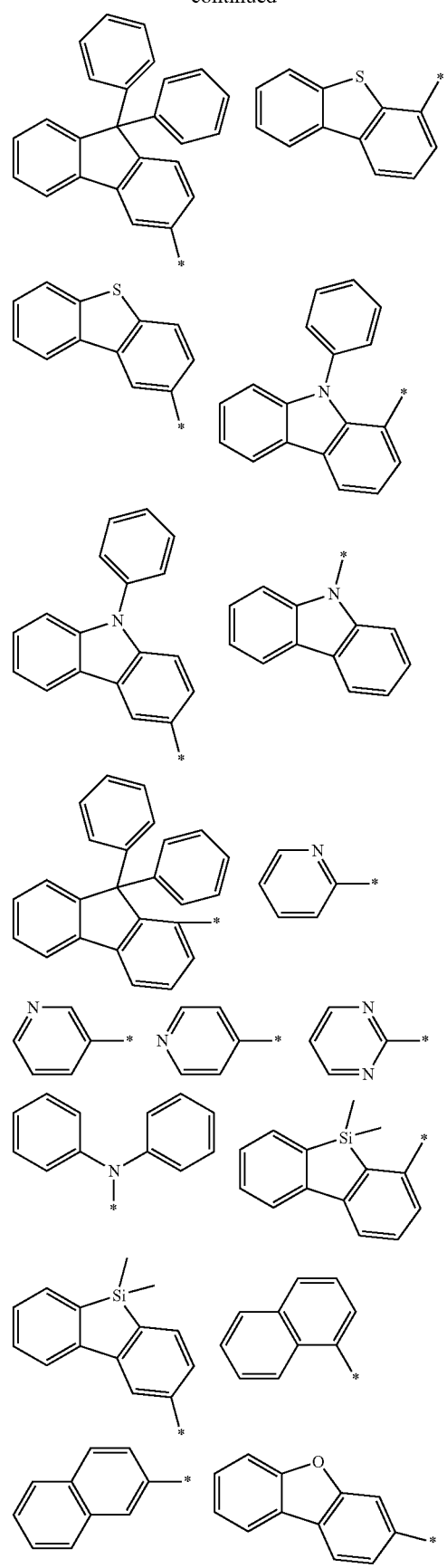

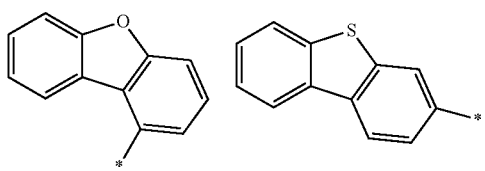
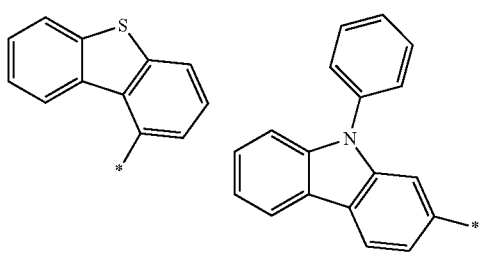
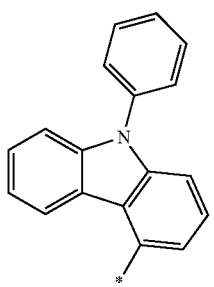
wherein, in Group I,
is a linking point.
2. The compound of claim 1, which is represented by Chemical Formula at least one of 1-A, 1-B, 1-C, 1-D, 1-E, 1-F, 1-G, 1-H, 1-I, or 1-J:
[Chemical Formula 1-A]
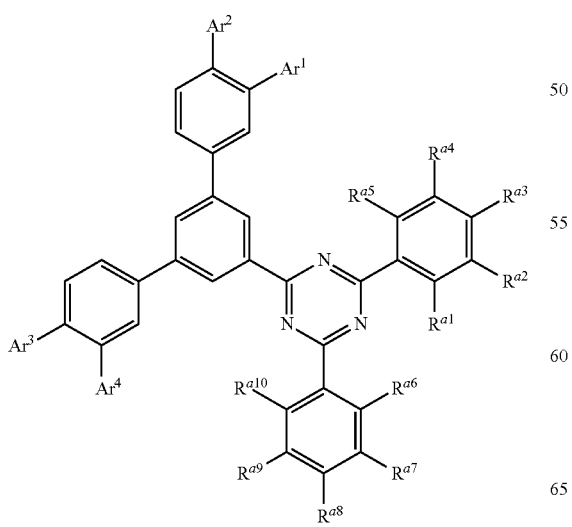
[Chemical Formula 1-B]
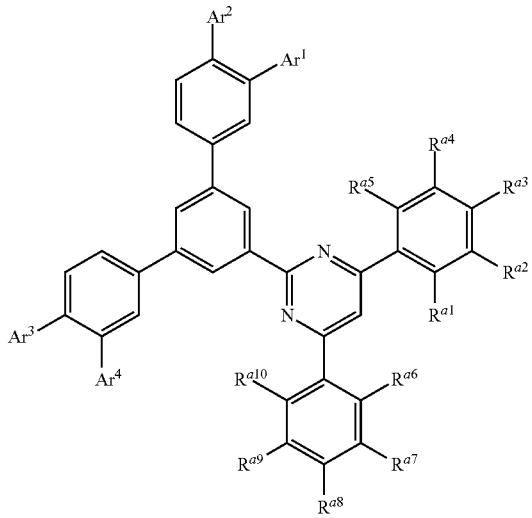
[Chemical Formula 1-C]
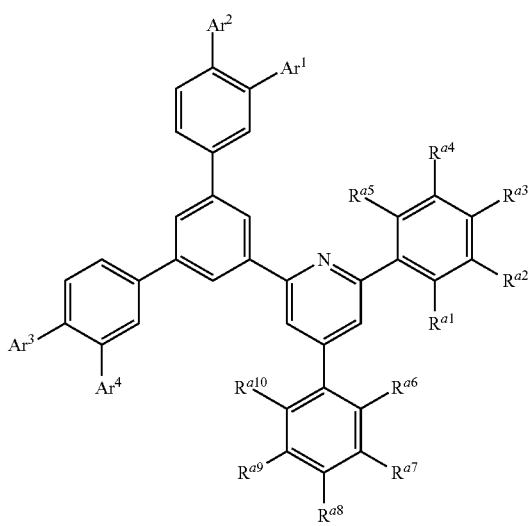
[Chemical Formula 1-D]

[Chemical Formula 1-E]
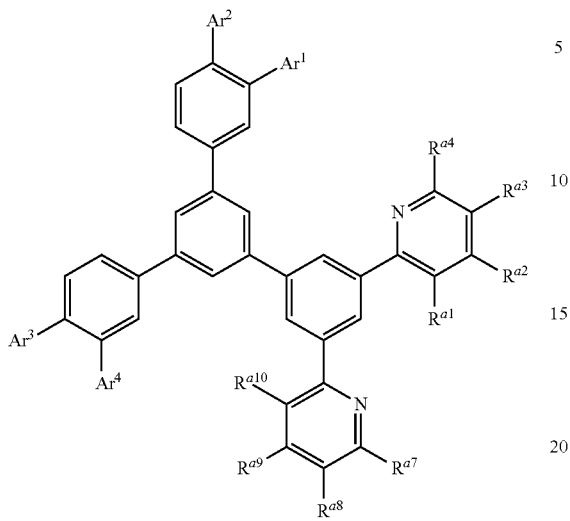
[Chemical Formula 1-F]
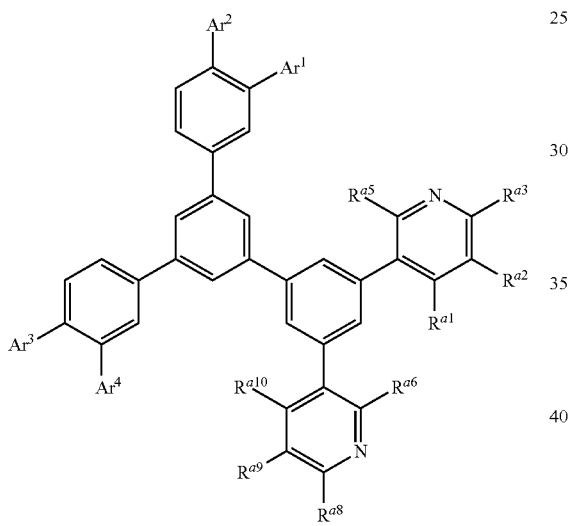
[Chemical Formula 1-G]
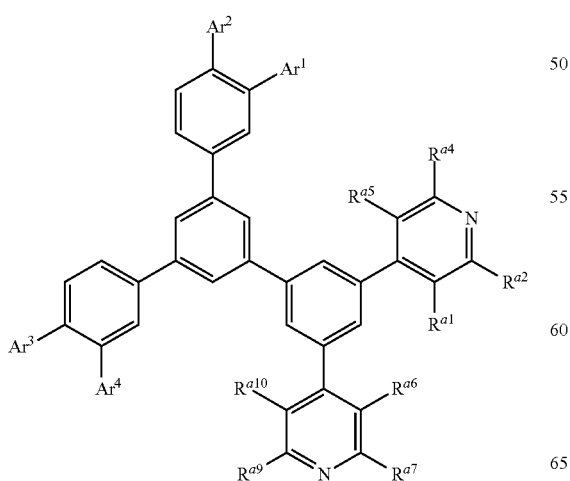
[Chemical Formula 1-H]
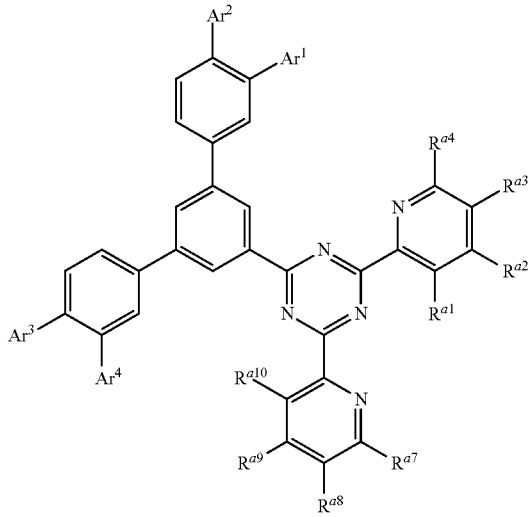
[Chemical Formula 1-I]
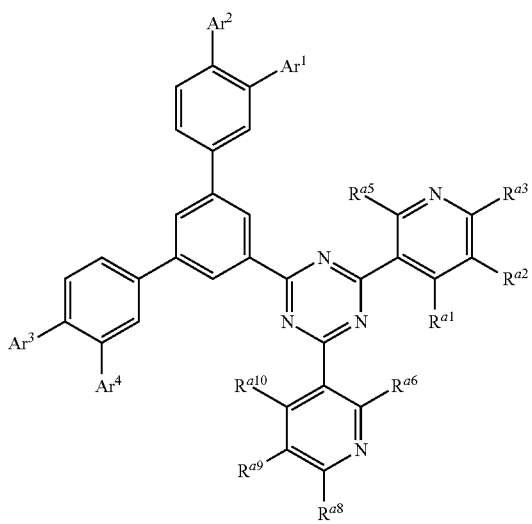
[Chemical Formula 1-J]
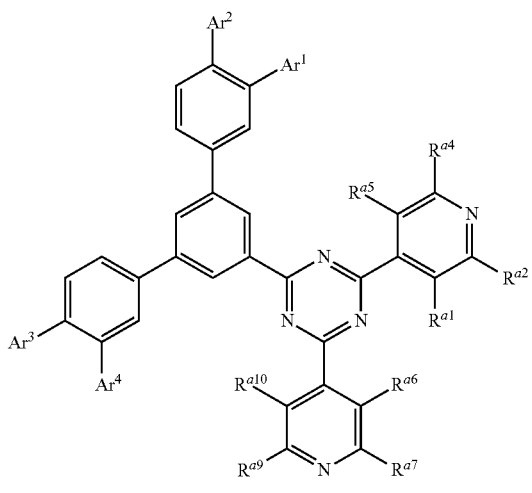
wherein, in Chemical Formulae 1-A to 1-J,
Ar¹ to Ar⁴ are independently selected from substituents of Group I, and $R^{a1}$ to $R^{a10}$ are independently hydrogen, deuterium, a substituted or unsubstituted C1 to C10 alkyl group, a C6 to C18 aryl group, or a combination thereof,
[Group I]
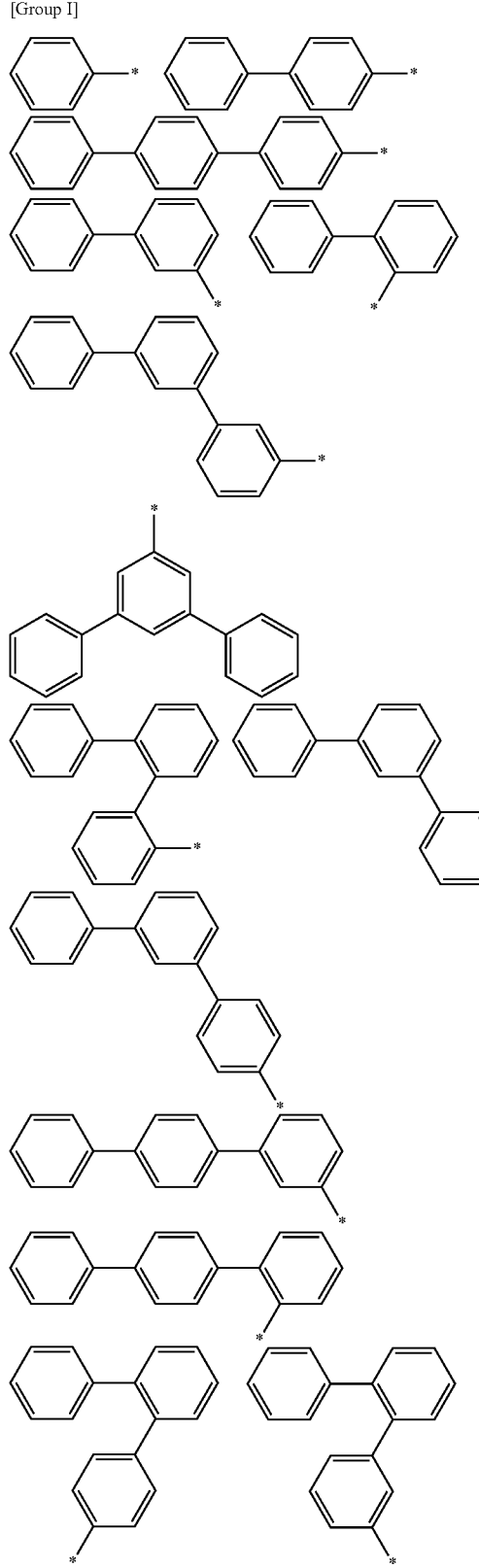
-continued
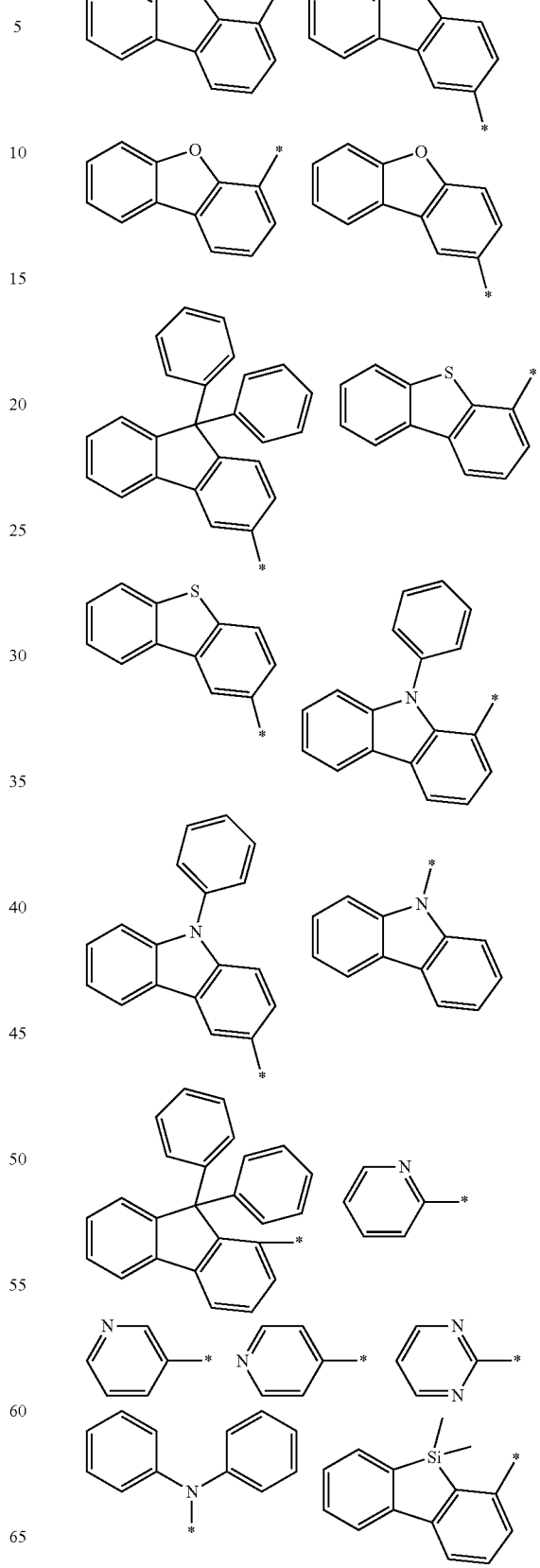

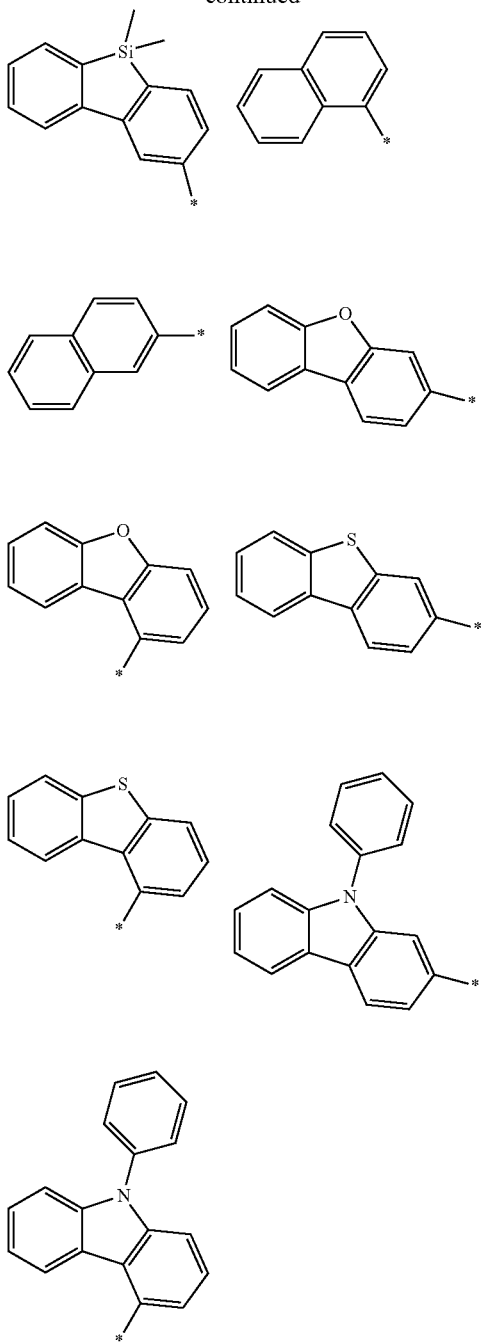

wherein, in Group I,
is a linking point.

3. The compound of claim 2, wherein $R^{a1}$ to $R^{a10}$ are independently hydrogen, deuterium, a substituted or unsubstituted phenyl group, a substituted or unsubstituted biphenyl group, or a substituted or unsubstituted terphenyl group.

4. A composition for an organic optoelectric device, comprising
the compound for an organic optoelectric device of claim 1 as a first compound; and at least one second compound for an organic optoelectric device represented by Chemical Formula 2:

[Chemical Formula 2]

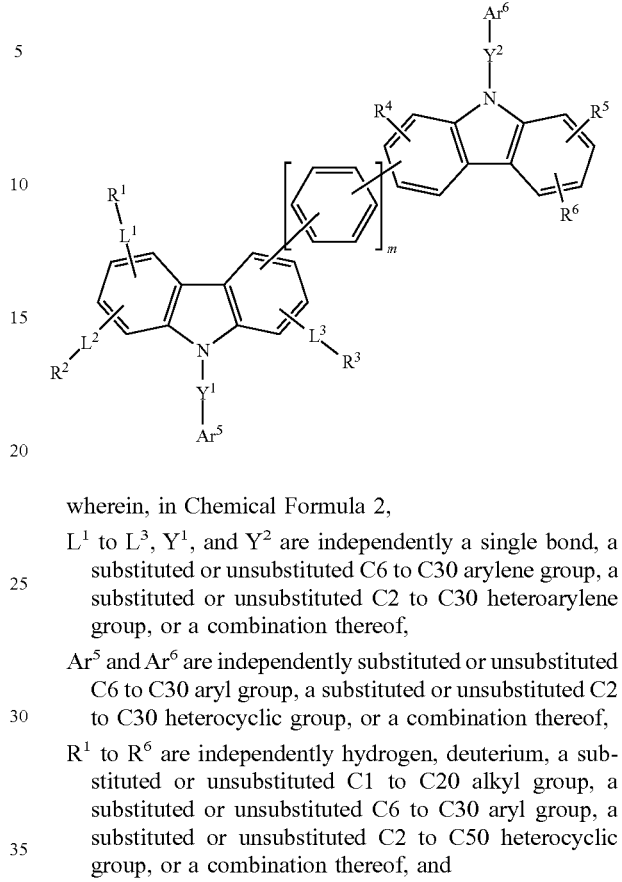

wherein, in Chemical Formula 2, $L^1$ to $L^3$, $Y^1$, and $Y^2$ are independently a single bond, a substituted or unsubstituted C6 to C30 arylene group, a substituted or unsubstituted C2 to C30 heteroarylene group, or a combination thereof, $Ar^5$ and $Ar^6$ are independently substituted or unsubstituted C6 to C30 aryl group, a substituted or unsubstituted C2 to C30 heterocyclic group, or a combination thereof, $R^1$ to $R^6$ are independently hydrogen, deuterium, a substituted or unsubstituted C1 to C20 alkyl group, a substituted or unsubstituted C6 to C30 aryl group, a substituted or unsubstituted C2 to C50 heterocyclic group, or a combination thereof, and m is an integer of 0 to 4.

5. The composition of claim 4, wherein $Ar^5$ and $Ar^6$ of Chemical Formula 2 are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted fluorenyl group, a substituted or unsubstituted pyridinyl group, a substituted or unsubstituted quinazolyl group, a substituted or unsubstituted isoquinazolyl group, a substituted or unsubstituted dibenzothiophenyl group, a substituted or unsubstituted dibenzofuranyl group, or a combination thereof.

6. The composition of claim 4, wherein Chemical Formula 2 includes one of substituents of Group II, and

*—$Y^1$—$Ar^5$ and *—$Y^2$—$Ar^6$ are one of substituents of Group III:

[Group II]

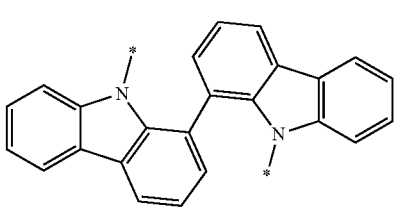

C-1

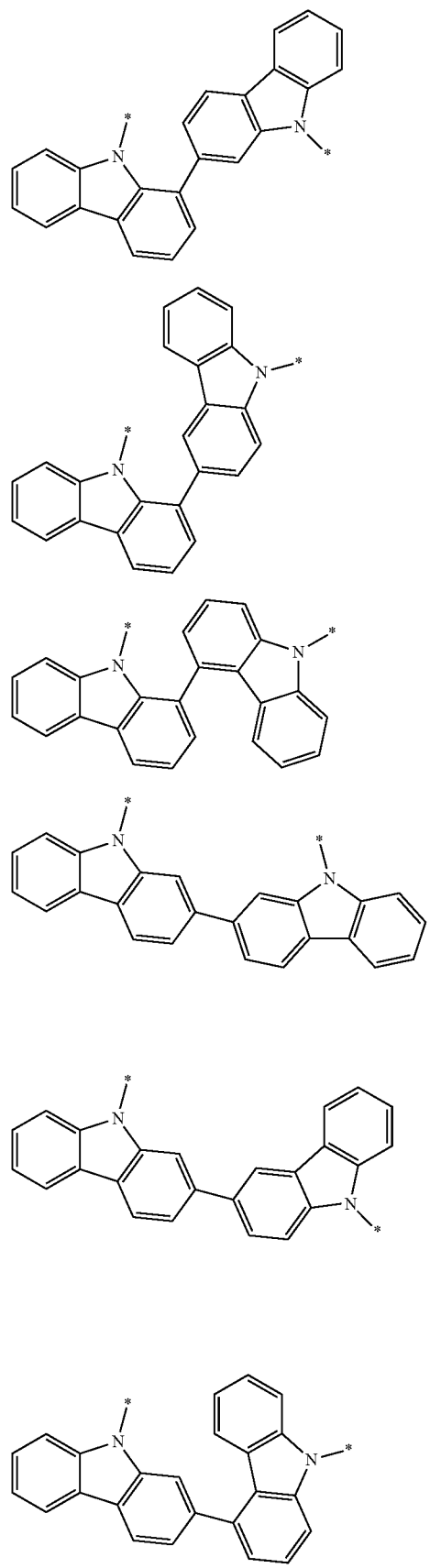
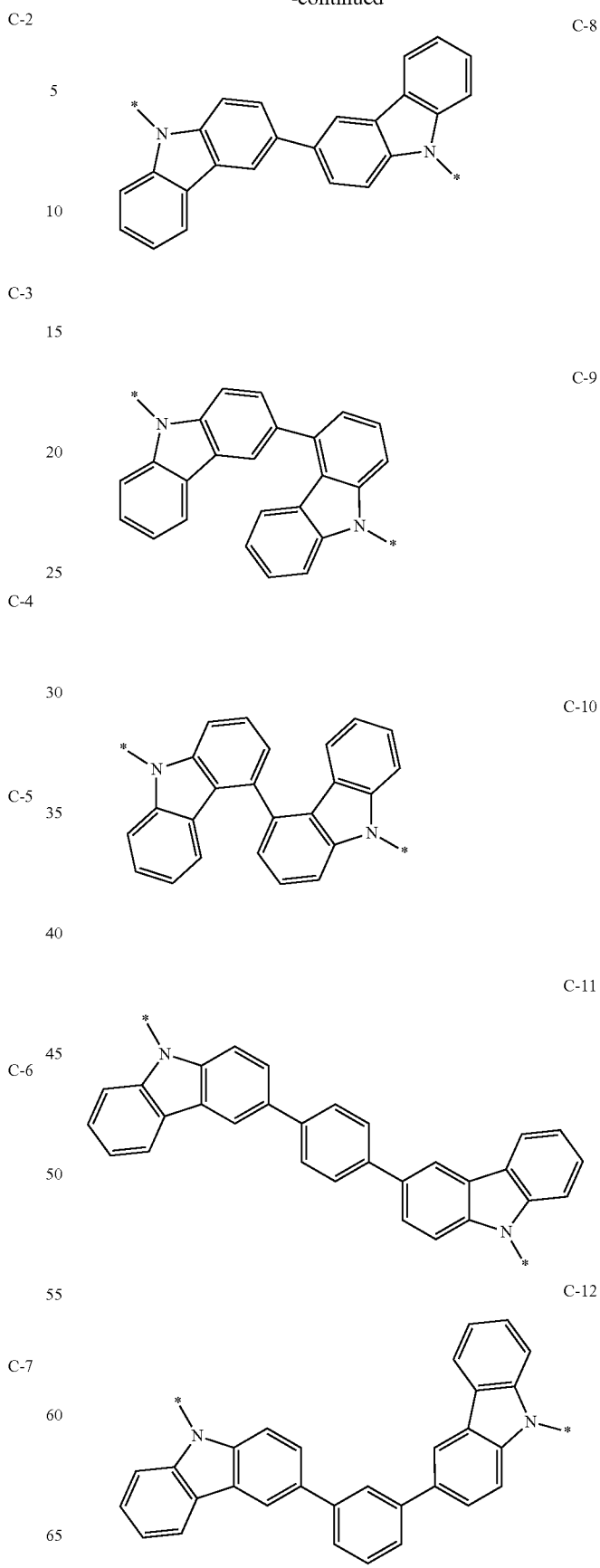

C-13
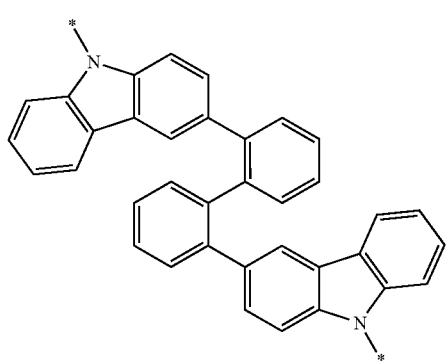
C-14
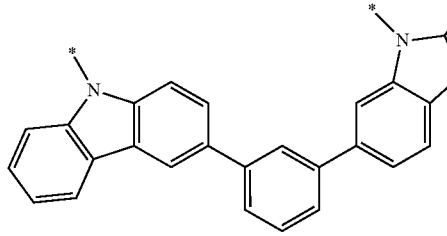
C-15
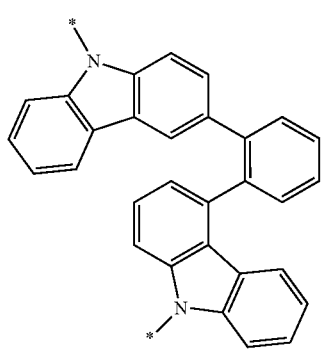
[Group III]
B-1
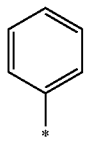
B-2
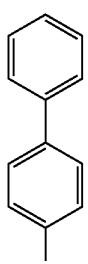
B-3
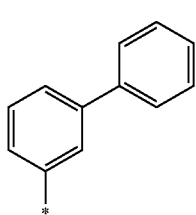
B-4
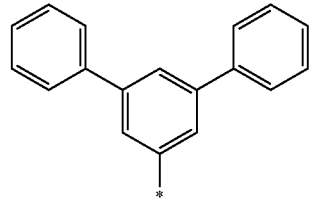
B-5
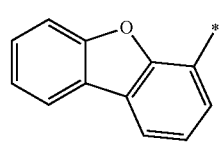
B-6
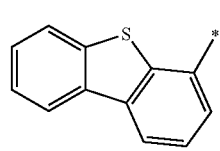
B-7
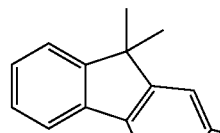
B-8
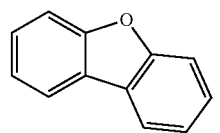
B-9
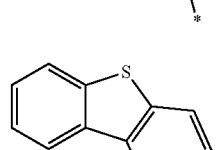
B-10
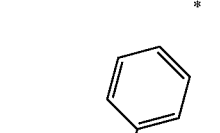
B-11

-continued

B-12
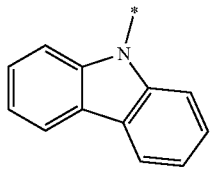

B-13
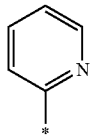

B-14
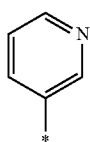

B-15
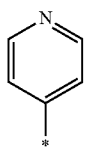

B-16
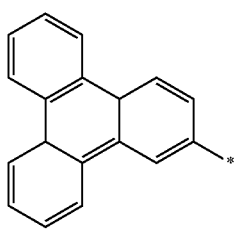

B-17
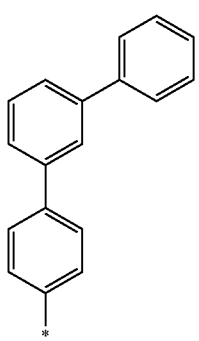

B-18
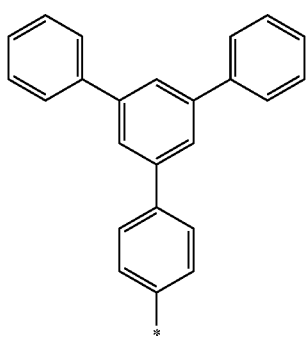

wherein, in Group II and Group III, * is a linking point.

7. The composition of claim 4, wherein the first compound for an organic optoelectric device is represented by Chemical Formula 1-A:

[Chemical Formula 1-A]

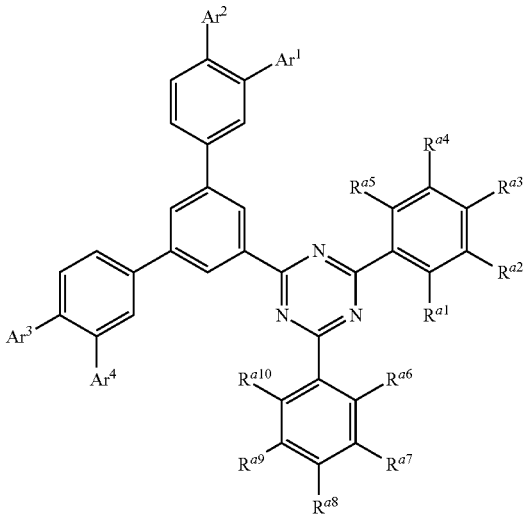

wherein, in Chemical Formula 1-A,
$Ar^1$ to $Ar^4$ are independently hydrogen, deuterium, a substituted or unsubstituted C6 to C30 aryl group, a substituted or unsubstituted carbazolyl group, a substituted or unsubstituted dibenzofuranyl group, a substituted or unsubstituted dibenzothiophenyl group, a substituted or unsubstituted pyridyl group, a substituted or unsubstituted pyrimidinyl group, or a combination thereof, and
$R^{a1}$ to $R^{a10}$ are independently hydrogen, deuterium, a substituted or unsubstituted C1 to C10 alkyl group, a C6 to C18 aryl group, or a combination thereof.

8. An organic optoelectric device, comprising
an anode and a cathode facing each other, and
at least one organic layer disposed between the anode and the cathode,
wherein the organic layer includes the compound for an organic optoelectric device of claim 1.

9. The organic optoelectric device of claim 8, wherein the organic layer includes a light-emitting layer, and
the light-emitting layer includes the compound for an organic optoelectric device.

10. The organic optoelectric device of claim 8, wherein the organic optoelectric device includes the compound for an organic optoelectric device as a host of the light-emitting layer.

11. The organic optoelectric device of claim 8, wherein the organic layer includes at least one auxiliary layer selected from a hole injection layer, a hole transport layer, an electron blocking layer, an electron transport layer, an electron injection layer, and a hole blocking layer, and
the auxiliary layer includes the compound for an organic optoelectric device.

12. A display device comprising the organic optoelectric device of claim 8.

13. An organic optoelectric device, comprising
an anode and a cathode facing each other, and
at least one organic layer disposed between the anode and the cathode, wherein the organic layer includes the composition for an organic optoelectric device of claim 4.

14. A display device comprising the organic optoelectric device of claim 13.

* * * * *